(12) United States Patent
Benjamin et al.

(10) Patent No.: US 8,217,085 B2
(45) Date of Patent: Jul. 10, 2012

(54) METHYLSULFONYLMETHANE (MSM) FOR TREATMENT OF DRUG RESISTANT MICROORGANISMS

(75) Inventors: Rodney Benjamin, Camas, WA (US); Jeffrey Varelman, Moyie Springs, ID (US); Anthony Keller, Ashland, OR (US)

(73) Assignee: Biogenic Innovations, LLC, Vancouver, WA (US)

( * ) Notice: Subject to any disclaimer, the term of this patent is extended or adjusted under 35 U.S.C. 154(b) by 0 days.

(21) Appl. No.: 13/399,921

(22) Filed: Feb. 17, 2012

(65) Prior Publication Data
US 2012/0149672 A1  Jun. 14, 2012

Related U.S. Application Data

(63) Continuation of application No. PCT/US2010/054837, filed on Oct. 29, 2010.

(60) Provisional application No. 61/256,935, filed on Oct. 30, 2009, provisional application No. 61/257,751, filed on Nov. 3, 2009, provisional application No. 61/259,098, filed on Nov. 6, 2009, provisional application No. 61/294,437, filed on Jan. 12, 2010.

(51) Int. Cl.
*A61K 31/10* (2006.01)
(52) U.S. Cl. ........................................ 514/711
(58) Field of Classification Search .......... None
See application file for complete search history.

(56) References Cited

U.S. PATENT DOCUMENTS

| | | | |
|---|---|---|---|
| 3,654,165 A | 4/1972 | Bryant et al. |
| 4,112,946 A | 9/1978 | Herschler |
| 4,296,130 A | 10/1981 | Herschler |
| 4,477,469 A | 10/1984 | Herschler |
| 4,514,421 A | 4/1985 | Herschler |
| 4,559,329 A | 12/1985 | Herschler |
| 4,568,547 A | 2/1986 | Herschler |
| 4,616,039 A | 10/1986 | Herschler |
| 4,863,748 A | 9/1989 | Herschler |
| 4,914,135 A | 4/1990 | Herschler |
| 4,973,605 A | 11/1990 | Herschler |
| 5,071,878 A | 12/1991 | Herschler |
| 5,753,696 A | 5/1998 | Shealy et al. |
| 6,183,758 B1 | 2/2001 | Scott |
| 6,328,987 B1 | 12/2001 | Marini |
| 6,416,772 B1 | 7/2002 | Van Engelen et al. |
| 6,426,370 B1 | 7/2002 | Hofschneider |
| 6,579,543 B1 | 6/2003 | McClung |
| 6,776,979 B2 | 8/2004 | Frager et al. |
| 7,371,407 B2 | 5/2008 | Farmer |
| 2001/0047038 A1 | 11/2001 | Moorman et al. |
| 2004/0001817 A1 | 1/2004 | Giampapa |
| 2004/0126440 A1 | 7/2004 | Frager et al. |
| 2005/0118291 A1 | 6/2005 | Wang et al. |
| 2006/0040871 A1 | 2/2006 | Levey et al. |
| 2006/0052438 A1 | 3/2006 | Ho et al. |
| 2006/0127508 A1 | 6/2006 | Larkins |
| 2007/0110731 A1 | 5/2007 | Riley |
| 2008/0038219 A1 | 2/2008 | Mosbaugh et al. |
| 2008/0228161 A1 | 9/2008 | Claussen et al. |
| 2008/0260708 A1 | 10/2008 | Hall |
| 2009/0017438 A1 | 1/2009 | Roy et al. |
| 2009/0017439 A1 | 1/2009 | Shimko et al. |

FOREIGN PATENT DOCUMENTS

| | | |
|---|---|---|
| WO | WO 94/05272 | 3/1994 |
| WO | WO 01/73096 | 10/2001 |
| WO | WO 2004/067013 | 8/2004 |
| WO | WO 2004/100896 | 11/2004 |
| WO | WO 2006/129149 | 12/2006 |

OTHER PUBLICATIONS

Lockie and Norcross, "A clinical study on the effects of dimethyl sulfoxide in 103 patients with acute and chronic musculoskeletal injuries and inflammations," *Ann. N.Y. Acad. Sci.*, 141:599-602, 1967.

Lu et al., "A mouse model for the evaluation of pathogenesis and immunity to Influenza A (H5N1) viruses isolated from humans," *J. Virol.*, 73:5903-5911, 1999.

Magnuson et al., Pharmacokinetics and distribution of [35S]—methylsulfonylmethane following oral administration in rats, *J. Agri. Food Chem.*, 55:2033-2038, 2006.

Magnuson et al., "Oral development toxicity of Methylsulfonylmethane in rats," *Food Chem. Toxicol.*, 45;977-984, 2007.

Martin and Hauthal, *Dimethyl Sulfoxide*, New York: John Wiley & Sons, 1971 (chapter 12, 21 pages).

Matsumoto, "Clinical trials of dimethyl sulfoxide in rheumatoid arthritis patients in Japan," *Ann. N.Y. Acad. Sci.*, 141:560-568, 1967.

Mitinskaia et al., "BCG vaccination and increasing the effectiveness of treatment of post-vaccination complications by the use of fifampicin and dimexide," *Probl. Tuberk*, 5:4-7, 1994 (with English Abstract).

Mohamaddi and O'Mara, "Unusual patient odor interfering with care," *Ann. Emerg. Med.*, 27:391-392, 1996.

Müller and Urbanczik, "Influence of dimethyl Sulfoxide (DMSO) on restoring sensitivity of mycobacterial strains resistant to chemotherapeutic compounds," *J. Antimicrob. Chemother.* 5:326-327, 1979.

Muravyev et al., "Effect of dimethyl sulfoxide and dimethyl sulfone on a destructive preocess (sic) in the joints of mice with spontaneous arthritis," *Patol Fiziol Eksp*, 2:37-39, 1991 (with English Abstract).

Nash and Steingrube, "In vitro drug sensitivity of M. Avium-Intracellulare complex in the presence and absence of dimethyl sulphoxide," *Microbios.*, 35:71-78, 1982.

Oshima et al., "The effect of distilled methylsulfonylmethane (MSM) on human chondrocytes in vitro," *Osteoarthritis and Cartilage*, 15:213, 2007.

(Continued)

*Primary Examiner* — James D Anderson
(74) *Attorney, Agent, or Firm* — Klarquist Sparkman, LLP

(57) ABSTRACT

Embodiments of the invention relate generally to the use of compositions comprising methylsulfonylmethane (MSM), and one or more therapeutic agents, for the treatment of drug-sensitive and drug resistant microorganisms. In several embodiments, such compositions are effective in treating drug resistant infectious diseases, for example, MRSA.

19 Claims, 7 Drawing Sheets

OTHER PUBLICATIONS

Ostojic et al., "Laboratory testing of cabin air filters for the removal of reduced-sulfur odors," *New Engine Design and Automotive Filtration SAE Special Publications*, 1362:41-58, 1998.

Paul, "Interval therapy with dimethyl sulfoxide," *Ann. N. Y. Acad. Sci.*, 141:586-598, 1967.

Paulus, "FDA advisory committee meeting: methotrexate; guidelines for the clinical evaluation of anti-inflammatory drugs: DMSO in scleroderma," *Arthritis heum.*, 29:1289-1290, 1986.

Penrod et al., "Dimethyl sulfoxide for incisional pain after thoracotomy: Preliminary Report," *Ann. N.Y. Acad. Sci.*, 141:493-495, 1967.

Pottz et al., "The effect of dimethyl Sulfoxide (DMSO) on antibiotic sensitivity of a group of medically important microorganisms: preliminary report," *Ann. N.Y. Acad. Sci.*, 141:261-272, 1967.

Pratt et al., "A study of the absorption of OptiMSM (methylsulfonylmethane) in horses," *Proc. 17th Equine Nutr. Physiol. Soc.*, pp. 141-142, 2001.

Ropek et al., "Effects of dimethyl sulfoxide on *Tubercle bacilli* resistant to INH," *Gruzlica.*, 39:738-741, 1971.

Seibert, "DMSO and other combatants against bacteria isolated from leukemia and cancer patients," *Ann. N.Y. Acad. Sci.*, 141:175-201, 1967.

Shanmugam et al. "The effects of methylsulfonylmethane on hair growth promotion of magnesium ascorbyl phosphate for the treatment of alopecia," *Biomolecules and Ther.*, 17:241-248, 2009.

Shaklee Health Network, "Methyl Sulfonyl Methane," retrieved from the internet on Dec. 16, 2010; URL:http://content.nhiondemand.com/shp/monoVMN.asp?objID=100028.

Simon et al., "Efficacy and safety of topical diclofenac containing dimethyl sulfoxide (DMSO) compared with those of topical placebo, DMSO vehicle and oral diclofenac for knee osteoarthritis," *Pain*, 143:238-245, 2009.

Smith et al., "Anti-inflammatory effects of topically applied dimethylsulphoxide gel on endotoxin-induced synovitis in horses," *Am. J. Vet. Res.*, 59:1149-52, 1998.

Steinberg, "The employment of DMSO as an anti-inflammatory agent and steroid transporter in diversified clinical diseases," *Ann. N.Y. Acad. Sci.*, 141:532-550, 1967.

Sturenberg, "Rapid detection of methicillin-resistant *Staphylococcus aureus* directly from clinical samples: methods, effectiveness and cost considerations," *GMS*, 7:1-19, 2009.

Szmant, "Physical properties of dimethyl sulfoxide and its function in biological systems," *Ann. N.Y. Acad. Sci.*, 243:20-23, 1975.

Szydlowska, "Studies on the role of dimethylsulfoxide in resensibilization of antibiotic-resistant bacterial strains," *Arch. Immunol. Ther. Exp. (Warsz)*, 20:193-202, 1972.

Szydlowska, "In vitro and in vivo Studies on the Role of Dimethylsulfoxide (DMSO) in Resensibilization of Bacterial Strains Resistant to Antibiotics and Chemotherapeutic Agents," *Abl. Bakt. Hyg.*, 239:270-274, 1977.

Szydlowska and Pawlowska, "Comparative studies on the influence of dimethylsulfoxide (DMSO) on reversion to sensitivity to isonicotinic acid hydrazide (INH) and rifampicin (RMP) in resistant strains of *Tubercle bacilli*," *Arch. Immunol. Ther. Exp. (Warsz)*, 24:575-577, 1976.

Szydlowska and Pawlowska, "In vivo studies on reversion to sensitivity of INH-resistant tubercle bacilli under the influence of dimethylsulfoxide (DMSO)," *Arch. Immunol. Ther. Exp. (Warsz).*, 22(4):559-561, 1974.

Teigland and Saurino, "Clinical evaluation of dimethyl sulfoxide in equine applications," *Ann. N.Y. Acad. Sci.*, 141:471-477, 1967.

Tiews et al., "Metabolism and excretion of dimethyl sulfoxide in cows and calves after topical and parenteral application," *Ann. N.Y. Acad. Sci.*, 243:139-150, 1975.

Usha and Naidu, "Randomized, double-blind, parallel, placebo-controlled study of oral glucosamine, methylsulfonylmethane and their combination in osteoarthritis," *Clin. Drug. Invest.*, 24:353-363, 2004.

Vignes, "Dimethyl Sulfoxide: a superior solvent underutilized because of a safety myth," *Semiconductor Safety Association Annual Meeting*, Arlington, VA, Apr. 25-28, 2000.

Vuopala et al., "The analgesic action of DMSO ointment in arthrosis," *Acta. Rheum. Scand.*, 17:57-60, 1971.

Wierzbicki, "Homocysteine and cardiovascular disease: a review of the evidence" *Diabetes and Vascular Disease Research*, 4:143-149, 2007.

Williams et al., "Metabolism of dimethyl sulfide, dimethyl sulfoxide and dimethyl sulfone in the rabbit," *Arch. Biochem. Biophys.*, 117:84-87, 1966.

Windrum et al., "Variation in dimethyl sulfoxide use in stem cell transplantation: a survey of EBMT centres," *Bone Marrow Transplantation.*, 36:601-603, 2005.

Wong et al., "Absorption, excretion and biotransformation of dimethyl sulfoxide in man and miniature pigs after topical application as an 80% gel," *J. Invest. Dermatol.*, 56:44-48, 1971.

Wood and Wood, "Pharmacologic and biochemical consideration of dimethyl sulfoxide," *Ann. N.Y. Acad. Sci.*, 143, 7-19, 1975.

Zhang et al., "Assessment of methylsulfonylmethane as a permeability enhancer for regional EDTA chelation therapy," *Drug Delivery*, 16:243-248, 2009.

Zuckner et al., "Local application of dimethyl sulfoxide and DMSO combined with triacinolone acetonide in rheumatoid arthritis," *Ann. N.Y. Acad. Sci.*, 141:555-559, 1967.

"Additive Free MSM Methylsulfonylmethane," http://www.worldimagenaturals.com/products/msm/indes.php, 5 pages, downloaded Aug. 18, 2010.

"AloeCalm™ All-Natural and Organic Body Lotion," http://www.acne-answrs.org/products/aloe-calm.html,6 pages, downloaded Jul. 5, 2010.

"How to Flush the Toxins out of Your Body from the Swine or H1N1 Flu Shot," http://www.ehow.com, 3 pages, downloaded Aug. 18, 2010.

"Methylsulfonylmethane," http://en.wikipedia.org/wiki/Methylsulfonylmethane, 5 pages, downloaded Jul. 5, 2010.

"MSM—MethylSulfonylMethane," http://pages.prodigy.net/naturedoctor/msm.html, 6 pages, downloaded Jul. 5, 2010.

"Sulfur (MSM): A Basic Essential Nutrient Needed, Now, More than Ever Before," http://www.all-natuarl.com/msm.html, 7 pages, downloaded Aug. 11, 2010.

Borodina et al., "Dimethylsulfone as a growth substrate for novel methylotrophic species of *Hyphomicrobium* and *Arthrobacter*," *Arch. Microbiol.*, 173(5-6):425-437, 2000.

International Search Report issued by the Australian Patent Office on Jan. 31, 2011 in related parent application PCT/US2010/054837 (3 pages).

Written Opinion issued by the Australian Patent Office on Jan. 31, 2011 in related parent application PCT/US2010/054837 (4 pages).

Alekesvich et al., "Increase in the sensitivity of pathologic gum recessed microflora to streptomycin under effect of dimexide and trypsin," *Mikrobiol Zh.*, 35:766-769, 1973 (English Abstract).

Andrews, "Determination of minimum inhibitory concentrations," *J. of Antimicrobial Chemotherapy*, 48:5-16, 2001.

Barrager et al., "A multicentered, open-label trial on the safety and efficacy of methylsulfonylmethane in the treatment of seasonal allergic rhinitis," *J. Alt. Complem. Med.*, 8:167-173, 2002.

Beilke et al., "Effects of dimethyl sulphoxide on the oxidative function of human neutrophils," *J. Lab. Clin. Med.*, 110:91-96, 1987.

Berry et al., "Natural Gas Odorants Desulfurization," AIChE Ann. Meet. Conf. Proc., 2004 (8 pages).

Blumenthal and Fuchs, "The clinical use of dimethyl sulfoxide on various headaches, musculosekeletal, and other general medical disorders," *Ann. N.Y. Acad. Sci.*, 141:572-585, 1967.

Bookman et al., "Effect of a topical diclofenac solution for relieving symptoms of primary osteoarthritis of the knee: a randomized controlled trial," *JAMC*, 171(4):333-338, 2004.

Brandt, et al., "Selective affinity of dimethyl sulphoxide (DMSO) and 2-amin-4-phenyl sulphonylbenzenesulphonamide (NSD 3004) for the large intestinal mucosa of mice," *Acta. Pharmacol. Toxicol.*, 51:173-176, 1982.

Brayton, "Dimethyl Sulfoxide (DMSO): A Review," *The Cornel Veterinarian*, 76:61-69, 1986.

Brechner et al., "Dermal anesthesia by the topical application of tetracaine base dissolved in dimethyl sulfoxide," *Ann. N.Y. Acad. Sciences*, 141:524-531, 1967.

Brien et al., "Systematic review of the nutritional supplements dimethyl sulfoxide (DMSO) and methylsulfonylmethane (MSM) in the treatment of osteoarthritis" *Osteoarthritis and Cartilage*, 16:1277-1288, 2008.

Brien et al., "Meta-analysis of the related nutritional supplements dimethyl sulfoxide and methylsulfonylmethane in the treatment of osteoarthritis of the knee," *eCAM*, doi:10.1093/ecam/nep045, 10 pages, 2009.

Brown et al., "Guidelines for the laboratory diagnosis and susceptibility testing of methicillin-resistant *Staphylococcus aureus* (MRSA)," *J. Antimicrob. Chemother.*, 56, 1000-1018, 2005.

Brown, "Clinical experience with DMSO in acute musculoskeletal conditions comparing a non-controlled series with a controlled double blind study," *Ann. N.Y. Acad. Sci.*, 141:496-505, 1967.

Dancer, "The effect of antibiotics on methicillin-resistant *Staphylococcus aureus*," *J. Antimicrob. Chemother.*, 61:246-253, 2008.

De Lencastre et al., "Antibiotic resistant *Staphylococcus aureus*: a paradigm of adaptive power," *Curr. Opin. Microbiol.*, 10, 428-435, 2007.

Debi et al., "The role of MSM in knee osteoarthritis: a double blind, randomized prospective study," *Osteoarthritis and Cartilage*, 15:427, 2008.

Demos et al., "Dimethyl Sulfoxide in Musculoskeletal Disorders," *Ann. N.Y. Acad. Sci.*, 141:517-523, 1967.

Eberhardt et al., "DMSO in patients with activated gonarthrosis," *Fortschr. Med.*, 113:446-450, 1995 (Abstract only).

Evans et al., "Dimethylsulfoxide (DMSO) blocks conduction in peripheral nerve C fibers: a possible mechanism of analgesia," *Neurosci. Lett.*, 150:145-148, 1984.

Feldman et al., "In vivo and in vitro effects of dimethyl sulfoxide on streptomycin-sensitive and—resistant *Escherichia coli*," *Ann. N.Y. Acad. Sci.*,243:269-277, 1975.

Gerhards and Gibian, "The metabolism of dimethyl sulfoxide and its metabolic effects in man and animals," *Ann. N.Y. Acad. Sci.*, 141:65-76, 1967.

Glasser, "Dimethylsulfoxide (DMSO) "resensibilization" as potential chemotherapy for opportunistic mycobacterial disease," *Am. Rev. Respir. Dis.*, 118:969-970, 1978.

Gorbach and Samtsov, "Therapeutic possibilities of inhalation of rifampicin with dimexide in phthisiopulmonolgy," *Probl. Tuberk.*, 3:34-36, 1991 (with English Abstract).

Gupta, "New delivery systems for topical nutraceutical (nutracosmetic) and cosmeceutical formulations," *Business Briefing: Global Cosmetic Manufacturing*, 1-5, 2004.

Haigler and Spring, "Comparison of the analgesic effect of dimethyl sulfoxide and morphine," *Ann. N.Y. Acad. Sci.*, 411:19-27, 1983.

Hasegawa, Suppressive effects of methylsulfonylmethane (MSM) on type II collagen induced arthritis in DBA/iJ mice, *J. Pharmacol. Ther.*, 32:421-427, 2004.

Horvath et. al., "Toxicity of methylsulfonylmethane in rats," Food Chem. Toxicol., 40:1459-62, 2002.

Hucker, et al., "Studies on the absorption, excretion and metabolism of dimethylsulfoxide (DMSO) in man," *J. Pharmacol. Exp. Therap.* ,155:309-317, 1967.

Jacob and Appleton, "MSM: The Definitive Guide: A comprehensive review of the science and therapeutics of Methylsulfonylmethane," *Freedom Press*, Topanga, CA, 2003 (51 pages).

Jacob and Herschler, "Dimethyl sulfoxide after twenty years," *Ann. N.Y. Acad. Sci.*, 411:14-18, 1983.

Jacob and Herschler, "Pharmacology of DMSO," *Cryobiology*, 23:14-27, 1986.

Jacob et al., "The miracle of MSM: the natural solution for pain," pp. 51-97; pp. 122-132; pp. 139-144; pp. 191-214, *Berkley Trade*, 1999.

Jacob and Wood, "Dimethyl sulfoxide (DMSO): toxicology, pharmacology, and clinical experience," *Am. J. Surg.*, 114:414-426, 1967.

Jagannath et al., "Enhancement of drug susceptibility of multi-drug resistant strains of *Mycobacterium tuberculosis* by ethambutol and dimethyl sulphoxide," *J. Antimicrob. Chemother.*, 35(3):381-390, 1995.

Jimenez and Willkens, "Dimethyl Sulphoxide: a perspective of its use in rheumatic diseases," *J. Lab. Clin. Med.*, 100:489-500, 1982.

John and Laudahn, "Clinical experiences with the topical application of DMSO in orthopedic diseases: evaluation of 4180 cases," *Ann. N.Y. Acad. Sci.*, 141:506-516, 1967.

Karlson and Ulrich, "Stability of rifampin in dimethylsulfoxide," *Appl. Microbiol.*, 18:692-693, 1969.

Kim et al., "Efficacy of methylsulfonylmethane (MSM) in osteoarthritis pain of the knee: a pilot clinical trial," *OsteoArthritis and Cartilage*, 14:286-294, 2006.

Knowles "Clinical experience with DMSO in small animal practice," *Ann. N.Y. Acad. Sci.*, 141:478-483, 1967.

Koenen et al., "Percutaneous therapy of activated osteoarthritis of the knee—comparison between DMSO and diclofenac," *Therapiestudie*, 38:534-538, 1996 (with English Abstract).

Layman and Jacob, "The absorption, metabolism, and excretion of dimethyl sulfoxide by rhesus monkeys" *Life Sciences*, 37:2431-2437, 1985.

Lee et al., "Evaluation of genotoxicity on plant derived dietary sulfur," *J. Microbiol. Biotech.*, 16:817-820, 2006.

Liubinets and Kruk, "Applying dimexide in treatment of endobronchitis in patients with destructive forms of pulmonary tuberculosis," *Zh Ushn Nos Gorl. Bolesn.*, 29:68-71, 1969 (with English Abstract).

METHYLSULFONYLMETHANE (MSM) FOR TREATMENT OF DRUG RESISTANT MICROORGANISMS

CROSS REFERENCE TO RELATED APPLICATIONS

This is a continuation of co-pending International Application No. PCT/US2010/054837, filed Oct. 29, 2010, which was published in English under PCT Article 21(2), which in turn claims priority to U.S. Provisional Application No. 61/256,935, filed Oct. 30, 2009, U.S. Provisional Application No. 61/257,751, filed Nov. 3, 2009, U.S. Provisional Application No. 61/259,098 filed Nov. 6, 2009, and U.S. Provisional Application No. 61/294,437, filed Jan. 12, 2010. All of the prior filings are incorporated herein in their entirety.

FIELD

This disclosure relates generally to compositions comprising methylsulfonylmethane (MSM) to treat drug resistant infectious diseases. Certain embodiments relate to sensitizing drug resistant microbes to drugs. Several compositions disclosed herein are useful for treating MRSA, for instance.

BACKGROUND

Methylsulfonylmethane (MSM; $(CH_3)_2SO_2$), also known as dimethyl sulfone, is an organosulfur compound that is a metabolite of DMSO and certain sulfur-containing amino acids. MSM has been marketed primarily as a dietary supplement.

Infectious diseases are diseases caused by pathogenic microbial agents, including viruses, bacteria, fungi, parasites, and prions, among others. Despite certain improvements in medical treatment for infectious diseases (antibiotics and vaccines), there remain many obstacles to reducing the mortality caused by infectious diseases. A primary issue is the emergence and spread of drug resistant pathogens.

Methicillin resistant *Staphylococcus aureus* (MRSA) is a drug resistant bacterial pathogen that is especially troublesome in hospitals where patients with open wounds, invasive devices and weakened immune systems are at greater risk of infection than the general public. Thus, there exists a need for an effective and easily administered therapy against drug resistant infectious diseases.

SUMMARY

Described herein is the unexpected discovery that MSM sensitizes drug resistant bacterial pathogens, include MRSA, to a drug to which they are resistant. Thus, surprisingly, a drug resistant bacterial pathogen can be sensitized to a drug the pathogen is resistant to by contacting the pathogen with MSM, and can be inhibited by contacting the pathogen with both MSM and a drug to which the pathogen is otherwise resistant.

Thus, there is provided herein is a method of inhibiting a drug resistant bacterial pathogen, which method involves selecting a drug resistant bacterial pathogen; and contacting the bacterial pathogen with a composition comprising a therapeutically effective amount of MSM and a therapeutically effective amount of an agent that inhibits the drug-sensitive form of the drug resistant bacterial pathogen, thereby inhibiting a drug resistant bacterial pathogen. In some embodiments, the drug resistant bacterial pathogen is MRSA.

Also provided is a method of sensitizing a drug resistant bacterial pathogen to a drug the bacterial pathogen is resistant to, which method comprises selecting a drug resistant bacterial pathogen; and contacting the bacterial pathogen with a composition comprising a therapeutically effective amount of MSM, thereby sensitizing the drug resistant bacterial pathogen to the drug the bacterial pathogen is resistant to. In some embodiments, the drug resistant bacterial pathogen is MRSA.

Also provided herein is a method of inhibiting a drug-sensitive bacterial pathogen from developing drug resistance, which method comprises selecting a drug sensitive bacterial pathogen; and contacting the drug-sensitive bacterial pathogen with a composition comprising a therapeutically effective amount of MSM and a therapeutically effective amount of an agent that inhibits the drug-sensitive bacterial pathogen, thereby inhibiting the drug-sensitive bacterial pathogen from developing drug resistance. In some embodiments, the drug sensitive bacterial pathogen is *Staphylococcus aureus*.

In various embodiments of the methods described herein, the bacterial pathogen is in (or on) a subject. In some embodiments, the composition is administered to the subject topically or with an inhalant device.

In some embodiments, the agent is a Beta-lactam (β-lactam) antibiotic.

In various embodiments, the effective amount of MSM is about 5-20% MSM, about 5-16% MSM, about 5-10% MSM, about 5-8% MSM, about 9-16% MSM or about 10-15% MSM. MSM (weight percent of the composition comprising MSM).

In one particular embodiment of a method of inhibiting a drug resistant bacterial pathogen, the bacterial pathogen is MRSA, the agent is a Beta-lactam antibiotic, the effective amount of MSM is about 5-10% MSM weight percent, and the composition is administered topically.

In one particular embodiment of method of sensitizing a drug resistant bacterial pathogen to a drug the bacterial pathogen is resistant to, the bacterial pathogen is MRSA, the effective amount of MSM is about 5-10% MSM weight percent, and the composition is administered topically.

In one particular embodiment of a method of inhibiting a drug-sensitive bacterial pathogen from developing drug resistance, the bacterial pathogen is *Staphylococcus aureus*, the agent is a Beta-lactam antibiotic, the effective amount of MSM is about 5-10% MSM, and the composition is administered topically.

It will be further understood that the methods of sensitizing or inhibiting bacterial pathogens disclosed herein are useful beyond the specific circumstances that are described in detail herein, and for instance are expected to be useful for any number of conditions wherein a bacterial pathogen has become drug resistant or where it is desirable to inhibit a drug sensitive bacterial pathogen from becoming drug resistant.

DETAILED DESCRIPTION

Figure 1:
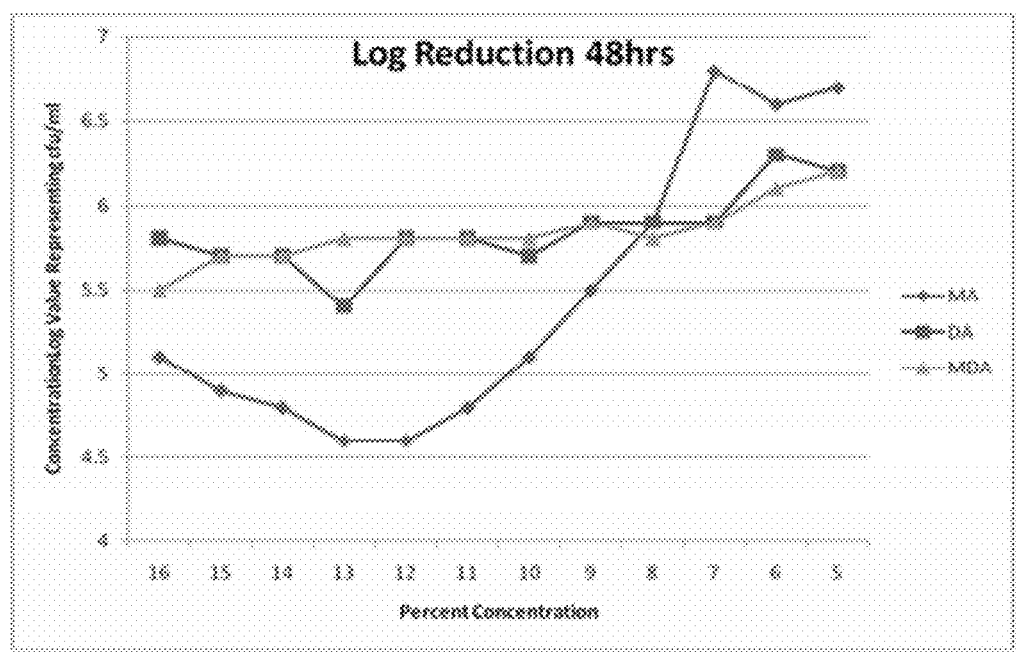
FIG. 1 is a graph illustrating that MSM sensitizes MRSA to oxacillin. In vitro survival of ATCC strain 43300 *staphylococcus aureus* (a MRSA strain resistant to oxacillin and methicillin), was tested in the presence of MSM, DMSO and oxacillin ATCC strain 43300 *staphylococcus aureus* was incubated with 5-16% MSM and 6 µg/ml oxacillin ("MA"), 5-16% MSM, 6 µg/ml oxacillin and 1% DMSO ("MDA"), or 1% DMSO and 6 µg/ml oxacillin ("DA"), for 48 hours at 25° C. 6 µg/ml oxacillin is the MIC for this strain of MRSA (ATCC). The initial inoculation of bacteria was $3.15 \times 10^7$ cfu/ml (Log=7.49). All conditions tested showed a decrease in cfu/ml over the 24 hour period tested. The positive control showed TNTC (too numerous to count) on the $10^7$ dilution plate. A lower survival rate was observed in the presence of 9-16% MSM with 6 µg/ml oxacillin than in the presence of 1% DMSO and 6 µg/ml oxacillin or in the presence of 1% DMSO, 9-16% MSM and 6 µg/ml oxacillin. The lowest survival rate was observed in the 12 and 13% MSM with 6 µg/ml antibiotic conditions. These results show that specific concentrations of MSM alone can increase the sensitivity of a MRSA strain to antibiotic more efficaciously than DMSO or a combination of MSM and DMSO.

| I. Terms and Abbreviations | |
| --- | --- |
| CFU | colony forming units |
| DMEM | Dulbecco's modified eagle medium |
| DMSO | dimethyl sulfoxide |
| DNA | deoxyribonucleic acid |
| ELISA | enzyme-linked immunosorbent assay |
| $IC_{50}$ | inhibitory concentration 50 |
| LAB | lactic acid bacteria |
| MDSA | multidrug resistant *Staphylococcus aureus* |
| MDR | multidrug resistant |
| MIC | minimum inhibitory concentration |
| MRSA | methicillin resistant *Staphylococcus aureus* |
| MSM | methylsulfonylmethane |
| OSRA | oxacillin-resistant *Staphylococcus aureus* |
| PAGE | polyacrylamide-gel electrophoresis |
| PBP | penicillin binding protein |
| PBS | phosphate buffered saline |
| PDA | potato dextrose agar |
| SDS | sodium dodecyl sulfate |
| TNTC | too numerous to count |
| TSB | tryptic soy broth |

The following explanations of terms and methods are provided to better describe the present disclosure and to guide those of ordinary skill in the art in the practice of the present disclosure. The singular forms "a," "an," and "the" refer to one or more than one, unless the context clearly dictates otherwise. For example, the term "comprising a bacterial cell" includes single or plural bacterial cells and is considered equivalent to the phrase "comprising at least one bacterial cell." The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting. For example, conventional methods well known in the art to which a disclosed invention pertains are described in various general and more specific references, including, for example, Sambrook et al., *Molecular Cloning: A Laboratory Manual*, 2d ed., Cold Spring Harbor Laboratory Press, 1989; Sambrook et al., *Molecular Cloning: A Laboratory Manual*, 3d ed., Cold Spring Harbor Press, 2001; Ausubel et al., *Current Protocols in Molecular Biology*, Greene Publishing Associates, 1992 (and Supplements to 2000); Ausubel et al., *Short Protocols in Molecular Biology: A Compendium of Methods from Current Protocols in Molecular Biology*, 4th ed., Wiley & Sons, 1999; Harlow and Lane, *Antibodies: A Laboratory Manual*, Cold Spring Harbor Laboratory Press, 1990; and Harlow and Lane, *Using Antibodies: A Laboratory Manual*, Cold Spring Harbor Laboratory Press, 1999; Loudon, *Organic Chemistry*, Fourth Edition, New York: Oxford University Press, 2002, pp. 360-361, 1084-1085; Smith and March, *March's Advanced Organic Chemistry: Reactions, Mechanisms, and Structure*, Fifth Edition, Wiley-Interscience, 2001; or Vogel, *A Textbook of Practical Organic Chemistry, Including Qualitative Organic Analysis*, Fourth Edition, New York: Longman, 1978.

Additional terms commonly used in molecular genetics can be found in Benjamin Lewin, *Genes V* published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

Additional terms commonly used in chemistry can be found in Loudon, *Organic Chemistry*, Fourth Edition, New York: Oxford University Press, 2002, pp. 360-361, 1084-1085; Smith and March, *March's Advanced Organic Chemistry: Reactions, Mechanisms, and Structure*, Fifth Edition, Wiley-Interscience, 2001; or Vogel, *A Textbook of Practical Organic Chemistry, Including Qualitative Organic Analysis*, Fourth Edition, New York: Longman, 1978.

Administration: To provide or give a subject, cell, or surface, a compound or agent, such as MSM, or composition comprising a compound or agent, such as MSM, by any effective route. Exemplary routes of administration to a surface include spraying or wiping an agent or composition containing an agent onto the surface. Exemplary routes of administration to a subject include, but are not limited to, injection (such as subcutaneous, intramuscular, intradermal, intraperitoneal, and intravenous), oral, sublingual, rectal, transdermal (such as topical), intranasal, vaginal and inhalation routes. Particular types of administration to a subject include topical administration or administration to the nasal mucosa or lungs by inhalational administration.

Agent: Any substance or any combination of substances that is useful for achieving an end or result; for example, a substance or combination of substances useful for inhibiting bacterial growth or survival. Examples of agents include MSM, DMSO and Beta-lactam antibiotics, among others. Agents include anti-microbial agents, which are useful for inhibiting a microbe. Antibiotic agents are useful for inhibiting bacteria.

Bacterial pathogen: A bacteria that causes disease (pathogenic bacteria). Examples of pathogenic bacteria for which MSM may be used to modify include without limitation any one or more of (or any combination of) *Acinetobacter baumanii, Actinobacillus* sp., *Actinomycetes, Actinomyces* sp. (such as *Actinomyces israelii* and *Actinomyces naeslundii*), *Aeromonas* sp. (such as *Aeromonas hydrophila, Aeromonas veronii biovar sobria* (*Aeromonas sobria*), and *Aeromonas caviae*), *Anaplasma phagocytophilum, Alcaligenes xylosoxidans, Acinetobacter baumanii, Actinobacillus actinomycetemcomitans, Bacillus* sp. (such as *Bacillus anthracis, Bacillus cereus, Bacillus subtilis, Bacillus thuringiensis*, and *Bacillus stearothermophilus*), *Bacteroides* sp. (such as *Bacteroides fragilis*), *Bartonella* sp. (such as *Bartonella bacilliformis* and *Bartonella henselae, Bifidobacterium* sp., *Bordetella* sp. (such as *Bordetella pertussis, Bordetella parapertussis*, and *Bordetella bronchiseptica*), *Borrelia* sp. (such as *Borrelia recurrentis*, and *Borrelia burgdorferi*), *Brucella* sp. (such as *Brucella abortus, Brucella canis, Brucella melintensis* and *Brucella suis*), *Burkholderia* sp. (such as *Burkholderia pseudomallei* and *Burkholderia cepacia*), *Campylobacter* sp. (such as *Campylobacter jejuni, Campylobacter coli, Campylobacter lari* and *Campylobacter fetus*), *Capnocytophaga* sp., *Cardiobacterium hominis, Chlamydia trachomatis, Chlamydophila pneumoniae, Chlamydophila psittaci, Citrobacter* sp. *Coxiella burnetii, Corynebacterium* sp. (such as, *Corynebacterium diphtheriae, Corynebacterium jeikeum* and *Corynebacterium*), *Clostridium* sp. (such as *Clostridium perfringens, Clostridium difficile, Clostridium botulinum* and *Clostridium tetani*), *Eikenella corrodens, Enterobacter* sp. (such as *Enterobacter aerogenes, Enterobacter agglomerans, Enterobacter cloacae* and *Escherichia coli*, including opportunistic *Escherichia coli*, such as enterotoxigenic *E. coli*, enteroinvasive *E. coli*, enteropathogenic *E. coli*, enterohemorrhagic *E. coli*, enteroaggregative *E. coli* and uropathogenic *E. coli*) *Enterococcus* sp. (such as *Enterococcus faecalis* and *Enterococcus faecium*) *Ehrlichia* sp. (such as *Ehrlichia chafeensia* and *Ehrlichia canis*), *Erysipelothrix rhusiopathiae, Eubacterium* sp., *Francisella tularensis, Fusobacterium nucleaturn, Gardnerella vaginalis, Gemella morbillorum, Haemophilus* sp. (such as *Haemophilus influenzae, Haemophilus ducreyi, Haemophilus aegyptius, Haemophilus parainfluenzae, Haemophilus haemolyticus* and *Haemophilus parahaemolyticus, Helicobacter* sp. (such as *Helicobacter pylori, Helicobacter cinaedi* and *Helicobacter fennelliae*), *Kingella kingii, Klebsiella* sp. (such as *Klebsiella pneumoniae, Klebsiella granulomatis* and *Klebsiella oxytoca*), *Lactobacillus* sp., *Listeria monocytogenes, Leptospira interrogans, Legionella pneumophila, Leptospira interrogans, Peptostreptococcus* sp., *Moraxella catarrhalis, Morganella* sp., *Mobiluncus* sp., *Micrococcus* sp., *Mycoplasm* sp. (such as *Mycoplasma pneumoniae, Mycoplasma hominis*, and *Mycoplasma genitalium*), *Nocardia* sp. (such as *Nocardia asteroides, Nocardia cyriacigeorgica* and *Nocardia brasiliensis*), *Neisseria* sp. (such as *Neisseria gonorrhoeae* and *Neisseria meningitidis*), *Pasteurella multocida, Plesiomonas shigelloides. Prevotella* sp., *Porphyromonas* sp., *Prevotella melaminogenica, Proteus* sp. (such as *Proteus vulgaris* and *Proteus mirabilis*), *Providencia* sp. (such as *Providencia alcalifaciens, Providencia rettgeri* and *Providencia stuartii*), *Pseudomonas aeruginosa, Propionibacterium acnes, Rhodococcus equi, Rickettsia* sp. (such as *Rickettsia rickettsii, Rickettsia akari* and *Rickettsia prowazekii, Orientia tsutsugamushi* (formerly: *Rickettsia tsutsugamushi*) and *Rickettsia typhi*), *Rhodococcus* sp., *Serratia marcescens, Stenotrophomonas maltophilia, Salmonella* sp. (such as *Salmonella enterica, Salmonella typhi, Salmonella paratyphi, Salmonella enteritidis, Salmonella cholerasuis* and *Salmonella typhimurium*), *Serratia* sp. (such as *Serratia marcesans* and *Serratia liquifaciens*), *Shigella* sp. (such as *Shigella dysenteriae, Shigella flexneri, Shigella boydii* and *Shigella sonnei*), *Staphylococcus* sp. (such as *Staphylococcus aureus, Staphylococcus epidermidis, Staphylococcus hemolyticus, Staphylococcus saprophyticus*), *Streptococcus* sp. (such as *Streptococcus pneumoniae* (for example chloramphenicol-resistant serotype 4 *Streptococcus pneumoniae*, spectinomycin-resistant serotype 6B *Streptococcus pneumoniae*, streptomycin-resistant serotype 9V *Streptococcus pneumoniae*, erythromycin-resistant serotype 14 *Streptococcus pneumoniae*, optochin-resistant serotype 14 *Streptococcus pneumoniae*, rifampicin-resistant serotype 18C *Streptococcus pneumoniae*, tetracycline-resistant serotype 19F *Streptococcus pneumoniae*, penicillin resistant serotype 19F *Streptococcus pneumoniae*, and trimethoprim-resistant serotype 23F *Streptococcus pneumoniae*, chloramphenicol-resistant serotype 4 *Streptococcus pneumoniae*, spectinomycin-resistant serotype 6B *Streptococcus pneumoniae*, streptomycin-resistant serotype 9V *Streptococcus pneumoniae*, optochin-resistant serotype 14 *Streptococcus pneumoniae*, rifampicin-resistant serotype 18C *Streptococcus pneumoniae*, penicillin resistant serotype 19F *Streptococcus pneumoniae*, or trimethoprim-resistant serotype 23F *Streptococcus pneumoniae*), *Streptococcus agalactiae, Streptococcus mutans, Streptococcus pyogenes*, Group A streptococci, *Streptococcus pyogenes*, Group B streptococci, *Streptococcus agalactiae*, Group C streptococci, *Streptococcus anginosus, Streptococcus equismilis*, Group D streptococci, *Streptococcus bovis*, Group F streptococci, and *Streptococcus anginosus* Group G streptococci), *Spirillum minus, Streptobacillus moniliformi, Treponema* sp. (such as *Treponema carateum, Treponema petenue, Treponema pallidum* and *Treponema endemicum, Tropheryma whippelii, Ureaplasma urealyticum, Veillonella* sp., *Vibrio* sp. (such as *Vibrio cholerae, Vibrio parahemolyticus, Vibrio vulnificus, Vibrio parahaemolyticus, Vibrio vulnificus, Vibrio alginolyticus, Vibrio mimicus, Vibrio hollisae, Vibrio fluvialis, Vibrio metchnikovii, Vibrio damsela* and *Vibrio fumisii*), *Yersinia* sp. (such as *Yersinia enterocolitica, Yersinia pestis*) and *Xanthomonas maltophilia* among others. As used herein, bacterial pathogen does not include *Mycobacterium tuberculosis*, or other bacterium that can cause tuberculosis.

Beta-lactam antibiotics: A class of antibiotic agents containing a Beta-lactam nucleus in its molecular structure. Examples of Beta-lactam antibiotics include, but are not limited to, penicillin derivatives, cephalosporins, penems, monobactams, carbapenems, Beta-lactamase inhibitors and combinations thereof. Examples of penicillin derivatives include, but are not limited to, aminopenicillins (e.g., amoxacillin, ampicillin, and epicillin); carboxypenicillins (e.g., carbenicillin, ticarcillin, and temocillin); ureidopenicillins (e.g., azlocillin, piperacillin and mezlocillin); mecillinam, sulbenicillin, benzathine penicillin, penicillin G (benzylpenicillin), penicillin V (phenoxymethylpenicillin), penicillin O (allylmercaptomethylpenicillinic), procaine penicillin, oxacillin, methicillin, nafcillin, cloxacillin, dicloxacillin, flucloxacillin, pivampicillin, hetacillin, becampicillin, metampicillin, talampicillin, co-amoxiclav (amoxacillin plus clavulanic acid), and piperacillion. Examples of cephalosporins include, but are not limited to, cephalexin, cephalothin, cefazolin, cefaclor, cefuroxime, cefamandole, cefotetan, cefoxitin, ceforanide, ceftriaxone, cefotaxime, cefpodoxime proxetil, ceftazidime, cefepime, cefoperazone, ceftizoxime, cefixime and cefpirome. Examples of penems include, without limitation, faropenem. Examples of monobactams include, without limitation, aztreonam and tigemonam. Examples of carbapenems include, but are not limited to, biapenenvdoripenem, ertapenem, -imipenem, -meropenem, -and panipenem. Examples of Beta-lactamase inhibitors include, but are not limited to, tazobactam ([2S-(2alpha,3beta,5alpha)]-3-Methyl-7-oxo-3-(1H-1,2,3-triazol-1-ylmethyl)-4-thia-1-azabicyclo[3.2.0]heptane-2-carboxylic acid 4,4-dioxide sodium salt), sulbactam (2S,5R)-3,3-dimethyl-7-oxo-4-thia-1-azabicyclo[3.2.0]heptane-2-carboxylic acid 4,4-dioxide sodium), and clavulanic acid ((2R,5R,Z)-3-(2-hydroxyethylidene)-7-oxo-4-oxa-1-aza-bicyclo[3.2.0]heptane-2-carboxylic acid).

Biological activity: An expression describing the beneficial or adverse effects of a substance on living matter. When the agent is a complex chemical mixture, this activity is exerted by the substance's active ingredient or pharmacophore, but can be modified by the other constituents. Activity is generally dosage-dependent and it is not uncommon to have effects ranging from beneficial to adverse for one substance when going from low to high doses. In one example, MSM alters, such as increase or decreases the biological activity of a microorganism, such as bacteria.

Biological sample: A biological specimen containing genomic DNA, RNA (including mRNA), protein, whole cells, cell membranes or combinations thereof, obtained from a subject. Examples include, but are not limited to, mucus, peripheral blood, urine, saliva, tissue biopsy, needle aspirates, surgical specimen, amniocentesis samples and autopsy material. In one example, a sample includes a tissue biopsy obtained from a subject with a bacterial infection, such as MRSA or *Staphylococcus aureus* infection. In another example, a sample includes a mucus sample obtained from a subject with a bacterial infection of the lungs, such as MRSA or *Staphylococcus aureus* infection.

Composition (or formulation): A chemical compound or mixture of compounds capable of inducing a desired effect when properly administered. Compositions typically include at least one agent. An industrial composition is a chemical compound or composition capable of inducing a desired effect when properly administered to a surface. A pharmaceutical composition is a chemical compound or composition capable of inducing a desired therapeutic or prophylactic effect when properly administered to a subject, or a cell. In many instances, an industrial composition could also be administered to a subject. In many instances, a pharmaceutical composition could also be administered to a surface. In a particular example, a composition includes an agent or agents that inhibit a drug resistant bacterial pathogen. For example, a composition can include MSM and an anti-microbial agent. In some embodiments, a composition includes MSM and methicillin or oxacillin. Some embodiments provide compositions that include MSM without DMSO.

Contacting: Placement in direct physical association; including in solid, liquid and gas form. Contacting includes contact between one molecule and another molecule. Contacting can occur in vitro with isolated cells or tissue or in vivo by administering to a subject.

Control: Samples believed to be normal (e.g., representative activity or function in the absence of the variable being tested) as well as laboratory values, even though possibly arbitrarily set, keeping in mind that such values can vary from laboratory to laboratory. A control group is practically identical to the treatment group, except for the single variable of interest whose effect is being tested, which is only applied to the treatment group.

Decrease or Inhibit: To reduce the quality, amount, or strength of something. In one example, administration of MSM decreases or reduces one or more biological activities, such as growth, reproduction, proliferation, survival rate, metabolism, vitality, robustness, action, and/or function of microorganisms by at least 10%, at least 20%, at least 50%, or even at least 90%, including between 10% to 95%, 20% to 80%, 30% to 70%, 40% to 50%, such as 10%, 20%, 30%, 40%, 50%, 60%, 70%, 80%, 85%, 90%, 95%, 98%, or 100%. Such decreases can be measured using the methods disclosed herein as well as those known to one of ordinary skill in the art. In some embodiments, MSM is used to inhibit survival of specific microorganisms. In some embodiments, log-scale reductions are realized after the first 24 hours.

Dimethyl sulfoxide (DMSO): Dimethyl sulfoxide (DMSO), also known as methylsulfonylmethane or methyl sulfoxide, is an organosulfur compound with the formula $(CH_3)_2SO$. This colorless liquid is a polar aprotic solvent that dissolves both polar and nonpolar compounds and is miscible in a wide range of organic solvents as well as water. It has a distinctive property of penetrating the skin very readily, so that one may taste it soon after it comes into contact with the skin. DMSO is well known as a nutritional supplement and as a pharmaceutical agent. One of skill in the relevant art will be familiar with these uses. Various grades of DMSO are available commercially (for example, product No. 472301 from Sigma-Aldrich, Corp., St. Louis, Mo.) and one of skill in the art will be familiar with a source of DMSO.

Drug resistant bacterial pathogen: This term refers to a bacterial pathogen that is resistant to one or more anti-microbial agents. Drug resistant refers to both partial and complete resistance. For example, MRSA is a drug resistant bacterial pathogen that is resistant to Beta-lactam antibiotics. A bacterial pathogen may be both drug resistant and drug-sensitive if it is sensitive to one anti-microbial agent, but resistant to another. As used herein, a subject contacting a drug resistant bacterial pathogen is a subject with a drug resistant bacterial infection. As used herein, drug resistant bacterial pathogen does not include drug resistant *Mycobacterium tuberculosis*, or other drug resistant bacterial pathogen that can cause tuberculosis.

Drug sensitive bacterial pathogen: This term refers to a bacterial pathogen that is sensitive to one or more anti-microbial agents. A bacterial pathogen may be both drug resistant and drug-sensitive if it is sensitive to one anti-microbial agent, but resistant to another. In some embodiments, a bacterial pathogen resistant to a particular anti-microbial agent may be rendered sensitive to that agent if the bacterial pathogen is contacted with MSM. As used herein, a subject contacting a drug-sensitive bacterial pathogen is a subject with a drug-sensitive bacterial infection. As used herein, drug sensitive bacterial pathogen does not include drug sensitive *Mycobacterium tuberculosis*, or other drug sensitive bacterial pathogen that can cause tuberculosis.

Enhance or Increase: To increase the quality, amount, or strength of something.

Fungal pathogen: A fungus that causes disease. Examples of fungal pathogens for which MSM can be used to modify include without limitation any one or more of (or any combination of) *Trichophyton rubrum, T. mentagrophytes, Epidermophyton floccosum, Microsporum canis, Pityrosporum orbiculare* (*Malassezia furfur*), *Candida* sp. (such as *Candida albicans*), *Aspergillus* sp. (such as *Aspergillus fumigatus, Aspergillus flavus, Aspergillus glaucus, Aspergillus nidulans, Aspergillus oryzae, Aspergillus terreus, Aspergillus ustus, Aspergillus versicolor* and *Aspergillus clavatus*), *Cryptococcus* sp. (such as *Cryptococcus neoformans, Cryptococcus gattii, Cryptococcus laurentii* and *Cryptococcus albidus*), *Coccidioides* sp., *Histoplasma* sp. (such as *Histoplasma capsulatum*), *Pneumocystis* sp. (such as *Pneumocystis jirovecii*), *Stachybotrys* sp. (such as *Stachybotrys chartarum*), Paracoccidioides, Blastomyce, Fusarium, Sporothrix, Trichosporon, Rhizopus, Pseudallescheria, Paecilomyces, Alternaria, Curvularia, Exophiala, Wangiella, Penicillium, and Cephalosphorium. In some embodiments, MSM is administered to inhibit or prevent an infection or disorder associated with one or more of the aforementioned fungal pathogens.

Incubating: A term that includes a sufficient amount of time for an agent, such as MSM, to interact with something, such as a cell or tissue.

Inhalant device: A device capable of delivering a composition to a subject, for example to a subject's lung tissue. For example, an inhalant device may be an inhaler, a nebulizer or a ventilator. Inhalant devices described herein are constructed from a material adapted for contacting DMSO and/or MSM. In some embodiments, an inhalant device is disposable or replaceable. Inhalant devices described herein are configured to deliver a DMSO or MSM containing composition to directly contact bacterial pathogens in a subject's lung tissue. Inhalant devices are configured to generate particles of a composition that range in size. In some embodiments, an inhalant device is configured to generate particles of a composition that range in size from about 0.1 µm to about 10 µm or from about 0.5 µm to about 5 µm.

Inhibit or Treating an Infection or Disease: Inhibiting the full development of an infection, disease or condition, for example, in a subject who is at risk for developing an infection, such as a bacterial infection. "Treatment" refers to a therapeutic intervention that ameliorates a sign or symptom of a disease or pathological condition after it has begun to develop. As used herein, the term "ameliorating," with reference to a disease, pathological condition or symptom, refers to any observable beneficial effect of the treatment. The beneficial effect can be evidenced, for example, by a delayed onset of clinical symptoms of the infection/disease in a susceptible subject, a reduction in severity of some or all clinical symptoms of the infection/disease, a slower progression of the infection/disease, a reduction in the number of relapses of the infection/disease, an improvement in the overall health or well-being of the subject, or by other parameters well known in the art that are specific to the particular infection/disease, such as a particular bacterial infection.

Methicillin resistant *Staphylococcus aureus* (MRSA): A *Staphylococcus aureus* bacteria having full or partial (or intermediate) resistance to one or more Beta-lactam antibiotics. MRSA is also called multidrug resistant *Staphylococcus aureus* (MDSA), oxacillin-resistant *Staphylococcus aureus* (ORSA) or "Golden Staph." In some embodiments, contacting a MRSA with MSM renders the MRSA sensitive to a Beta-lactam antibiotic that it was resistant to prior to contact with MSM. Using the Etest® system for determining antibiotic sensitivity, MRSA shows a MIC of at least 2 µg/ml for oxacillin (see, e.g., the Etest® technical manual, AB bioMérieux, 2008).

Methylsulfonylmethane (MSM): An organosulfur compound with the formula $(CH_3)_2SO_2$. MSM is also known as $DMSO_2$, dimethyl sulfone, methyl sulfone and sulfonylbismethane. MSM has largely been marketed and sold as a dietary supplement.

MSM is structurally related to dimethyl sulfoxide (DMSO), but the behavior of these two is different. DMSO is a highly polar solvent and an excellent ligand, with water-like dissolving properties whereas MSM is less polar and less reactive. MSM is also a metabolite of DMSO. MSM has the following chemical structure:

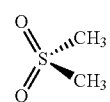

Microorganism: A member of the prokaryotic or eukaryotic microbial species from the domains Archaea, Bacteria, and Eucarya, the latter including yeast and filamentous fungi, protozoa, algae, or higher Protista. The terms "microbial cells" and "microbes" are used interchangeably with the term microorganism.

Minimum inhibitory concentration (MIC): The lowest concentration of an antimicrobial that will inhibit the visible growth of a microorganism after overnight incubation. Minimum inhibitory concentrations are important in diagnostic laboratories to confirm resistance of microorganisms to an antimicrobial agent and also to monitor the activity of new antimicrobial agents.

Modulate or modulating: To adjust, alter, regulate an activity, a degree or rate of such including an increase or a decrease in biological activity of a molecule. In one example, MSM is administered to modulate bacterial sensitivity to anti-microbial agents.

Parasite: An organism that lives inside humans or other organisms acting as hosts (for the parasite). Parasites are dependent on their hosts for at least part of their life cycle. Parasites are harmful to humans because they consume needed food, eat away body tissues and cells, and eliminate toxic waste, which makes people sick. Examples of fungal pathogens for use in accordance with the disclosed methods and compositions include without limitation any one or more of (or any combination of) Malaria (*Plasmodium falciparum, P. vivax, P. malariae*), Schistosomes, Trypanosomes, *Leishmania*, Filarial nematodes, Trichomoniasis, Sarcosporidiasis, *Taenia* (*T. saginata, T. solium*), *Leishmania, Toxoplasma gondii*, Trichinelosis (*Trichinella spiralis*) or Coccidiosis (*Eimeria* species). MSM may be used to inhibit or prevent activity of one or more of the organisms listed above.

Pharmaceutically acceptable carriers or vehicles: The pharmaceutically acceptable carriers (vehicles) useful in this disclosure are conventional. *Remington's Pharmaceutical Sciences*, by E. W. Martin, Mack Publishing Co., Easton, Pa., 19th Edition (1995), describes compositions and compositions suitable for pharmaceutical delivery of one or more therapeutic compounds or molecules, such as one or more peptides provided herein. In general, the nature of the carrier will depend on the particular mode of administration being employed. For instance, parenteral compositions usually comprise injectable fluids that include pharmaceutically and physiologically acceptable fluids such as water, physiological saline, balanced salt solutions, aqueous dextrose, glycerol or the like as a vehicle. In a particular embodiment the carrier is one that allows the therapeutic compound to cross the dermal layer. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, compositions to be administered can contain minor amounts of non-toxic auxiliary substances, such as wetting or emulsifying agents, preservatives, and pH buffering agents and the like, for example sodium acetate or sorbitan monolaurate.

Quantitating: Determining or measuring a quantity (such as a relative quantity) of a molecule or the activity of a molecule, such as the quantity of analyte present in a sample.

Sensitizing a drug resistant microorganism: Any means of decreasing the drug-resistance of a microorganism, including bacterial pathogens. This includes modifications to the microorganism, as well as, use of an agent that increases the effectiveness of another agent for inhibiting the microorganism. For example, sensitizing MRSA to methicillin includes modulating a MRSA such that it is no longer resistant to methicillin, as well as, contacting the MRSA with an agent that reduces the resistance of the MRSA to methicillin, for example, contacting the MRSA with MSM.

*Staphylococcus aureus*: A Gram-positive coccus with round cells, approximately 1 µm in diameter, which form grape-like clusters indicative of the ability to divide in more than one plane. They are capable of both aerobic and anaerobic respiration and most strains ferment mannitol anaerobically. On blood agar they form characteristic golden or white colonies. They produce catalase, coagulase and an extracellular cell clumping factor, and some strains produce capsules (see Brown et al., *J. Antimicrob. Chemother.*, 56: 1000-1018, 2005).

Subject: Living multi-cellular vertebrate organisms, a category that includes human and non-human mammals. "In a subject" refers to substances or microorganisms (e.g., bacterial pathogens) that are contacting a subject or in physical connection with a subject.

Subject susceptible to a disease or condition: A subject capable of, prone to, or predisposed to developing a disease or condition. It is understood that a subject already having or showing symptoms of a disease or condition is considered "susceptible" since they have already developed it.

Surface: The outer layer of a physical object.

Symptom and sign: Any subjective evidence of disease or of a subject's condition, e.g., such evidence as perceived by the subject; a noticeable change in a subject's condition indicative of some bodily or mental state. A "sign" is any abnormality indicative of disease, discoverable on examination or assessment of a subject. A sign is generally an objective indication of disease. Signs include, but are not limited to any measurable parameters such as tests for detecting a disorder or disease, such as a bacterial or viral infection. In one example, reducing or inhibiting one or more symptoms or signs associated with a bacterial or viral infection, includes reducing or inhibiting bacterial survival or viral infection by a desired amount, for example by at least 20%, at least 50%, at least 60%, at least 70%, at least 80%, at least 90%, at least 95%, at least 98%, or even at least 100%, as compared to the bacterial survival or viral infectivity in the absence of MSM.

Therapeutically effective amount or concentration: An amount of a composition that alone, or together with an additional agent(s) is sufficient to achieve a desired effect in a subject, or cell, or on a surface, to which the composition is administered. The effective amount of an agent or composition will be dependent on several factors, including, but not limited to the subject, cells or surface to which the agent or composition is administered, and the manner of administration. In one example, a therapeutically effective amount or concentration is one that is sufficient to inhibit a bacterial pathogen, for example a drug resistant bacterial pathogen such as MRSA.

In one example, a desired effect is to reduce or inhibit one or more symptoms associated with a disease. For example symptoms associated with MRSA infection. The one or more symptoms do not have to be completely eliminated for the composition or agent to be effective. For example, a composition or agent can decrease the sign or symptom by a desired amount, for example by at least 20%, at least 50%, at least 80%, at least 90%, at least 95%, at least 98%, or even at least 100%, as compared to the sign or symptom in the absence of the composition or agent. In one example, a desired effect is to reduce or inhibit a microorganism (such as survival of the microorganism) by a desired amount, for example by at least 20%, at least 50%, at least 60%, at least 70%, at least 80%, at least 90%, at least 95%, at least 98%, or even at least 100%, as compared to microorganism survival in the absence of the composition or agent. In another example, a desired effect is to sensitize a drug resistant microorganism to the drug the microorganism is resistant to by a desired amount, for example by at least 20%, at least 50%, at least 60%, at least 70%, at least 80%, at least 90%, at least 95%, at least 98%, or even at least 100%, as compared to sensitivity of the microorganism to the drug in the absence of the composition or agent.

A therapeutically effective amount of a disclosed composition or agent can be administered in a single dose, or in several doses, for example daily, during a course of treatment. However, the therapeutically effective amount can depend on the subject or cell or surface to which the composition or agent is administered, the severity and type of the condition being treated, and the manner of administration. A therapeutically effective amount of an agent or composition can be measured as the concentration (moles per liter or molar-M or weight per volume or other concentration measurement) of the agent or composition in blood (in vivo) or buffer (in vitro), among others, that produces the desired effect(s). Alternatively, a therapeutically effective amount of an agent or composition can be measured as the amount administered to a subject per body weight of the subject, for example, mg agent/kg body weight.

Untreated cell: A cell that has not been contacted with a desired agent, such as MSM. In an example, an untreated cell is a cell that receives the vehicle in which MSM was delivered.

Virus: A microscopic infectious organism that reproduces inside living cells. A virus consists essentially of a core of nucleic acid surrounded by a protein coat, and has the ability to replicate only inside a living cell. "Viral replication" is the production of additional virus by the occurrence of at least one viral life cycle. A virus may subvert the host cells' normal functions, causing the cell to behave in a manner determined by the virus. For example, a viral infection may result in a cell producing a cytokine, or responding to a cytokine, when the uninfected cell does not normally do so. In some examples, a virus is a pathogen.

Specific examples of viral pathogens that might be treated in accordance with the disclosed methods and compositions include without limitation any one or more of (or any combination of); Arenaviruses (such as Guanarito virus, Lassa virus, Junin virus, Machupo virus and Sabia), Arteriviruses, Roniviruses, Astroviruses, Bunyaviruses (such as Crimean-Congo hemorrhagic fever virus and Hantavirus), Barnaviruses, Birnaviruses, Bornaviruses (such as Borna disease virus), Bromoviruses, Caliciviruses, Chrysoviruses, Coronaviruses (such as Coronavirus and SARS), Cystoviruses, Closteroviruses, Comoviruses, Dicistroviruses, Flaviruses (such as Yellow fever virus, West Nile virus, Hepatitis C virus, and Dengue fever virus), Filoviruses (such as Ebola virus and Marburg virus), Flexiviruses, Hepeviruses (such as Hepatitis E virus), human adenoviruses (such as human adenovirus A-F), human astroviruses, human BK polyomaviruses, human bocaviruses, human coronavirus (such as a human coronavirus HKU1, NL63, and OC43), human enteroviruses (such as human enterovirus A-D), human erythrovirus V9, human foamy viruses, human herpesviruses (such as human herpesvirus 1 (herpes simplex virus type 1), human herpesvirus 2 (herpes simplex virus type 2), human herpesvirus 3 (Varicella zoster virus), human herpesvirus 4 type 1 (Epstein-Barr virus type 1), human herpesvirus 4 type 2 (Epstein-Barr virus type 2), human herpesvirus 5 strain AD169, human herpesvirus 5 strain Merlin Strain, human herpesvirus 6A, human herpesvirus 6B, human herpesvirus 7, human herpesvirus 8 type M, human herpesvirus 8 type P and Human Cyotmegalovirus), human immunodeficiency viruses (HIV) (such as HIV 1 and HIV 2), human metapneumoviruses, human papillomaviruses (such as human papillomavirus-1, human papillomavirus-18, human papillomavirus-2, human papillomavirus-54, human papillomavirus-61, human papillomavirus-cand90, human papillomavirus RTR7, human papillomavirus type 10, human papillomavirus type 101, human papillomavirus type 103, human papillomavirus type 107, human papillomavirus type 16, human papillomavirus type 24, human papillomavirus type 26, human papillomavirus type 32, human papillomavirus type 34, human papillomavirus type 4, human papillomavirus type 41, human papillomavirus type 48, human papillomavirus type 49, human papillomavirus type 5, human papillomavirus type 50, human papillomavirus type 53, human papillomavirus type 60, human papillomavirus type 63, human papillomavirus type 6b, human papillomavirus type 7, human papillomavirus type 71, human papillomavirus type 9, human papillomavirus type 92, and human papillomavirus type 96), human parainfluenza viruses (such as human parainfluenza virus 1-3), human parechoviruses, human parvoviruses (such as human parvovirus 4 and human parvovirus B19), human respiratory syncytial viruses, human rhinoviruses (such as human rhinovirus A and human rhinovirus B), human spumaretroviruses, human T-lymphotropic viruses (such as human T-lymphotropic virus 1 and human T-lymphotropic virus 2), Human polyoma viruses, Hypoviruses, Leviviruses, Luteoviruses, Lymphocytic choriomeningitis viruses (LCM), Marnaviruses, Narnaviruses, Nidovirales, Nodaviruses, Orthomyxoviruses (such as Influenza viruses), Partitiviruses, Paramyxoviruses (such as Measles virus and Mumps virus), Picornaviruses (such as Poliovirus, the common cold virus, and Hepatitis A virus), Potyviruses, Poxviruses (such as Variola and Cowpox), Sequiviruses, Reoviruses (such as Rotavirus), Rhabdoviruses (such as Rabies virus), Rhabdoviruses (such as Vesicular stomatitis virus, Tetraviruses, Togaviruses (such as Rubella virus and Ross River virus), Tombusviruses, Totiviruses, Tymoviruses, and Noroviruses among others.

In some embodiments, MSM is used to inhibit a biological activity of one or more of the viruses listed above.

Yeast: An eukaryotic microorganism classified in the Kingdom Fungi, with about 1,500 species described. Most reproduce asexually by budding, although a few reproduce by binary fission. Yeasts generally are unicellular, although some species may become multicellular through the formation of a string of connected budding cells known as pseudohyphae, or false hyphae. Exemplary yeasts that can be used in the disclosed methods and compositions include but are not limited to *Saccharomyces cerevisiae, Candida albicans, Schizosaccharomyces pombe, Pichia, Cryptococcus, Zygosaccharomyces, Torulopsis, Hansenula,* and *Debaryomyces.*

II. Overview of Several Embodiments

Provided herein is a method of inhibiting a drug resistant bacterial pathogen, which method involves selecting a drug resistant bacterial pathogen; and contacting the bacterial pathogen with a composition comprising a therapeutically effective amount of MSM and a therapeutically effective amount of an agent that inhibits the drug-sensitive form of the drug resistant bacterial pathogen, thereby inhibiting a drug resistant bacterial pathogen. In some embodiments, the drug resistant bacterial pathogen is MRSA.

Also provided is a method of sensitizing a drug resistant bacterial pathogen to a drug the bacterial pathogen is resistant to, which method comprises selecting a drug resistant bacterial pathogen; and contacting the bacterial pathogen with a composition comprising a therapeutically effective amount of MSM, thereby sensitizing the drug resistant bacterial pathogen to the drug the bacterial pathogen is resistant to. In some embodiments, the drug resistant bacterial pathogen is MRSA.

Also provided herein is a method of inhibiting a drug-sensitive bacterial pathogen from developing drug resistance, which method comprises selecting a drug sensitive bacterial pathogen; and contacting the drug-sensitive bacterial pathogen with a composition comprising a therapeutically effective amount of MSM and a therapeutically effective amount of an agent that inhibits the drug-sensitive bacterial pathogen, thereby inhibiting the drug-sensitive bacterial pathogen from developing drug resistance. In some embodiments, the drug sensitive bacterial pathogen is *Staphylococcus aureus*.

In various embodiments of the methods described herein, the agent is a Beta-lactam antibiotic. In some embodiments, the agent comprises penicillin derivatives, cephalosporins, penems, monobactams, carbapenems, Beta-lactamase inhibitors or combinations thereof. In some embodiments, the agent comprises methicillin or oxacillin. In various embodiments the therapeutically effective amount of an agent comprises about 1-5, 5-10, 10-20, 20-30, 30-40, 40-50, 50-60, 60-70, 70-80, 80-90 or about 90-100 MIC of a Beta-lactam antibiotic. In some embodiments, the therapeutically effective amount of an agent comprises about 0.001, 0.01, 0.1, 0.5 or 1 MIC of a Beta-lactam antibiotic.

In various embodiments of the methods described herein, the bacterial pathogen is in a subject. In some embodiments, the bacterial pathogen is on a surface.

In various embodiments, the effective amount of MSM is about 5-20% MSM, about 5-16% MSM, about 5-10% MSM, about 5-8% MSM, about 9-16% MSM or about 10-15% MSM. MSM (weight percent of the composition comprising MSM). In other embodiments, the effective amount of MSM is about 5, 6, 7, 8, 9, 10, 11, 12, 13, 14, 15 or 16% MSM. In still other embodiments, the effective amount of MSM is about 10-16% MSM.

In various embodiments, the bacterial pathogen is contacted with the composition for about 24, 36, 48, 60, 72, 84, 96, 108 or 120 hours.

In some embodiments, the composition is administered topically or with an inhalant device. In some embodiments, the composition comprises 0-5% sodium chloride.

For instance, in one particular embodiment of a method of inhibiting a drug resistant bacterial pathogen, the bacterial pathogen is MRSA, the agent is a Beta-lactam antibiotic, the effective amount of MSM is about 5-10% MSM and the composition is administered topically.

For instance, in one particular embodiment of method of sensitizing a drug resistant bacterial pathogen to a drug the bacterial pathogen is resistant to, the bacterial pathogen is MRSA, the effective amount of MSM is about 5-10% MSM and the composition is administered topically.

For instance, in one particular embodiment of a method of inhibiting a drug-sensitive bacterial pathogen from developing drug resistance, the bacterial pathogen is *Staphylococcus aureus*, the agent is a Beta-lactam antibiotic, the effective amount of MSM is about 5-10% MSM and the composition is administered topically.

It will be further understood that the methods of sensitizing or inhibiting bacterial pathogens disclosed herein are useful beyond the specific circumstances that are described in detail herein, and for instance are expected to be useful for any number of conditions wherein a bacterial pathogen has become drug resistant or where it is desirable to inhibit a drug sensitive bacterial pathogen from becoming drug resistant.

III. MSM

MSM is an organosulfur compound with the formula $(CH_3)_2SO_2$. MSM is structurally related to dimethyl sulfoxide (DMSO), but the behavior of these two is different. DMSO is a highly polar solvent and an excellent ligand, with water-like dissolving properties whereas MSM is less polar and less reactive. MSM is well known as a nutritional supplement and as a pharmaceutical agent (see, e.g., Jacob and Appleton, MSM; the definitive guide: A comprehensive review of the science and therapeutics of Methylsulfonylmethane, Topanga, Calif.: Freedom Press, 2003). MSM is also known to be useful for the treatment of osteoarthritis (Kim et al., *Osteoarthritis Cartilage*, 14:286-94, 2006) and hay fever (Barrager et al., *J. Altern. Complement. Med.*, 8:167-74, 2002). One of skill in the relevant art will be familiar with these uses. Various grades of MSM are available commercially (for example, OptiMSM® sold by Bergstrom Nutrition, Corp., Vancouver, Wash.); one of skill in the art will be familiar with a source of MSM. MSM is highly water soluble. At room temperature, aqueous solutions of 20% MSM can be prepared easily. Aqueous solutions of higher MSM concentrations are possible at temperatures elevated over room temperature.

IV. DMSO

Dimethyl sulfoxide (DMSO) is an organosulfur compound with the formula $(CH_3)_2SO$. This colorless liquid is a polar aprotic solvent that dissolves both polar and nonpolar compounds and is miscible in a wide range of organic solvents as well as water. It has a distinctive property of penetrating the skin very readily, so that one may taste it soon after it comes into contact with the skin. DMSO is well known as a nutritional supplement and as a pharmaceutical agent. One of skill in the relevant art will be familiar with these uses. Various grades of DMSO are available commercially (for example, product No. 472301 from Sigma-Aldrich, Corp., St. Louis, Mo.) and one of skill in the art will be familiar with a source of DMSO.

V. Beta-Lactam Antibiotics

Beta-lactam antibiotics are a broad class of antibiotic agents, consisting of all antibiotic agents containing a Beta-lactam nucleus in their molecular structure. This class of antibiotics is the most widely used group of antibiotics; one of skill in the relevant art will understand how to choose an appropriate Beta-lactam antibiotic for use to inhibit or treat a bacterium.

Examples of Beta-lactam antibiotics include, but are not limited to, penicillin derivatives, cephalosporins, penems, monobactams, carbapenems, Beta-lactamase inhibitors and combinations thereof. Examples of penicillin derivatives include, but are not limited to, aminopenicillins (e.g., amoxacillin, ampicillin, and epicillin); carboxypenicillins (e.g., carbenicillin, ticarcillin, and temocillin); ureidopenicillins (e.g., azlocillin, piperacillin and mezlocillin); mecillinam, sulbenicillin, benzathine penicillin, penicillin G (benzylpenicillin), penicillin V (phenoxymethylpenicillin), penicillin O (allylmercaptomethylpenicillinic), procaine penicillin, oxacillin, methicillin, nafcillin, cloxacillin, dicloxacillin, flucloxacillin, pivampicillin, hetacillin, becampicillin, metampicillin, talampicillin, co-amoxiclav (amoxacillin plus clavulanic acid), and piperacillion. Examples of cephalosporins include, but are not limited to, cephalexin, cephalothin, cefazolin, cefaclor, cefuroxime, cefamandole, cefotetan, cefoxitin, ceforanide, ceftriaxone, cefotaxime, cefpodoxime proxetil, ceftazidime, cefepime, cefoperazone, ceftizoxime, cefixime and cefpirome. Examples of penems include, without limitation, faropenem. Examples of monobactams include, without limitation, aztreonam and tigemonam. Examples of carbapenems include, but are not limited to, biapenenvdoripenem, ertapenem, -imipenem, -meropenem, -and panipenem. Examples of Beta-lactamase inhibitors include, but are not limited to, tazobactam ([2S-(2alpha, 3beta,5alpha)]-3-Methyl-7-oxo-3-(1H-1,2,3-triazol-1-ylmethyl)-4-thia-1-azabicyclo[3.2.0]heptane-2-carboxylic acid 4,4-dioxide sodium salt), sulbactam (2S,5R)-3,3-dimethyl-7-oxo-4-thia-1-azabicyclo[3.2.0]heptane-2-carboxylic acid 4,4-dioxide sodium), and clavulanic acid ((2R,5R,Z)-3-(2-hydroxyethylidene)-7-oxo-4-oxa-1-aza-bicyclo[3.2.0]heptane-2-carboxylic acid). These antibiotics are available commercially and one of skill in the art will be familiar with a source of each of the antibiotics disclosed herein.

Beta-lactam antibiotics are bactericidal, and act by inhibiting the synthesis of the peptidoglycan layer of bacterial cell walls. These antibiotics act by irreversibly binding to penicillin-binding proteins (PBPs); this binding disrupts cell wall synthesis, preventing cell division.

All Beta-lactam antibiotics have a Beta-lactam ring in their structure. The effectiveness of these antibiotics relies on their ability to reach the PBP intact and their ability to bind to the PBP. Hence, there are two main modes of bacterial resistance to Beta-lactams.

First, bacteria sometimes develop resistance to Beta-lactam antibiotics by synthesizing Beta-lactamase, an enzyme that attacks the Beta-lactam ring. If the bacterium produces the enzyme Beta-lactamase (or the enzyme penicillinase), the enzyme will break open the Beta-lactam ring of the antibiotic, rendering the antibiotic ineffective. The genes encoding these enzymes may be inherently present on the bacterial chromosome or may be acquired via plasmid transfer (plasmid mediated resistance), and Beta-lactamase gene expression may be induced by exposure to Beta-lactams. The production of a Beta-lactamase by a bacterium does not necessarily rule out all treatment options with Beta-lactam antibiotics. For example, to overcome this type of resistance, Beta-lactam antibiotics are often given with Beta-lactamase inhibitors such as clavulanic acid. However, in all cases where infection with Beta-lactamase-producing bacteria is suspected, the choice of a suitable Beta-lactam antibiotic should be carefully considered prior to treatment. In particular, choosing appropriate Beta-lactam antibiotic therapy is of upmost importance against organisms with inducible Beta-lactamase expression. If Beta-lactamase production is inducible, then failure to use the most appropriate Beta-lactam antibiotic therapy at the onset of treatment will result in induction of Beta-lactamase production, thereby making further efforts with other Beta-lactam antibiotics more difficult.

Second, a bacterium may express an altered PBP, to which Beta-lactams cannot bind as effectively as an unaltered PBP. As a result, the Beta-lactams are less effective at disrupting cell wall synthesis. Notable examples of this mode of resistance include penicillin-resistant *Streptococcus pneumoniae* and MRSA.

VI. MRSA

Methicillin resistant *Staphylococcus aureus* (MRSA) is a *Staphylococcus aureus* bacteria having resistance to one or more Beta-lactam antibiotics. The level of resistance to Beta-lactam antibiotic can vary depending on the strain of MRSA. For example, a particular MRSA strain may exhibit complete or partial resistance to a Beta-lactam antibiotic.

The Beta-lactam antibiotic resistance of *Staphylococcus aureus* bacteria is generally due to expression of an altered PBP, such as PBP2a or PBP2', which has low affinity for Beta-lactam antibiotics and can function in place of the native PBP. PBP2a is encoded by the mecA gene (see Brown et al., *J. Antimicrob. Chemother.*, 56: 1000-1018, 2005). Additional genes, which are also found in susceptible isolates, can affect the expression of methicillin resistance in *Staphylococcus aureus*, resulting in heterogeneity of resistance (see Brown et al., *J. Antimicrob. Chemother.*, 56: 1000-1018, 2005).

MRSA infection is caused by a *Staphylococcus aureus* bacteria having full or partial resistance to one or more Beta-lactam antibiotics. *Staphylococcus aureus* most commonly colonizes the anterior nares (the nostrils), although the respiratory tract, opened wounds, intravenous catheters, and urinary tract are also potential sites for infection. Healthy individuals may carry MRSA asymptomatically for periods ranging from a few weeks to many years. Patients with compromised immune systems are at a significantly greater risk of symptomatic secondary infection.

MRSA may progress substantially within 24-48 hours of initial symptoms, including initial topical symptoms. After 72 hours, MRSA can take hold in human tissues and eventually become resistant to treatment. Topically, the initial presentation of MRSA is small red bumps that resemble pimples, spider bites, or boils that may be accompanied by fever and occasionally rashes. Within a few days the bumps become larger, more painful, and eventually open into deep, pus-filled boils.

Many strains of MRSA are known to exist, including hospital (or healthcare) associated MRSA (HA-MRSA) and community-associated MRSA (CA-MRSA). About 75 percent of CA-MRSA infections are localized to skin and soft tissue and usually can be treated effectively. However, some CA-MRSA strains display enhanced virulence, spreading more rapidly and causing illness much more severe than traditional HA-MRSA infections, and they can affect vital organs and lead to widespread infection (sepsis), toxic shock syndrome and necrotizing ("flesh-eating") pneumonia. This is thought to be due to toxins carried by CA-MRSA strains It is not known why some healthy people develop CA-MRSA skin infections that are treatable whereas others infected with the same strain develop severe infections or die.

The most common manifestations of CA-MRSA are skin infections such as necrotizing fasciitis or pyomyositis (most commonly found in the tropics), necrotizing pneumonia, infective endocarditis (which affects the valves of the heart), or bone or joint infections. CA-MRSA often results in abscess formation that requires incision and drainage. Before the spread of MRSA into the community, abscesses were not considered contagious because it was assumed that infection required violation of skin integrity and the introduction of staphylococci from normal skin colonization. However, newly emerging CA-MRSA is transmissible (similar, but with very important differences) from HA-MRSA. Additionally, CA-MRSA is less likely than other forms of MRSA to cause cellulitis.

In some embodiments, compositions described herein are useful to treat, inhibit and/or sensitize MRSA. In some embodiments, compositions described herein are useful to treat, inhibit and/or sensitize MRSA in a subject. Methods of detecting MRSA and selecting subject with MRSA infection are disclosed herein.

VII. Other Drug Resistant Bacterial Pathogens

A drug resistant bacterial pathogen is a bacterial pathogen that is resistant to one or more anti-microbial agents. A bacterial pathogen may be both drug resistant and drug sensitive if it is sensitive to one anti-microbial agent, but resistant to another.

In some embodiments, a composition disclosed herein is used to treat, inhibit or sensitize a drug resistant bacterial pathogen.

In certain embodiments, compositions disclosed herein are effective to treat, inhibit or sensitize various drug resistant forms of bacterial pathogens including, but not limited to, the drug resistant form of one or more of *Acinetobacter baumanii*, *Actinobacillus* sp., *Actinomycetes*, *Actinomyces* sp. (such as *Actinomyces israelii* and *Actinomyces naeslundii*), *Aeromonas* sp. (such as *Aeromonas hydrophila*, *Aeromonas veronii biovar sobria* (*Aeromonas sobria*), and *Aeromonas caviae*), *Anaplasma phagocytophilum*, *Alcaligenes xylosoxidans*, *Acinetobacter baumanii*, *Actinobacillus actinomycetemcomitans*, *Bacillus* sp. (such as *Bacillus anthracis*, *Bacillus cereus*, *Bacillus subtilis*, *Bacillus thuringiensis*, and *Bacillus stearothermophilus*), *Bacteroides* sp. (such as *Bacteroides fragilis*), *Bartonella* sp. (such as *Bartonella bacilliformis* and *Bartonella henselae*, *Bifidobacterium* sp., *Bordetella* sp. (such as *Bordetella pertussis*, *Bordetella parapertussis*, and *Bordetella bronchiseptica*), *Borrelia* sp. (such as *Borrelia recurrentis*, and *Borrelia burgdorferi*), *Brucella* sp. (such as *Brucella abortus*, *Brucella canis*, *Brucella melintensis* and *Brucella suis*), *Burkholderia* sp. (such as *Burkholderia pseudomallei* and *Burkholderia cepacia*), *Campylobacter* sp. (such as *Campylobacter jejuni*, *Campylobacter coli*, *Campylobacter lari* and *Campylobacter fetus*), *Capnocytophaga* sp., *Cardiobacterium hominis*, *Chlamydia trachomatis*, *Chlamydophila pneumoniae*, *Chlamydophila psittaci*, *Citrobacter* sp. *Coxiella burnetii*, *Corynebacterium* sp. (such as, *Corynebacterium diphtheriae*, *Corynebacterium jeikeum* and *Corynebacterium*), *Clostridium* sp. (such as *Clostridium perfringens*, *Clostridium difficile*, *Clostridium botulinum* and *Clostridium tetani*), *Eikenella corrodens*, *Enterobacter* sp. (such as *Enterobacter aerogenes*, *Enterobacter agglomerans*, *Enterobacter cloacae* and *Escherichia coli*, including opportunistic *Escherichia coli*, such as enterotoxigenic *E. coli*, enteroinvasive *E. coli*, enteropathogenic *E. coli*, enterohemorrhagic *E. coli*, enteroaggregative *E. coli* and uropathogenic *E. coli*) *Enterococcus* sp. (such as *Enterococcus faecalis* and *Enterococcus faecium*) *Ehrlichia* sp. (such as *Ehrlichia chafeensia* and *Ehrlichia canis*), *Erysipelothrix rhusiopathiae*, *Eubacterium* sp., *Francisella tularensis*, *Fusobacterium nucleaturn*, *Gardnerella vaginalis*, *Gemella morbillorum*, *Haemophilus* sp. (such as *Haemophilus influenzae*, *Haemophilus ducreyi*, *Haemophilus aegyptius*, *Haemophilus parainfluenzae*, *Haemophilus haemolyticus* and *Haemophilus parahaemolyticus*, *Helicobacter* sp. (such as *Helicobacter pylori*, *Helicobacter cinaedi* and *Helicobacter fennelliae*), *Kingella kingii*, *Klebsiella* sp. (such as *Klebsiella pneumoniae*, *Klebsiella granulomatis* and *Klebsiella oxytoca*), *Lactobacillus* sp., *Listeria monocytogenes*, *Leptospira interrogans*, *Legionella pneumophila*, *Leptospira interrogans*, *Peptostreptococcus* sp., *Moraxella catarrhalis*, *Morganella* sp., *Mobiluncus* sp., *Micrococcus* sp., *Mycoplasm* sp. (such as *Mycoplasma pneumoniae*, *Mycoplasma hominis*, and *Mycoplasma genitalium*), *Nocardia* sp. (such as *Nocardia asteroides*, *Nocardia cyriacigeorgica* and *Nocardia brasiliensis*), *Neisseria* sp. (such as *Neisseria gonorrhoeae* and *Neisseria meningitidis*), *Pasteurella multocida*, *Plesiomonas shigelloides*. *Prevotella* sp., *Porphyromonas* sp., *Prevotella melaminogenica*, *Proteus* sp. (such as *Proteus vulgaris* and *Proteus mirabilis*), *Providencia* sp. (such as *Providencia alcalifaciens*, *Providencia rettgeri* and *Providencia stuartii*), *Pseudomonas aeruginosa*, *Propionibacterium acnes*, *Rhodococcus equi*, *Rickettsia* sp. (such as *Rickettsia rickettsii*, *Rickettsia akari* and *Rickettsia prowazekii*, *Orientia tsutsugamushi* (formerly: *Rickettsia tsutsugamushi*) and *Rickettsia typhi*), *Rhodococcus* sp., *Serratia marcescens*, *Stenotrophomonas maltophilia*, *Salmonella* sp. (such as *Salmonella enterica*, *Salmonella typhi*, *Salmonella paratyphi*, *Salmonella enteritidis*, *Salmonella cholerasuis* and *Salmonella typhimurium*), *Serratia* sp. (such as *Serratia marcesans* and *Serratia liquifaciens*), *Shigella* sp. (such as *Shigella dysenteriae*, *Shigella flexneri*, *Shigella boydii* and *Shigella sonnei*), *Staphylococcus* sp. (such as *Staphylococcus epidermidis*, *Staphylococcus hemolyticus*, *Staphylococcus saprophyticus*), *Streptococcus* sp. (such as *Streptococcus pneumoniae* (for example chloramphenicol-resistant serotype 4 *Streptococcus pneumoniae*, spectinomycin-resistant serotype 6B *Streptococcus pneumoniae*, streptomycin-resistant serotype 9V *Streptococcus pneumoniae*, erythromycin-resistant serotype 14 *Streptococcus pneumoniae*, optochin-resistant serotype 14 *Streptococcus pneumoniae*, rifampicin-resistant serotype 18C *Streptococcus pneumoniae*, tetracycline-resistant serotype 19F *Streptococcus pneumoniae*, penicillin resistant serotype 19F *Streptococcus pneumoniae*, and trimethoprim-resistant serotype 23F *Streptococcus pneumoniae*, chloramphenicol-resistant serotype 4 *Streptococcus pneumoniae*, spectinomycin-resistant serotype 6B *Streptococcus pneumoniae*, streptomycin-resistant serotype 9V *Streptococcus pneumoniae*, optochin-resistant serotype 14 *Streptococcus pneumoniae*, rifampicin-resistant serotype 18C *Streptococcus pneumoniae*, penicillin resistant serotype 19F *Streptococcus pneumoniae*, or trimethoprim-resistant serotype 23F *Streptococcus pneumoniae*), *Streptococcus agalactiae*, *Streptococcus mutans*, *Streptococcus pyogenes*, Group A streptococci, *Streptococcus pyogenes*, Group B streptococci, *Streptococcus agalactiae*, Group C streptococci, *Streptococcus anginosus*, *Streptococcus equismilis*, Group D streptococci, *Streptococcus bovis*, Group F streptococci, and *Streptococcus anginosus* Group G streptococci), *Spirillum minus*, *Streptobacillus moniliformi*, *Treponema* sp. (such as *Treponema carateum*, *Treponema petenue*, *Treponema pallidum* and *Treponema endemicum*, *Tropheryma whippelii*, *Ureaplasma urealyticum*, *Veillonella* sp., *Vibrio* sp. (such as *Vibrio cholerae*, *Vibrio parahemolyticus*, *Vibrio vulnificus*, *Vibrio parahaemolyticus*, *Vibrio vulnificus*, *Vibrio alginolyticus*, *Vibrio mimicus*, *Vibrio hollisae*, *Vibrio fluvialis*, *Vibrio metchnikovii*, *Vibrio damsela* and *Vibrio fumisii*), *Yersinia* sp. (such as *Yersinia enterocolitica*, *Yersinia pestis*) or *Xanthomonas maltophilia*, among others.

VIII. Drug Resistant Disease

In several embodiments, a composition disclosed herein is used treat, inhibit or sensitize a drug resistant infectious disease.

In some embodiments, compositions disclosed herein are effective in treating or inhibiting drug resistant, measles, tetanus, malaria, upper and lower respiratory infections, hepatitis, typhoid fever, vancomycin/glycopeptide-intermediate *Staphylococcus aureus* infection, vancomycin-resistant enterococci, MRSA, and *streptococcus pneumonia*, among others.

In other embodiments, compositions disclosed herein are effective treat, inhibit or sensitize various drug resistant forms of infectious diseases including, but not limited to, the drug resistant form of one or more of acinetobacter infection, actinomycosis, Adenovirus infection, African sleeping sickness (African trypanosomiasis), AIDS, amebiasis, anaplasmosis, Anthrax, *Arcanobacterium haemolyticum* infection, Argentine hemorrhagic fever, ascariasis, aspergillosis, astrovirus infection, babesiosis, *Bacillus cereus* infection, bacterial pneumonia, bacterial vaginosis (BV), *Bacteroides* infection, balantidiasis, *Baylisascaris* infection, BK virus infection, black piedra, *Blastocystis hominis* infection, blastomycosis, Bolivian hemorrhagic fever, *Borrelia* infection, botulism, Brazilian hemorrhagic fever, brucellosis, *Burkholderia* infection, Calicivirus infection, campylobacteriosis, candidiasis (moniliasis; thrush), cat-scratch disease, cellulitis, Chagas disease, chancroid, chickenpox, chlamydia, *Chlamydophila pneumoniae* infection, cholera, chromoblastomycosis, clonorchiasis, *clostridium difficile* infection, coccidioidomycosis, Colorado tick fever, common cold, creutzfeldt-Jacob disease, Crimean-Congo hemorrhagic fever, cryptococcosis, cryptosporidiosis, cutaneous larva migrans (CLM), cyclosporiasis, cysticercosis, cytomegalovirus infection, dengue fever, dientamoebiasis, diphtheria, diphyllobothriasis, dracunculiasis, ebola hemorrhagic fever, echinococcosis, ehrlichiosis, enterobiasis (Pinworm infection), *Enterococcus* infection, enterovirus infection, epidemic typhus, erythema infectiosum, exanthem subitum, fasciolopsiasis, fasciolosis, fatal familial insomnia (FFI), filariasis, food poisoning, free-living amebic infection, *Fusobacterium* infection, gas gangrene (*Clostridial myonecrosis*), geotrichosis, Gerstmann-Sträussler-Scheinker syndrome (GSS), giardiasis, glanders, gnathostomiasis, gonorrhea, granuloma inguinale (Donovanosis), Group A streptococcal infection, Group B streptococcal infection, *Haemophilus influenzae* infection, hand, foot and mouth disease (HFMD), Hantavirus, *Helicobacter pylori* infection, hemolytic-uremic syndrome (HUS), hemorrhagic fever with renal syndrome (HFRS), Hepatitis A, B, C, D, or E, herpes simplex, histoplasmosis, hookworm infection, human bocavirus infection, Hhman ewingii ehrlichiosis, human granulocytic anaplasmosis (HGA), human metapneumovirus infection, human monocytic ehrlichiosis, human papillomavirus (HPV) infection, human parainfluenza virus infection, or hymenolepiasis, among others.

In other embodiments, compositions disclosed herein are effective treat, inhibit or sensitize various drug resistant forms of infectious diseases including, but not limited to, the drug resistant form of one or more of Epstein-Barr Virus Infectious Mononucleosis (Mono), Influenza (flu), Isosporiasis, Kawasaki disease, Keratitis, *Kingella kingae* infection, Kuru, Lassa fever, Legionellosis, Leishmaniasis, Leprosy, Leptospirosis, Listeriosis, Lyme disease, Lymphatic filariasis, Lymphocytic choriomeningitis, Malaria, Marburg hemorrhagic fever (MHF), Measles, Melioidosis (Whitmore's disease), Meningitis, Meningococcal disease, Metagonimiasis, Microsporidiosis Microsporidia, Molluscum contagiosum (MC), Mumps, Murine typhus, Mycoplasma pneumonia, Mycetoma, Myiasis, Neonatal conjunctivitis, Onchocerciasis (River blindness), Paracoccidioidomycosis (South American blastomycosis), Paragonimiasis, Pasteurellosis, Pediculosis capitis (Head lice), Pediculosis corporis (Body lice), Pediculosis pubis (Pubic lice, Crab lice), Pelvic inflammatory disease (PID), Pertussis (Whooping cough), Plague, Pneumococcal infection, *Pneumocystis pneumonia* (PCP), Pneumonia, Poliomyelitis, Poliovirus, Primary amoebic meningoencephalitis (PAM), Progressive multifocal leukoencephalopathy, Psittacosis, Q fever, Rabies, Rat-bite fever, Respiratory syncytial virus, Rhinosporidiosis, Rhinovirus infection, Rickettsial infection, Rickettsialpox, Rift Valley fever (RVF), Rocky mountain spotted fever (RMSF), Rotavirus infection, Rubella, Salmonellosis, SARS (Severe Acute Respiratory Syndrome), Scabies, Schistosomiasis, Sepsis, Shigellosis, Shingles (Herpes zoster), Smallpox, Sporotrichosis, Staphylococcal food poisoning, Staphylococcal infection, Strongyloidiasis, Syphilis, Taeniasis, Tetanus (Lockjaw), *Tinea barbae* (Barber's itch), *Tinea capitis* (Ringworm of the Scalp), *Tinea corporis* (Ringworm of the Body), *Tinea cruris* (Jock itch), *Tinea manuum* (Ringworm of the Hand), *Tinea nigra, Tinea pedis* (Athlete's foot), *Tinea unguium* (Onychomycosis), *Tinea versicolor* (Pityriasis versicolor), Toxocariasis (Ocular Larva Migrans (OLM)), Toxocariasis (Visceral Larva Migrans (VLM)), Toxoplasmosis, Trichinellosis, Trichomoniasis, Trichuriasis (Whipworm infection), Tularemia, *Ureaplasma urealyticum* infection, Venezuelan equine encephalitis, Venezuelan hemorrhagic fever, Viral pneumonia, West Nile Fever, White piedra, Yersiniosis, Yellow fever, or Zygomycosis, among others.

VIII. Methods of Treating, Inhibiting or Sensitizing a Bacterial Pathogen

Embodiments disclosed herein include the use of compositions in methods to inhibit a drug resistant bacterial pathogen, methods of sensitizing a drug resistant bacterial pathogen to a drug the bacterial pathogen is resistant to and methods of inhibiting a drug-sensitive bacterial pathogen from developing drug resistance, among others.

Some embodiments include methods of inhibiting a bacterial pathogen by selecting a drug resistant pathogen and contacting the pathogen with a composition as described herein, for example a composition comprising MSM and an antimicrobial agent. For example, contacting a selected drug resistant bacterial pathogen with a composition comprising 10-16% MSM and a MIC level of anti-microbial agent. In some embodiments the bacterial pathogen is MRSA and the anti-microbial agent is a Beta-lactam antibiotic, for example methicillin or oxacillin. In some embodiments, the bacterial pathogen is in a subject, or on a surface.

Some embodiments include methods of sensitizing a drug resistant bacterial pathogen to a drug that the pathogen is resistant to, by selecting a drug resistant bacterial pathogen and contacting the pathogen with a composition comprising MSM. For example, contacting a selected bacterial pathogen with a composition comprising 10-16% MSM. In some embodiments, the selected bacterial pathogen is MRSA. In some embodiments, the bacterial pathogen is in a subject, or on a surface.

Some embodiments include methods of inhibiting a drug sensitive bacterial pathogen from developing drug resistance by selecting a drug sensitive bacterial pathogen and contacting the pathogen with a composition as described herein, for example a composition comprising MSM and an antimicrobial agent. For example, contacting a selected drug sensitive bacterial pathogen with 10-16% MSM and a MIC level of anti-microbial agent. In some embodiments, the bacterial pathogen is *Staphylococcus aureus* and the antimicrobial agent is a Beta-lactam antibiotic, for example methicillin or oxacillin. In some embodiments, the bacterial pathogen is in a subject, or on a surface.

In some embodiments, a composition comprising MSM and a sub-MIC concentration of an antibiotic is equally or more effective at reducing or killing certain drug resistant bacteria as compared to the antibiotic alone at MIC levels. In other embodiments, a composition comprising MSM and an antibiotic are more effective at reducing or eliminating bacteria from a site of infection as compared to the antibiotic alone. In several embodiments, compositions disclosed herein augment treatment of MRSA.

Selecting a Drug Sensitive Bacterial Pathogen

Methods of selecting a drug sensitive bacterial pathogen are well known to those of skill in the art. For example, in some embodiments a drug sensitive bacterial pathogen as described herein is detected, and then selected, thereby selecting a drug sensitive bacterial pathogen. Methods of detecting a bacterial pathogen as described herein are well known to those of skill in the art. For example, such a detection can be based on a determination of the MIC of an antibiotic for a drug sensitive bacterial pathogen. Methods of determining a MIC are well known to those of skill in the art (see, e.g., Andrews, *J. of Antimicrobial Chemotherapy*, 48:5-16, 2001). For example, MICs can be determined by agar or broth dilution methods usually following the guidelines of a reference body such as the CLSI, BSAC or EUCAST. There are several commercial methods available, including the well-established Etest® strips (bioMérieux SA, France) and the Oxoid MICEvaluator method. The Etest® system comprises a predefined and continuous concentration gradient of different antimicrobial agents, which when applied to inoculated agar plates and incubated, create ellipses of microbial inhibition. The MIC is determined where the ellipse of inhibition intersects the strip, and is easily read off the MIC reading scale on the strip (see, e.g., Andrews, *J. of Antimicrobial Chemotherapy*, 48:5-16, 2001).

In some embodiments, a *Staphylococcus aureus* bacterium as described herein is detected, and then selected, thereby selecting a drug sensitive bacterial pathogen. *Staphylococcus aureus* is a Gram-positive coccus where the round cells, approximately 1 μm in diameter, form grape-like clusters indicative of the ability to divide in more than one plane. This bacterium is capable of both aerobic and anaerobic respiration and most strains ferment mannitol anaerobically. On blood agar they form characteristic golden or white colonies. They produce catalase, coagulase and an extracellular cell clumping factor, and some strains produce capsules (see Brown et al., *J. Antimicrob. Chemother.*, 56: 1000-1018, 2005).

Methods of detecting *Staphylococcus aureus* are known to those of skill in the art. Non-limiting detection methods include the tube coagulase test, slide coagulase test, latex agglutination test, DNase and heat-stable nuclease tests, commercial biochemical tests such as the VITEK 2 system (bioMérieux), Staphychrom II (International Microbio, Signes, France), the Phoenix system (Becton Dickinson Microbiology Systems, Sparks, Md.) and molecular tests including PCR- and DNA probe-based tests. For review, see Brown et al., *J. Antimicrob. Chemother.*, 56: 1000-1018, 2005). Using the Etest® system, a drug sensitive *Staphylococcus aureus* bacterial pathogen will general have a MIC for oxacillin of 2 μg/ml or less (see, e.g., the Etest® technical manual, AB bioMérieux, 2008).

Some embodiments comprise selecting a drug sensitive bacterial pathogen, wherein the pathogen is on a surface. These embodiments comprise determining if a drug sensitive bacterial pathogen is on a surface, and selecting such a surface, thereby selecting a drug sensitive pathogen on a surface. Alternatively, some embodiments include selecting a surface with a drug sensitive bacterial pathogen. One of skill in the relevant art will understand how to perform such methods. Non-limiting examples include observation of the surface or obtaining a sample from the surface and detecting a drug sensitive bacterial pathogen in the sample. Methods of detecting a drug sensitive bacterial pathogen are known to those of skill in the art and are described herein. Examples of observation of the surface include recognizing when a surface has come into contact with a drug sensitive bacterial pathogen, for example if a drug sensitive bacterial pathogen is known to have contacted the surface.

Some embodiments comprise selecting a drug sensitive bacterial pathogen, wherein the pathogen is in a subject. These embodiments comprise determining if a drug sensitive bacterial pathogen is in a subject, and selecting such a subject, thereby selecting a drug sensitive pathogen in a subject. Alternatively, some embodiments include selecting a subject with a drug sensitive bacterial pathogen. One of skill in the relevant art will understand how to perform such methods. Non-limiting examples include observation of the subject or obtaining a biological sample from the subject and detecting a drug sensitive bacterial pathogen in the sample. Methods of detecting a drug sensitive bacterial pathogen are known to those of skill in the art and are described herein. Examples of observation of the subject include recognizing symptoms presented by a subject that has a drug sensitive bacterial pathogen in them as well as observing success of drug treatment of the bacterial pathogen in the subject.

Selecting a Drug Resistant Bacterial Pathogen

Methods of selecting a drug resistant bacterial pathogen are well known to those of skill in the art. For example, in some embodiments a drug resistant bacterial pathogen as described herein is detected, and then selected, thereby selecting a drug resistant bacterial pathogen. Methods of detecting a drug resistant bacterial pathogen as described herein are well known to those of skill in the art. For example, such a selection can be based on the MIC of an antibiotic for a bacterial pathogen. Methods of determining a MIC are well known to those of skill in the art and described herein.

In some embodiments, selecting a drug resistant bacterial pathogen comprises selecting a MRSA. Methods of selecting a drug resistant bacterial pathogen wherein the pathogen is a MRSA are known to those of skill in the art. For example, in some embodiments a MRSA bacterium as described herein is detected, and then selected, thereby selecting a MRSA. Methods of detecting MRSA are known to those of skill in the art.

For example, non-limiting examples of detecting a MRSA include the Etest® system (bioMérieux SA, France) in combination with a finding that the bacterium in question is a *Staphylococcus aureus* bacterium, Disc diffusion, a latex agglutination test with antibodies against PBP2a or PBP2', and molecular tests including PCR- and DNA probe-based tests. For review, see Brown et al., *J. Antimicrob. Chemother.*, 56: 1000-1018, 2005 and Sturenburg, *Ger. Med. Sci.*, 6: Doc 06, 2009. Additional methods are described in U.S. Pat. Nos. 7,449,289, 7,297,517, 5,496,706, 5,776,712 and 6,197,504 and US Patent Application Publication No. 2003/0165953, 2006/0040871, 2007/0082340, 2008/0220428, 2008/0227087, 2009/0081663, 2009/0130115, 2009/0181395, 2009/0203013, 2009/0325147, 2010/0197649. Using the Etest® system, a MRSA bacterial pathogen will general have a MIC for oxacillin of 2 μg/ml or more (see, e.g., the Etest® technical manual, AB bioMérieux, 2008).

Some embodiments comprise selecting a drug resistant bacterial pathogen, wherein the pathogen is on a surface. These embodiments comprise determining if a drug resistant bacterial pathogen is on a surface, and selecting such a surface, thereby selecting a drug resistant pathogen on a surface. Alternatively, some embodiments include selecting a surface with a drug resistant bacterial pathogen. One of skill in the relevant art will understand how to perform such methods. Non-limiting examples include observation of the surface or obtaining a sample from the surface and detecting a drug resistant bacterial pathogen in the sample. Methods of detecting a drug resistant bacterial pathogen are known to those of skill in the art and are described herein. Examples of observation of the surface include recognizing when a surface has come into contact with a drug resistant bacterial pathogen, for example if a drug resistant bacterial pathogen is known to have contacted the surface.

Some embodiments comprise selecting a drug resistant bacterial pathogen, wherein the pathogen is in a subject. These embodiments comprise determining if a drug resistant bacterial pathogen is in a subject, and selecting such a subject, thereby selecting a drug resistant pathogen in a subject. Alternatively, some embodiments include selecting a subject with a drug resistant bacterial pathogen. One of skill in the relevant art will understand how to perform such methods. Non-limiting examples include observation of the subject or obtaining a biological sample from the subject and detecting a drug resistant bacterial pathogen in the sample. Methods of detecting a drug resistant bacterial pathogen are known to those of skill in the art and are described herein. Examples of observation of the subject include recognizing symptoms presented by a subject that has a drug resistant bacterial pathogen in them as well as observing failure of drug treatment of the bacterial pathogen in the subject.

Some embodiments comprise selecting a drug resistant bacterial pathogen in a subject, wherein the drug resistant pathogen is MRSA. These embodiments comprise determining if MRSA is in a subject, and selecting such a subject, thereby selecting a MRSA in a subject. Alternatively, some embodiments include selecting a subject with MRSA. One of skill in the art will know how to perform such methods. Non-limiting examples include observation of a subject or obtaining a biological sample from the subject and detecting the presence of MRSA in the sample.

Examples of observation of the subject include recognizing symptoms of MRSA infection in the subject, observing failure of Beta-lactam antibiotic treatment of a subject having a bacterial pathogen infection, for example a *Staphylococcus aureus* infection, as well as observing failure of Beta-lactam antibiotic treatment of a subject having a MRSA symptom. Other methods of observing a subject to determine if the subject is a subject with MRSA are known to those of skill in the art.

Methods of obtaining a biological sample from the subject and testing the sample for the presence of MRSA are well known to those of skill in the art. For example, MRSA can be detected by swabbing the nostrils of patients and isolating the bacteria found inside. Methods of detecting a drug resistant bacterial pathogen are known to those of skill in the art and are described herein. Examples of observation of the subject include recognizing symptoms presented by a subject that has a bacterial pathogen in them as well as observing failure of drug treatment of the bacterial pathogen in the subject.

Contacting a Bacterial Pathogen

Methods of contacting a bacterial pathogen with a composition are well known to those of skill in the relevant art. Such methods will depend on the type and location of the bacterial pathogen and the type of composition used. Described herein are methods of contacting a bacterial pathogen, including methods of contacting a bacterial pathogen in a subject, and methods of contacting a bacterial pathogen on a surface, among others. One of skill in the art will know which method to apply.

In some embodiments, a method of contacting a bacterial pathogen on a surface with a composition as described herein is provided. For example, by spraying a composition as provided herein onto the surface, or by wiping a surface with a wipe comprising a composition as provided herein. One of skill in the art will understand how to apply compositions as described herein to a surface.

In some embodiments, a method of contacting a bacterial pathogen in a subject with a composition as described herein is provided. Such methods include administration of a compound as described herein to a subject, such that the compound comes into contact with a bacterial pathogen. For example, a compound or agent, such as MSM, may be given to a subject by any effective route. Exemplary routes of administration include, but are not limited to, injection (such as subcutaneous, intramuscular, intradermal, intraperitoneal, and intravenous), oral, sublingual, rectal, transdermal (such as topical), intranasal, vaginal and inhalation routes. Particular types of administration include topical administration or administration to the nasal mucosa or lungs by inhalational administration.

In some embodiments, a composition formulated for topical administration may be used to contact a bacterial pathogen located on or in the skin of a subject. A composition formulated for inhalant administration may be used to contact a bacterial pathogen located in the airway, mucosal membranes or lungs of a subject, among others.

In some embodiments, a composition comprising MSM, or MSM and an antimicrobial agent, is formulated for topical administration and is used to contact a drug resistant bacterial pathogen located on or in a subject. One of skill in the art will understand when topical administration is appropriate. For example, topical administration is appropriate when the bacterial pathogen is located on a subject's skin or on the surface of the subject's body.

In other embodiments a composition comprising MSM or MSM and an antimicrobial agent is formulated for administration via an inhalant device and is used to contact a drug resistant bacterial pathogen located on or in a subject. One of skill in the art will understand when administration via an inhalant device is appropriate. For example, administration via an inhalant device is appropriate when the bacterial pathogen is located in a subjects mucosal membranes or in a subjects lungs.

Methods of contacting a bacterial pathogen may employ specialized devices, for example an inhalation device. Inhalation devices are useful to deliver a composition as described herein to a bacterial pathogen located in the mucosal membranes, airway and/or lungs of a subject.

Inhalants, according to some embodiments, provide direct access of MSM and/or other agents to infected lung tissue to sensitize bacterial pathogens to the antibiotic. Alternatively, inhalants provide direct access of MSM and an antimicrobial agent to infected lung tissue to inhibit or treat the bacterial pathogen. According to some embodiments, inhalants are useful to treat MRSA infected lung tissue.

In one embodiment, an inhalant is provided to target the site of infection (e.g., lungs) of several infectious diseases, such as MRSA infection. In some such embodiments, the inhalant device comprises a nebulizer. In other embodiments, an inhaler is used. In some embodiments, a pressurized metered-dose inhaler is used, and the composition is inhaled in liquid aerosol form. In other embodiments, dry powder inhalers are used, and the composition is inhaled in a powder aerosol form. In several embodiments, oral, intravenous, intramuscular, or subcutaneous administration is used in addition to or instead of inhalant therapy.

In certain embodiments, the inhalant device delivers droplets or particles of the inhaled formulation of a size capable of reaching the bronchioles of the patient's lungs. In some embodiments, the inhalant device is synchronized with a patient's breathing rhythm to carry the formulation to the bronchioles. Inhalant therapy according to one embodiment, enables more direct administration the inhaled formulation to infected pulmonary target tissues. Direct targeting is advantageous in some embodiments because it allows for reduction of the amount of antimicrobial compounds incorporated into the formulation while maintaining or improving efficacy of the formulation against infectious microorganisms. In other embodiments, direct administration increases the efficacy of a given antimicrobial regime against one or more drug-resistant strains of microorganism. Direct targeting, according to other embodiments, minimizes side effects by minimizing contact with non-targeted tissue.

The small droplet or particle size that are provided according to some embodiments reduces the volume MSM that is administered as compared to traditional ventilator therapy The ability to administer anti-microbial agents as an inhalant (e.g., in a powder aerosol form) with MSM is especially advantageous in some embodiments because it allows for increased shelf-stability and pre-packaged dosages. This is particularly helpful for individuals in underdeveloped or developing nations who do not have regular access to healthcare facilities. Entire courses of treatment can be provided to an affected subject in a single visit to a healthcare practitioner without the need for a hospital stay or repeat visits. In several embodiments, compositions disclosed herein are suitable for self-administration (e.g., through inhalant devices) and are therefore especially appropriate for patients with limited access to healthcare.

In certain embodiments, the total volume of inhaled composition comprising MSM and/or other agents is about 2-8 ml. In some embodiments, the total volume of inhaled composition comprising MSM and/or other agents is about 2 ml to about 4 ml. In some embodiments, the total volume of inhaled MSM and/or other agents is about 6 ml to about 8 ml. In still other embodiments, the total volume of inhaled composition comprising MSM and/or other agents is about 3 ml to about 7 ml, including 4, 5, and 6 ml. Thus, in some embodiments, the concentration of MSM administered via inhalation ranges from about 0.01% to about 20%, including about 5, 6, 7, 8, 9, 10, 11, 12, 13, 14, 15, 16, 17, 18, 19, or 20%.

In various embodiments, contacting a bacterial pathogen includes contacting the pathogen with a therapeutically effective amount of an anti-microbial agent. Such contacting can involve administration in a single dose, or in several doses, for example daily, during a course of treatment.

In some embodiments, contacting a bacterial pathogen with a composition as described herein includes contacting the pathogen with the composition for about 1 hour to about 10 day, or any time in between. In some embodiments, the bacterial pathogen is contacted for about 12, 24, 36, 48, 60, 72, 84, 96, 108, or about 120 hours, with a composition as described herein. In some embodiments, the bacterial pathogen is contacted for about 1, 2, 3, 4, 5, 6, 7, 8, 9, 10, 11, 12, 13, 14, 15, 16, 17, 18, 19, 20, 21, 22, 23, or about 24 hours, with a composition as described herein. In some embodiments, the bacterial pathogen is contacted with a composition as described herein for about 24, 36, 48, 60, 72, 84, 96, 108, or about 120 hours. In some embodiments, higher or lower contact times may be used.

X. Compositions

Agents (e.g., MSM and Beta-lactam antibiotics) described herein may be formulated in a variety of ways depending on intended use. Various types of compositions are disclosed herein, including compositions for use on a subject and compositions for use in an industrial setting. The skilled artisan will know when to use a particular composition.

Compositions for use on a subject can be formulated in a variety of ways depending on the location and type of disease to be treated or prevented in the subject. Such compositions are thus provided for both local use at or near an affected area and for systemic use (in which the agent is administered in a manner that is widely disseminated via the cardiovascular system). Other types of compositions are also disclosed herein, for example, compositions for use on a surface.

This disclosure includes within its scope compositions including DMSO, DMSO without MSM, MSM, MSM without DMSO and/or antimicrobial agents, or combinations thereof that are formulated for use in human or veterinary medicine.

For example, the provided compositions may include compositions comprising MSM in the ranges of about 0.01% by weight to about 20% by weight. In other embodiments, the composition contains between about 0.01% and 5% MSM by weight. Other embodiments contain between about 5 and 10% MSM, about 10-15% MSM, about 15-20% MSM. Other composition comprise about 5-20% MSM, about 5-16% MSM, about 5-10% MSM, about 5-8% MSM, about 9-16% MSM or about 10-15% MSM. Other embodiments include about 5, 6, 7, 8, 9, 10, 11, 12, 13, 14, 15, 16, 17, 18, 19 or 20% MSM. Some embodiments include about 10-16% MSM, about 10-14% MSM or about 10-12% MSM. In some embodiments, higher or lower percentages may be used. While the compositions comprising MSM typically will be used to treat human subjects, they may also be used to treat similar or identical diseases in other vertebrates, such other primates, dogs, cats, horses, and cows.

Compositions provided herein also include compositions containing anti-microbial agents, for example a Beta-lactam antibiotic. For example compositions as described herein may include penicillin derivatives, cephalosporins, penems, monobactams, carbapenems, Beta-lactamase inhibitors and combinations thereof. Examples of penicillin derivatives include, but are not limited to, aminopenicillins (e.g., amoxacillin, ampicillin, and epicillin); carboxypenicillins (e.g., carbenicillin, ticarcillin, and temocillin); ureidopenicillins (e.g., azlocillin, piperacillin and mezlocillin); mecillinam, sulbenicillin, benzathine penicillin, penicillin G (benzylpenicillin), penicillin V (phenoxymethylpenicillin), penicillin O (allylmercaptomethylpenicillinic), procaine penicillin, oxacillin, methicillin, nafcillin, cloxacillin, dicloxacillin, flucloxacillin, pivampicillin, hetacillin, becampicillin, metampicillin, talampicillin, co-amoxiclav (amoxacillin plus clavulanic acid), and piperacillion. Examples of cephalosporins include, but are not limited to, cephalexin, cephalothin, cefazolin, cefaclor, cefuroxime, cefamandole, cefotetan, cefoxitin, ceforanide, ceftriaxone, cefotaxime, cefpodoxime proxetil, ceftazidime, cefepime, cefoperazone, ceftizoxime, cefixime and cefpirome. Examples of penems include, without limitation, faropenem. Examples of monobactams include, without limitation, aztreonam and tigemonam. Examples of carbapenems include, but are not limited to, biapenenvdoripenem, ertapenem, -imipenem, -meropenem, -and panipenem. Examples of Beta-lactamase inhibitors include, but are not limited to, tazobactam ([2S-(2alpha, 3beta,5alpha)]-3-Methyl-7-oxo-3-(1H-1,2,3-triazol-1-ylmethyl)-4-thia-1-azabicyclo[3.2.0]heptane-2-carboxylic acid 4,4-dioxide sodium salt), sulbactam (2S,5R)-3,3-dimethyl-7-oxo-4-thia-1-azabicyclo[3.2.0]heptane-2-carboxylic acid 4,4-dioxide sodium), and clavulanic acid ((2R,5R,Z)-3-(2-hydroxyethylidene)-7-oxo-4-oxa-1-aza-bicyclo[3.2.0]heptane-2-carboxylic acid), or other Beta-lactam antibiotic.

Many antibiotics have an established minimum inhibitory concentration (MIC) at which they are effective in reducing or killing certain bacteria. Some compositions provided herein comprise an amount of Beta-lactam antibiotic equal to about 0.001 to 100 MIC for the particular bacterial pathogens disclosed herein. In some embodiments the composition comprises about 1-5, 5-10, 10-20, 20-30, 30-40, 40-50, 50-60, 60-70, 70-80, 80-90 or about 90-100 MIC of a Beta-lactam antibiotic. In some embodiments, the composition comprises about 0.001, 0.01, 0.1, 0.5 or 1 MIC of a Beta-lactam antibiotic. One of skill in the art will know the MIC of an antibiotic for a particular bacterial pathogen, or the skilled artisan will know how to determine the MIC of an antibiotic for a particular bacterial pathogen. Methods of determining a MIC of a particular antibiotic for a particular bacterial pathogen are disclosed herein, for example use of the Etest® system. It is conventional for the skilled artisan to calculate a MIC of a particular antibiotic for a particular bacterial pathogen.

Compositions provided herein also include combinations of MSM and antimicrobial compounds, for example a combination of MSM and a Beta-lactam antibiotic. Such combinations can include any amount of MSM and/or anti-microbial agent as a composition that only includes MSM or a antimicrobial agent. In some embodiments, compositions provided herein include 10-16% MSM and an amount of a Beta-lactam antibiotic equal to 1 MIC for a bacterial pathogen the composition will be contacting.

The compositions provided herein that contain MSM are water-based compositions. The compositions provided herein that contain MSM preferably contain about 0% to about 5% sodium chloride by weight. In some embodiments, the compositions comprise about 0.0001, 0.001, 0.01, 0.1, 0.5, 1, 2, 3, 4 or 5% sodium chloride.

The dosage form of the composition will be influenced by the mode of administration chosen. For instance, in addition to injectable fluids, inhalational, topical, ophthalmic, peritoneal, and oral formulations can be employed. Inhalational preparations can include aerosols, particulates, and the like. In general, the goal for particle size for inhalation is about 1 μm or less in order that the agent reach the alveolar region of the lung for absorption.

Compositions that include MSM, DMSO, an antimicrobial agent or therapeutic compound as described herein as an active ingredient, or that include a mixture of two or more thereof, with or without additional agent(s) as active ingredients, may be formulated with an appropriate solid or liquid carrier, depending upon the particular mode of administration chosen. Oral formulations may be liquid (for example, syrups, solutions, or suspensions), or solid (for example, powders, pills, tablets, or capsules). For solid compositions, conventional non-toxic solid carriers can include pharmaceutical grades of mannitol, lactose, starch, or magnesium stearate. Actual methods of preparing such dosage forms are known, or will be apparent, to those of ordinary skill in the art.

For oral administration, the compositions can take the form of, for example, tablets or capsules prepared by conventional means with pharmaceutically acceptable excipients such as binding agents (for example, pregelatinised maize starch, polyvinylpyrrolidone or hydroxypropyl methylcellulose); fillers (for example, lactose, microcrystalline cellulose or calcium hydrogen phosphate); lubricants (for example, magnesium stearate, talc or silica); disintegrants (for example, potato starch or sodium starch glycolate); or wetting agents (for example, sodium lauryl sulphate). The tablets can be coated by methods well known in the art. Liquid preparations for oral administration can take the form of, for example, solutions, syrups or suspensions, or they can be presented as a dry product for constitution with water or other suitable vehicle before use. Such liquid preparations can be prepared by conventional means with pharmaceutically acceptable additives such as suspending agents (for example, sorbitol syrup, cellulose derivatives or hydrogenated edible fats); emulsifying agents (for example, lecithin or acacia); non-aqueous vehicles (for example, almond oil, oily esters, ethyl alcohol or fractionated vegetable oils); and preservatives (for example, methyl or propyl-p-hydroxybenzoates or sorbic acid). The preparations can also contain buffer salts, flavoring, coloring, and sweetening agents as appropriate.

For administration by inhalation, the agents and compositions for use according to the present disclosure are conveniently delivered in the form of an aerosol spray presentation from pressurized packs or a nebulizer, with the use of a suitable propellant, for example, dichlorodifluoromethane, trichlorofluoromethane, dichlorotetrafluoroethane, carbon dioxide or other suitable gas. In the case of a pressurized aerosol, the dosage unit can be determined by providing a valve to deliver a metered amount. Capsules and cartridges for use in an inhaler or insufflator can be formulated containing a powder mix of the compound and a suitable powder base such as lactose or starch.

For topical administration, the compounds can be, for example, mixed with a liquid delivery agent for administration locally. The agents used therapeutically (such as DMSO, MSM and/or Beta-lactam antibiotic other inhibitor or therapeutic compound as described herein) are readily soluble or suspendable in water, and as such this would be useful for delivery since water does not cause adverse biological tissue effects. This allows sufficiently high doses to be administered locally or systemically, without secondary toxicity from the delivery vehicle. Those of skill in the art will understand the appropriate buffering conditions for the MSM and Beta-lactam antibiotic.

Compositions that comprise at least one agent as described herein as an active ingredient will normally be formulated with an appropriate solid or liquid carrier, depending upon the particular mode of administration chosen. The pharmaceutically acceptable carriers and excipients useful in this disclosure are conventional. For instance, parenteral formulations usually comprise injectable fluids that are pharmaceutically and physiologically acceptable fluid vehicles such as water, physiological saline, other balanced salt solutions, aqueous dextrose, glycerol or the like. Excipients that can be included are, for instance, proteins, such as human serum albumin or plasma preparations. If desired, the composition to be administered may also contain minor amounts of non-toxic auxiliary substances, such as wetting or emulsifying agents, preservatives, and pH buffering agents and the like, for example sodium acetate or sorbitan monolaurate. Actual methods of preparing such dosage forms are known, or will be apparent, to those skilled in the art.

For example, for parenteral administration, therapeutic agent(s) can be formulated generally by mixing them at the desired degree of purity, in a unit dosage injectable form (solution, suspension, or emulsion), with a pharmaceutically acceptable carrier, for instance, one that is non-toxic to recipients at the dosages and concentrations employed and is compatible with other ingredients of the formulation. A pharmaceutically acceptable carrier is a non-toxic solid, semisolid or liquid filler, diluent, encapsulating material or formulation auxiliary of any type.

Generally, the formulations are prepared by contacting the agent(s) each uniformly and intimately with liquid carriers or finely divided solid carriers or both. Then, if necessary, the product is shaped into the desired formulation. Optionally, the carrier is a parenteral carrier, and in some embodiments it is a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The compositions that comprise at least one agent, in some embodiments, will be formulated in unit dosage form, suitable for individual administration of precise dosages. The amount of active compound(s) administered will be dependent on the subject being treated, the severity of the affliction, and the manner of administration, and is best left to the judgment of the prescribing clinician. Within these bounds, the formulation to be administered will contain a quantity of the active component(s) in amounts effective to achieve the desired effect in the subject being treated.

Preparations for administration can be suitably formulated to give controlled release of the therapeutic agent(s) (e.g., DMSO, MSM, Beta-lactam antibiotic and so forth). For example, the compositions may be in the form of particles comprising a biodegradable polymer and/or a polysaccharide jellifying and/or bioadhesive polymer, an amphiphilic polymer, an agent modifying the interface properties of the particles and a pharmacologically active substance. These compositions exhibit certain biocompatibility features that allow a controlled release of the active substance. See, for example, U.S. Pat. No. 5,700,486.

Polymers can be used for controlled release. Various degradable and nondegradable polymeric matrices for use in controlled drug delivery are known in the art (Langer, *Accounts Chem. Res.* 26:537, 1993). For example, the block copolymer, polaxamer 407 exists as a viscous yet mobile liquid at low temperatures but forms a semisolid gel at body temperature. It has shown to be an effective vehicle for formulation and sustained delivery of recombinant interleukin-2 and urease (Johnston et al., *Pharm. Res.* 9:425, 1992; Pec, *J. Parent. Sci. Tech.* 44(2):58, 1990). Alternatively, hydroxyapatite has been used as a microcarrier for controlled release of proteins (Ijntema et al., *Int. J. Pharm.* 112:215, 1994). In yet another aspect, liposomes are used for controlled release as well as drug targeting of lipid-capsulated compounds (Betageri et al., *Liposome Drug Delivery Systems*, Technomic Publishing Co., Inc., Lancaster, Pa., 1993). Numerous additional systems for controlled delivery of therapeutic proteins are known (e.g., U.S. Pat. No. 5,055,303; U.S. Pat. No. 5,188,837; U.S. Pat. No. 4,235,871; U.S. Pat. No. 4,501,728; U.S. Pat. No. 4,837,028; U.S. Pat. No. 4,957,735; and U.S. Pat. No. 5,019,369; U.S. Pat. No. 5,055,303; U.S. Pat. No. 5,514,670; U.S. Pat. No. 5,413,797; U.S. Pat. No. 5,268,164; U.S. Pat. No. 5,004,697; U.S. Pat. No. 4,902,505; U.S. Pat. No. 5,506,206; U.S. Pat. No. 5,271,961; U.S. Pat. No. 5,254,342; and U.S. Pat. No. 5,534,496).

Compositions for use in industrial settings can be formulated in a variety of ways depending on the location and type of surface to be treated. Such compositions can be formulated according to any means that a pharmaceutical composition can be formulated, but additionally, can be formulated in additional means that would not normally be acceptable for administration to a subject. Compositions f ruse in an industrial setting are water-based and contain 0-5% sodium chloride. In some embodiments, such compositions are formulated to be applied to a surface via a wipe. In some embodiments such compositions are formulated to be sprayed onto a surface. One of skill in the art understands how to make such formulations.

X. Other Embodiments

In several embodiments described herein, formulations comprising DMSO and/or MSM are provided. Despite the increasing prevalence of drug-resistant pathogenic microbes, several embodiments of the formulations disclosed herein are unexpectedly effective in treating drug-resistant bacteria or other microbes. Other drug-resistant pathogenic microbes are also treated by DMSO alone, MSM alone, or a combination of DMSO and MSM, together with a therapeutic agent In several embodiments, the combination of DMSO and MSM allows a lower concentration of DMSO and/or MSM to be used. In other embodiment, the use of DMSO and/or MSM reduces the minimum efficacious concentration of other constituents of the formulation, thereby also reducing side effects from those constituents. For example, in one embodiment, the addition of DMSO, MSM or DMSO and MSM will permit a reduced dosage of antibiotics to achieve comparable or enhanced therapeutic effects.

In several embodiments, formulations comprising DMSO and/or MSM sensitize drug-resistant pathogens to drugs. In one embodiment, formulations comprising DMSO and/or MSM partially or fully reverse the drug-resistant nature of bacterial strains.

In several embodiments, formulations comprising DMSO and/or MSM and at least one therapeutic agent results lowers the concentration of DMSO, MSM, and/or the therapeutic agent needed to effectively treat one or more types of infection. In one embodiment, a formulation comprising DMSO, MSM, or a combination of the two sensitizes bacteria (whether drug-resistant or not) to antibiotics. Thus, such a formulation: (i) reduces the dose of antibiotic needed; (ii) reduces the treatment time; (iii) reduces the number of different antibiotics needed, and/or (iv) makes an antibiotic effective. Accordingly, undesired side effects associated with antibiotics may be reduced in several embodiments, including liver damage, kidney damage, ocular defects, hyperuricemia, thrombocytopenia, leukopenia, and neutropenia. In one embodiment, a DMSO and/or MSM formulation sensitizes drug-resistant pathogens to isoniazid, rifampicin, pyrazinamide, and/or ethambutol. In another embodiment, DMSO and/or MSM enhances the effects of isoniazid, rifampicin, pyrazinamide, and/or ethambutol on non-drug-resistant tuberculosis.

Many infections lead to local inflammation (or even inflammation of a large area of tissue around the site of infection). In some embodiments, DMSO and/or MSM works synergistically with therapeutic agents to reduce inflammation to a greater degree than DMSO, MSM or the agent alone.

In several embodiments, DMSO and MSM in a single formulation with a therapeutic agent act synergistically to reduce the amount of DMSO needed to achieve efficacious amounts of therapeutic agent delivery to a target site of infection. In some embodiments, MSM enhances the penetrant effect of DMSO, allowing a therapeutic agent to reach a target area of infection at an increased concentration (or reduced time frame). Thus, in some such embodiments, the synergy between MSM and DMSO reduce the side effects associated with DMSO administration, which include an unpleasant odor post administration, nausea, diarrhea, and skin/throat irritation, among others.

In still other embodiments, DMSO and MSM in a single formulation with a therapeutic agent act synergistically to reduce the amount of therapeutic agent needed to effectively treat an infection. For example, many antibiotics have an established minimum inhibitory concentration (MIC) at which they are effective in reducing or killing certain bacteria. In some embodiments, a formulation comprising DMSO and MSM and a sub-MIC concentration of an antibiotic is equally or more effective at reducing or killing certain bacteria as compared to the antibiotic alone at MIC levels. In other embodiments, a formulation comprising DMSO, MSM and an antibiotic are more effective at reducing or eliminating bacteria from a site of infection as compared to the antibiotic alone. In several embodiments, formulations disclosed herein augment treatment of multiple drug-resistant bacterial pathogens.

In one embodiment, a formulation comprising DMSO and ethambutol sensitizes bacteria to drugs other than ethambutol. In some embodiments, formulations comprising DMSO enhance the sensitivity or susceptibility to drugs such as sub-MIC concentrations of ethambutol, isoniazid, rifampicin, and streptomycin by about 2-fold to about 100-fold. Unlike prior reports, concentrations of DMSO greater than 50% are particularly advantageous in some embodiments (Jagannath et al. *J. Antimicrobial Chemotherapy* 35, 381-390, 1995, herein incorporated by reference).

In some embodiments, DMSO and/or MSM allow antibiotics (or other therapeutic agents) to penetrate lung tissue infected with a bacterial pathogen, including a drug-resistant bacterial pathogen. In one embodiment, DMSO and/or MSM: (i) allow antibiotics to reach deeper levels of infected tissue; (ii) allow direct contact of infected tissue; (iii) lengthen the exposure time of the antibiotic to the infected tissue; and/or (iv) decrease the time to achieve a desired antibiotic effect. In one embodiment, DMSO and/or MSM achieves one or more of these desired effects through use as an inhalant, wherein the inhalant additionally comprises one or more antibiotics or other therapeutic agents.

In several embodiments, the combined use of MSM reduces or eliminates the odor normally associated with DMSO. This is surprisingly beneficial in several embodiments because practitioners have avoided using DMSO in high concentrations (or in any amount) because of its unpleasant odor.

In some embodiments, DMSO and/or MSM formulations comprise antiparasitic agents that are effective in treating infections caused by parasites, such as nematodes, cestodes, trematodes, protozoa, or amoebae.

In some embodiments, DMSO and/or MSM formulations comprise antifungal agents that are effective in treating fungal infections, such as those caused by ringworm, candidiasis, and *Cryptococcus* (cryptococcal meningitis, for example).

In some embodiments, DMSO and/or MSM formulations comprise antiviral agents that are effective in treating viral infections. In some embodiments, specific classes of antiviral agents are used to treat infections caused by a particular type of virus. In some embodiments, agents that target HIV, herpes viruses, hepatitis B or C viruses, and influenza viruses are used.

In several embodiments, DMSO and/or MSM formulations comprise antibiotics that are effective in treating bacterial infections by, for example, inhibiting bacterial growth, metabolism, proliferation, activity and/or function. In some embodiments, bacteriostatic antibiotics are used, while in other embodiments, bactericidal antibiotics are used. In still other embodiments, both bacteriostatic and bactericidal antibiotics are incorporated into a single formulation comprising DMSO and/or MSM. In some embodiments, antibiotics of one or more classes are incorporated into a formulation comprising DMSO and/or MSM. In certain embodiments, a formulation includes one or more of an: aminoglycoside, ansamycin, carbacephem, carbapenem, cephalosporin ($1^{st}$, $2^{nd}$, $3^{rd}$, $4^{th}$ or $5^{th}$ generation), glycopeptides, macrolide, monobactam, penicillin, polypeptide, quinolone, sulfonamide, tetracycline, and the like.

In some embodiments, specific diseases are targeted by incorporating specific antibiotics into a formulation comprising DMSO and/or MSM. For example, macrolides, such as azithromycin or erythromycin are incorporated into formulations used to treat respiratory or mycoplasmal infections. Likewise, penicillins, such as amoxicillin or oxacillin are incorporated into formulations used to treat a broad range of streptococcal infections.

In still other embodiments, specific disease-causing microorganisms are targeted by the specific antibiotics incorporated into a formulation comprising DMSO and/or MSM. For example, aminoglycosides, such as neomycin are incorporated into formulations used to treat *Escherichia coli* infections. In several embodiments, antibiotics typically used to combat microbial infections are used. In certain embodiments, antibiotics including, but not limited to, isoniazid, rifampicin, pyrazinamide, and ethambutol are incorporated into formulations comprising one or more of DMSO and MSM, and are used to treat bacterial pathogens, including drug-resistant bacterial pathogens.

In several embodiments of the invention, formulations comprising DMSO, MSM and one or more of the following therapeutic agents: rifampicin, isoniazid, pyrazinamide, and ethambutol are provided. In other embodiments, formulations comprising DMSO and at least one of rifampicin, isoniazid, pyrazinamide, and ethambutol are provided. In further embodiments, formulations comprising MSM and at least one of rifampicin, isoniazid, pyrazinamide, and ethambutol are provided. In several embodiments, formulations comprising DMSO and/or MSM in combination with rifampicin, isoniazid, pyrazinamide, and ethambutol are provided to treat bacterial pathogens, including drug-resistant bacterial pathogens.

In some embodiments, rifampicin is provided in a total daily dose ranging from about 400 mg to about 800 mg per day. In some embodiments, rifampicin is provided in a total daily dose ranging from about 500 mg to about 700 mg per day, while in still other embodiments, it is provided in a total daily dose ranging from about 550 to about 650 mg per day, including 560, 570, 580, 590, 600, 610, 620, 630, and 640 mg per day.

In some embodiments, isoniazid is provided in a total daily dose ranging from about 100 mg to about 500 mg per day. In some embodiments, isoniazid is provided in a total daily dose ranging from about 200 mg to about 400 mg per day, while in still other embodiments, it is provided in a total daily dose ranging from about 250 mg to about 350 mg per day, including 260, 270, 280, 290, 300, 310, 320, 330, and 340 mg per day.

In some embodiments, pyrazinamide is provided in a total daily dose ranging from about 1.0 to about 4.0 g per day. In some embodiments, pyrazinamide is provided in a total daily dose ranging from about 2.0 to about 3.0 g per day, while in still other embodiments, it is provided in a total daily dose ranging from about 2.0 to 2.5 g per day, including 2.1, 2.2, 2.3, and 2.4 g.

In some embodiments, ethambutol is provided in a total daily dose ranging from about 0.5 to about 2.5 g per day. In some embodiments, ethambutol is provided in a total daily dose ranging from about 1.0 to 2.0 g per day, while in still other embodiments, it is provided in a total daily dose ranging from about 1.0 to about 1.5 g per day, including 1.1, 1.2, 1.3, and 1.4 g.

In some embodiments, DMSO and/or MSM is used to pretreat a patient suffering from an infectious disease. In some embodiments, the dose of DMSO and/or MSM used to pretreat patients ranges from about 10% to 50% weight to volume. In some embodiments, the pretreatment DMSO and/or MSM dose ranges from about 20% to about 40%, from about 25% to 35%, including 26, 27, 28, 29, 30, 31, 32, 33, and 34%. In some embodiments, about 50% to about 100% DMSO and/or MSM is used. In several embodiments, pretreatment with DMSO and/or MSM enhances the ability of an antibiotic to inhibit bacterial activity and/or sensitizes a drug-resistant strain to a drug that was previously ineffective.

In some embodiments, a formulation is prepared wherein antimicrobials are dissolved in DMSO and/or MSM prior to administration. This is particularly advantageous in certain embodiments because the antimicrobial and DMSO (and optionally MSM) can be administered to a subject via inhalation. Inhalants, according to some embodiments, provide direct access of the DMSO and/or MSM to infected lung In several embodiments, the use of MSM reduces the amount of DMSO needed to achieve a comparable effect and/or enhances the efficacy of DMSO by at least 10%, 25%, 50%, 100%, 2-fold, 3-fold, 5-fold, 10-fold, 50-fold, or 100-fold. In other embodiments, the use of MSM reduces the amount of a therapeutic agent needed to achieve a comparable effect and/or enhances the efficacy of the therapeutic agent by at least 10%, 25%, 50%, 100%, 2-fold, 3-fold, 5-fold, 10-fold, 50-fold, or 100-fold. In further embodiments, the use of DMSO reduces the amount of a therapeutic agent needed to achieve a comparable effect and/or enhances the efficacy of the therapeutic agent by at least 10%, 25%, 50%, 100%, 2-fold, 3-fold, 5-fold, 10-fold, 50-fold, or 100-fold. In still other embodiments, the use of DMSO and MSM reduces the amount of a therapeutic agent needed to achieve a comparable effect and/or enhances the efficacy of the therapeutic agent by at least 10%, 25%, 50%, 100%, 2-fold, 3-fold, 5-fold, 10-fold, 50-fold, or 100-fold as compared to DMSO or MSM alone and/or the therapeutic agent alone.

In several embodiments, a pretreatment formulation comprising DMSO, alone or in combination with MSM, is administered to a subject intravenously, intramuscularly, topically or orally to enhance the effects of an inhalant therapy comprising DMSO and/or MSM with therapeutic agents, such as antibiotics. The pretreatment with DMSO, alone or in combination with MSM, enhances the inhalant's therapeutic effects by at least 10%, 25%, 50%, 100%, 2-fold, 3-fold, 5-fold, 10-fold, 50-fold, or 100-fold.

In several embodiments, subjects having drug-resistant infectious disease are treated with a formulation comprising, consisting or consisting essentially of DMSO, alone or in combination with MSM, and one or more therapeutic agents, such as antibiotics. In some embodiments, the formulation additionally includes other therapeutics agents, carriers or excipients. In one embodiment, the formulation additionally includes arginine, vitamin D, antioxidants, macrolides, linezolid, thioacetazone, thioridazine, or combinations thereof.

DMSO readily disrupts the integrity of many materials (particularly plastics and polymers used in manufacturing disposable medical equipment). Accordingly, several embodiments of the invention comprise devices to facilitate the storage and administration of DMSO. In some embodiments, DMSO is stored in glass bottles and administered through non-reactive tubing. In other embodiments, inhalant devices are specially designed to be DMSO resistant. In some embodiments, portions of the inhalant devices are disposable or replaceable. According to several embodiments, formulations comprising DMSO are manufactured, stored and/or administered using materials and devices disclosed in U.S. patent application Ser. No. 12/066,480, which is the National Phase entry of International Application No.: PCT/US06/35499, filed Sep. 11, 2006, which is herein incorporated by reference in its entirety.

In several embodiments, the addition of MSM unexpectedly reduces the unpleasant odor normally experienced with DMSO use. For example, in certain embodiments, DMSO and MSM formulations produce no perceptible odor after use. In some other embodiments having DMSO concentrations approaching or exceeding 50%, the combination with MSM in the formulation reduces or eliminates the DMSO-based odor. Such a result is unexpected, given that DMSO use is normally associated with a strong unpleasant odor.

In some embodiments, the use of DMSO and/or MSM with therapeutic agents (such as antibiotics) permits the manufacture and/or administration of small droplets or particle sizes, thereby reducing the irritation of the mucosa of the mouth and throat, as the droplets or particles travel more deeply into the lungs of the patient. In some embodiments, the depth of travel of the droplets or particles increases the concentration of the dissolved antibiotics in the patient's lungs.

In several embodiments, DMSO and/or MSM formulations are combined with therapeutic agents (such as antibiotics) and provided as an aerosol to deliver locally-active drugs to the respiratory system to treat infectious disease or other respiratory diseases. In one embodiment, the lower airways are contacted (or contacted exclusively) with the formulation. In other embodiments, the formulation is used to systemically treat illnesses. For systemically-active drugs, the aerosol particles are sized to reach the alveolar surface in peripheral areas of the lung.

In some embodiments, the use of DMSO and/or MSM formulations comprising a therapeutic agent (such as an antibiotic) is particularly advantageous because it provides rapid onset of action. In one embodiment, inhalation delivery provides a large absorption area of the lung. For locally acting drugs, the onset of action is immediate in some embodiments. Systemically-active inhaled formulations, according to some embodiments, reach the blood stream quickly. Inhalation therapy provides a therapeutic effect within about 1-90 minutes in some embodiments. In one embodiment, DMSO and/or MSM enhance the bioavailability of the therapeutic agent. In a further embodiment, DMSO and/or MSM reduce the degradation of the therapeutic agent. In another embodiment, aerosol formulations disclosed herein reduce the gastrointestinal side effects or skin irritation that may occur with oral or topical treatment.

In several embodiments, inhalant particles are sized to minimize the deposit of those particles by inertial impact into the upper airways without reaching the site of action. In several embodiments, the particles are sized to minimize deposit in the mouth and throat, thereby minimizing swallowing and undesired local or systemic side effects. In several embodiments, the particles are smaller than 2, 5 or 10 µm. In one embodiment, the particles are about 3-5 µm and are transported into the bifurcations and smaller airways of the bronchii and bronchioles. In another embodiment, the particles are less than 3 µm and follow the airflow into the alveoli. In several embodiments, the use of DMSO and/or MSM allows for optimizing the particle size of the therapeutic agent. Moreover, in several embodiments, the use of DMSO and/or MSM sensitizes drug-resistant bacterial pathogens to antibiotics.

In several embodiments, DMSO and/or MSM forms a solution, mixture, emulsion, suspension, or other suitable combination with the therapeutic agent. In one embodiment, homogenization, sonication, high shear fluid processing, or other mechanical methods are used to combine the therapeutic agent with the DMSO and/or MSM. In other embodiments, the therapeutic agent dissolves readily in DMSO. Unlike other strong solvents, DMSO is not harmful to lung tissue. Thus, DMSO is especially advantageous in some embodiments because it can both dissolve the therapeutic agent and deliver said agent without damaging lung tissue. In some embodiments, DMSO dissolves at least 50%, 75%, 90%, 95%, or 99% of the therapeutic agent, and in one embodiment, is able to prevent undesired precipitation of the therapeutic agent.

The following examples are provided to illustrate certain particular features and/or embodiments. These examples should not be construed to limit the invention to the particular features or embodiments described.

EXAMPLES

Example 1

MSM Alone does not Affect MRSA Survival

This example describes in vitro experiments testing the survival of ATCC strain 43300 *Staphylococcus aureus* (a methicillin and oxacillin resistant strain) in the presence of MSM alone. ATCC strain 43300 *Staphylococcus aureus* was incubated with 5-16% MSM for 24 and 48 hours. An additional 3.5% MSM was added each day. The results show that MSM does not affect survival of this bacterial strain.

Methods:

USP<51> Antimicrobial Effectiveness protocol was used as the template experimental paradigm. Initial MSM concentrations tested were 5, 8, 10, 12, 13, 14, 15, and 16% MSM. All concentrations were plated out to the $10^{-7}$ dilutions to ascertain cfu/ml.

Materials used were Flake OptiMSM® MSM (lot number 0604751), ATCC strain 43300 *Staphylococcus aureus*, 30 ml Borosilicate glass cultures tubes, Lactose Broth (LB; Alpha Biosciences; Lot: L07-03), Modified Letheen Broth (MLB, Alpha Biosciences, lot I08-09), Trypto Soy Agar with Lecithin and Tween 80 (TSA; Alpha Biosciences, lot: F08-42), oxacillin sodium USP grade lot J and methicillin sodium (AS; Cat No. 1410002, lot KOH338).

Flake OptiMSM® MSM was weighed out on a certified Mettler Toledo AG245 SN: 1115210833 and aliquoted for each concentration. The MSM was placed into 30 ml borosilicate glass culture tubes. MSM was added to tubes as follows: 5% (0.5 g), 8% (0.8 g), 10% (1.0 g), 12% (1.2 g), 13% (1.3 g), 14% (1.4 g), 15% (1.5 g), and 16% (1.6 g). Material was calculated on a 10 ml volume.

All tubes were inoculated with a dilution of MRSA giving a final level of colony forming units of $2.0\times10^5$/ml (Log=5.23). The tubes were incubated at 25° C. and mixed periodically. Plating was done at 24 and 48 hours. Each condition was plated by diluting 1 ml of growth material into 9 ml of MLB diluent broth. This mixture was serial diluted down to $10^{-7}$, and 1 ml placed in a sterile petri dish at each dilution point. 20 mls of TSA was added to each dilution, swirled and allowed to solidify. All dilutions were placed in a 35° C. incubator for 24 hours. Bacterial colonies on each plate were counted and colony counts changed into log format. A positive and negative control was ascertained.

Results:

The results showed that none of the concentrations of MSM tested had any effect on the survival of ATCC strain 43300 *Staphylococcus aureus* at either the 24 or 48 hour time point.

Example 2

MSM Sensitizes MRSA to Oxacillin

This example describes in vitro experiments testing the survival of ATCC strain 43300 *Staphylococcus aureus* (a MRSA strain resistant to oxacillin and methicillin) in the presence of MSM, DMSO and oxacillin Results are shown in FIG. 1. A lower survival rate was observed in the presence of 9-16% MSM with 6 µg/ml oxacillin than in the presence of 1% DMSO and 6 µg/ml oxacillin or in the presence of 1% DMSO, 9-16% MSM and 6 µg/ml oxacillin. The lowest survival rate was observed in the 12 and 13% MSM with 6 µg/ml antibiotic conditions. These results show that specific concentrations of MSM alone can increase the sensitivity of a MRSA strain to antibiotic more efficaciously than DMSO or a combination of MSM and DMSO.

Methods

USP<51> Antimicrobial Effectiveness protocol was used as the template experimental paradigm. MSM Concentrations tested were 5-16% in increments of one. All concentrations were plated out to the $10^{-7}$ dilutions to ascertain cfu/ml. The initial concentration of oxacillin used was 6 µg/ml, which is the MIC for oxacillin. This concentration is the industry standard for determining MRSA resistance in clinical applications.

Materials used were Flake OptiMSM® MSM (lot number 0604751), DMSO (Jacob Labs, lot number 48074), ATCC strain 43300 *Staphylococcus aureus*, 30 ml Borosilicate glass cultures tubes, Lactose Broth (LB; Alpha Biosciences; Lot: L07-03), Modified Letheen Broth (MLB, Alpha Biosciences, lot I08-09), Trypto Soy Agar with Lecithin and Tween 80 (TSA; Alpha Biosciences, lot: F08-42) and oxacillin sodium USP grade lot J.

Flake OptiMSM® MSM was weighed out on a certified Mettler Toledo AG245 SN: 1115210833 and aliquoted for each concentration. The MSM was placed into 30 ml borosilicate glass culture tubes. Material was calculated on a 10 ml volume. MSM was added to tubes as follows: 5% (0.5 g), 6% (0.6 g), 7% (0.7 g), 8% (0.8 g), 9% (0.9 g), 10% (1.0 g), 11% (1.1 g), 12% (1.2 g), 13% (1.3 g), 14% (1.4 g), 15% (1.5 g), and 16% (1.6 g). Sterile DMSO was added to appropriate tubes. Sterile oxacillin was added to appropriate tubes at 300 microliters from a 30 mg/10 ml concentration giving it a final concentration of 6 µg/ml. Control conditions were Lactose Broth inoculated with ATCC strain 43300 *Staphylococcus aureus* with and without 6 µg/ml oxacillin, as well as uninoculated negative controls to show no signs of contamination.

Appropriate tubes were inoculated at a dilution of ATCC strain 43300 *Staphylococcus aureus* giving a final concentration of colony forming units of $3.15\times10^7$/ml (Log=7.49). The tubes were incubated at 25° C. and mixed periodically. Plating was done at 48 hours. The 5-16% tubes were plated by diluting 1 ml of material into 9 ml of MLB diluent broth. They were serial diluted down to $10^{-7}$ with 1 ml placed in a sterile petri dish at each dilution point. Then 20 mls of TSA was added to each dilution and swirled and allowed to solidify. All dilutions were placed in a 35° C. incubator for 24 hours. Plates were counted and colony counts changed into log format. A positive and negative control was ascertained.

Results:

The results of this study are shown in Table 1 and FIG. 1.

TABLE 1

ATCC strain 43300 *Staphylococcus aureus* survival in 5-16% MSM and oxacillin for 48 hours.

| % MSM (if added) | (MA) 6 μg/ml oxacillin MSM (Log cfu/ml) | (MDA) 6 μg/ml oxacillin MSM 1% DMSO (Log cfu/ml) | (DA) 6 μg/ml oxacillin No MSM 1% DMSO (Log cfu/ml) |
|---|---|---|---|
| 16 | 5.1 | 5.5 | 5.8 |
| 15 | 4.9 | 5.7 | 5.7 |
| 14 | 4.8 | 5.7 | 5.7 |
| 13 | 4.6 | 5.8 | 5.4 |
| 12 | 4.6 | 5.8 | 5.8 |
| 11 | 4.8 | 5.8 | 5.8 |
| 10 | 5.1 | 5.8 | 5.7 |
| 9 | 5.5 | 5.9 | 5.9 |
| 8 | 5.9 | 5.8 | 5.9 |
| 7 | 6.8 | 5.9 | 5.9 |
| 6 | 6.6 | 6.1 | 6.3 |
| 5 | 6.7 | 6.2 | 6.2 |

These results show that 9-16% MSM increased the sensitivity of ATCC strain 43300 *Staphylococcus aureus* to oxacillin for at least 48 hours. Minimal log reduction in cfu/ml with MA, DA, and MDA conditions at the 5-8% MSM concentration range was observed. "Log reduction in cfu/ml" refers to a decrease (reduction) in cfu/ml of a bacterial culture compared to the cfu/ml that the bacterial culture was initially inoculated with. At the 9% MSM concentration the MA condition showed a 2.0 log reduction in cfu/ml compared to the DA and MDA conditions which show a 1.6 log reduction in cfu/ml. At the 10-16% MSM concentration the MA condition showed a maximum 2.9 log reduction in cfu/ml compared to the DA and MDA conditions which showed a log reduction in cfu/ml of 1.69 and 2.0, respectively. At the 5-7% MSM concentration, the MA condition showed an increase in bacterial growth compared to the DA and MDA conditions. DMSO may have some inhibitory effect on the ability of 9-16% MSM/oxacillin to inhibit ATCC strain 43300 *Staphylococcus aureus* growth.

The positive control showed TNTC on the $10^6$ dilution plate. The negative control showed no signs of contamination. Overall, these results indicate that MSM can sensitize a MRSA strain to antibiotic treatment.

Example 3

MSM Sensitizes MRSA to Oxacillin in a Simulated Course of Treatment

Figure 2:
FIG. 2 is a graph illustrating that MSM sensitizes MRSA to oxacillin in a simulated course of treatment. In vitro survival of ATCC strain 43300 *staphylococcus aureus* (a MRSA strain resistant to oxacillin and methicillin), was tested in the presence of MSM and oxacillin ATCC strain 43300 *staphylococcus aureus* was incubated with 5-16% MSM and 6 µg/ml oxacillin for 24 hours at 25° C. After 24 hours, another 6 µg/ml oxacillin was added to the incubations, bringing the total amount of oxacillin added to 12 µg/ml. 6 µg/ml is the MIC for this strain of MRSA. Thus, the bacteria were under a MIC of oxacillin for 24 hours and 2×MIC for the following 24 hours. This experimental paradigm simulates the repeated application of antibiotic that a subject would receive over a course of treatment. The initial inoculation of bacteria was $9.14 \times 10^5$ cfu/ml (Log=5.96). The positive control showed TNTC on the $10^5$ dilution plate. Similar to the results shown in FIG. 1, the lowest survival rate was observed in the presence of 12 and 13% MSM. These results confirm that MSM sensitizes MRSA to antibiotic treatment and show that specific concentrations of MSM alone can increase the sensitivity of a MRSA strain to antibiotic in a simulated course of treatment.

This example describes in vitro experiments testing the survival of ATCC strain 43300 *Staphylococcus aureus* (a methicillin and oxacillin resistant strain) in the presence of MSM and oxacillin Results are shown in FIG. 2. ATCC strain 43300 *Staphylococcus aureus* was incubated with 5-16% MSM and 6 μg/ml oxacillin for 24 hours at 25° C. After 24 hours, another 6 μg/ml oxacillin was added to the incubations, bringing the total amount of oxacillin added to 12 μg/ml. 6 μg/ml is the MIC for this strain of MRSA. Thus, the bacteria were under a MIC of oxacillin for 24 hours and 2×MIC for the following 24 hours. This experimental paradigm simulates the repeated application of antibiotic that a subject would receive over a course of treatment. Similar to the results shown in Example 2, the lowest survival rate was observed in the presence of 12 and 13% MSM. These results confirm that MSM sensitizes MRSA to antibiotic treatment and show that specific concentrations of MSM alone can increase the sensitivity of a MRSA strain to antibiotic in a simulated course of treatment.

Methods:

USP<51> Antimicrobial Effectiveness protocol was used as the template experimental paradigm. MSM concentrations tested were 5, 8, 10, 12, 13, 14, 15, and 16%. All concentrations were plated out to the $10^{-7}$ dilutionsto ascertain cfu/ml. The initial concentration of oxacillin used was 6 μg/ml, which is the MIC for oxacillin for this strain of bacteria. This concentration is the industry standard for determining MRSA resistance in clinical applications. An additional 6 μg/ml oxacillin was added daily.

Materials used were Flake OptiMSM® MSM (lot number 0604751), ATCC strain 43300 *Staphylococcus aureus*, 30 ml Borosilicate glass cultures tubes, Lactose Broth (LB; Alpha Biosciences; Lot: L07-03), Modified Letheen Broth (MLB, Alpha Biosciences, lot I08-09), Trypto Soy Agar with Lecithin and Tween 80 (TSA; Alpha Biosciences, lot: F08-42) and oxacillin sodium USP grade lot J. Flake OptiMSM® MSM was weighed out on a certified Mettler Toledo AG245 SN: 1115210833 and aliquoted for each concentration. The MSM was placed into 30 ml borosilicate glass culture tubes. MSM was added to tubes as follows: 5% (0.5 g), 8% (0.8 g), 10% (1.0 g), 12% (1.2 g), 13% (1.3 g), 14% (1.4 g), 15% (1.5 g), 16% (1.6 g). Material was calculated on a 10 ml volume. Sterile oxacillin was added to each experimental condition daily at 300 μl from a 30 mg/10 ml concentration giving it a final concentration of 6 μg/ml.

All tubes were inoculated at a dilution of MRSA giving a final concentration of colony forming units of $9.14 \times 10^5$/ml (Log=5.96). The tubes were incubated at 25° C. and mixed periodically. Plating was done at 48 hours and 7 days. The 5-16% MSM tubes were plated by diluting 1 ml of material into 9 ml of MLB broth. These were serial diluted down to $10^{-7}$ with 1 ml placed in a sterile petri dish at each dilution point. 20 mls of TSA was added to each dilution and swirled and allowed to solidify. All dilutions were placed in a 35° C. incubator for 24 hours. Plates were counted and colony counts changed into log format. A positive and negative control was ascertained.

The results of this study are shown in Table 2 and FIG. 2.

TABLE 2

ATCC strain 43300 *Staphylococcus aureus* survival in 5-16% MSM and oxacillin at 48 and 168 hours:

| % MSM | 48 hours 6 μg/ml oxacillin MSM (Log cfu/ml) | 7 days 6 μg/ml oxacillin MSM (Log cfu/ml) |
|---|---|---|
| 16 | 5.3 | 1.0 |
| 15 | 4.1 | 6.9 |
| 14 | 4.0 | 7.0 |
| 13 | 3.8 | 7.2 |
| 12 | 3.8 | 7.1 |
| 10 | 4.6 | 7.2 |
| 8 | 4.0 | 7.6 |
| 5 | 7.0 | 7.9 |

These results show that MSM increased the sensitivity of ATCC strain 43300 *Staphylococcus aureus* to oxacillin for at least 48 hours. At the 48 hour time point, 12-15% MSM increased the sensitivity of ATCC strain 43300 *Staphylococcus aureus* to oxacillin more than any other MSM concentration tested. At the seven day time point, except for the highest concentration of MSM tested (16%), MSM did not increase the sensitivity of ATCC strain 43300 *Staphylococcus aureus* to oxacillin. The 16% MSM with 6 µg/ml added each day showed no surviving bacteria at day 7. This result shows that, except at the highest MSM concentration tested (16%), any initial MSM-induced oxacillin-sensitization of ATCC strain 43300 *Staphylococcus aureus* is reduced after prolonged exposure to MSM and antibiotic. Controls were terminated after 48 hours to minimize associated danger with unchecked growth of MRSA organism Example 4

MSM Sensitizes MRSA to Multiple Antibiotics

Figure 3A:
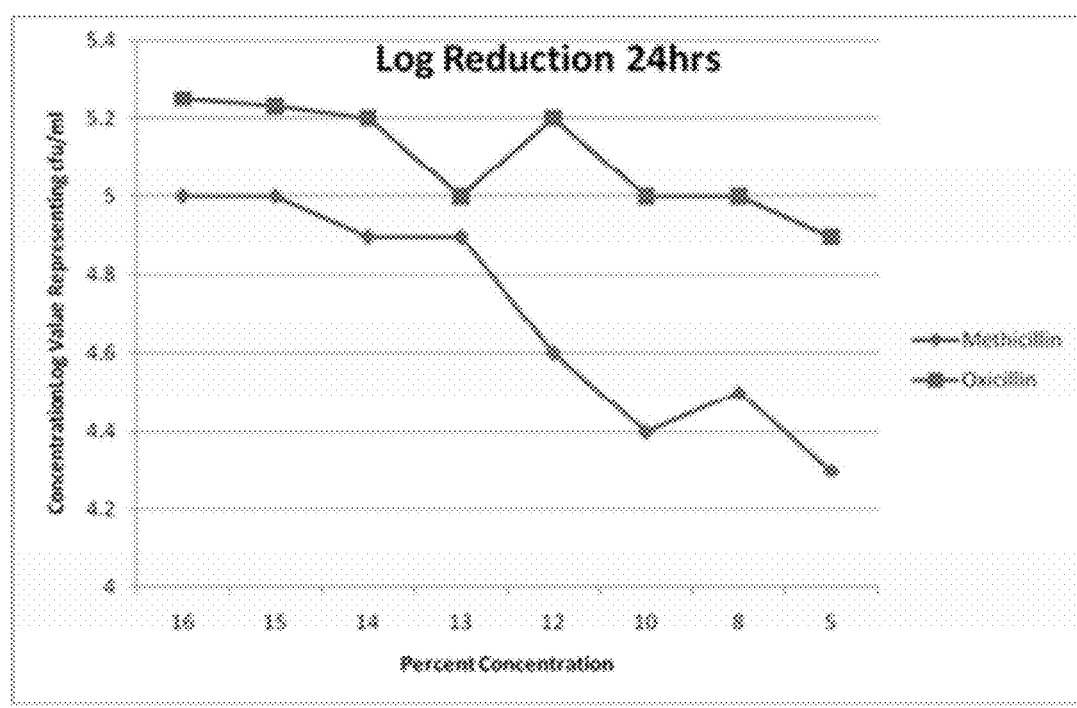
FIGS. 3A-3C are a set of graphs illustrating that MSM sensitizes MRSA to multiple antibiotics. In vitro survival of ATCC strain 43300 *Staphylococcus aureus* (a MRSA strain resistant to oxacillin and methicillin), was tested in the presence of MSM and oxacillin or MSM and methicillin ATCC strain 43300 *staphylococcus aureus* was incubated 5-16% MSM in combination with 6 µg/ml oxacillin or 6 µg/ml methicillin. The initial inoculation of bacteria was $2.13 \times 10^6$/ml (Log=6.3). The growth periods tested were 24 hours (FIG. 3A), 48 hours (FIG. 3B) and 5 days (FIG. 3C). This is the MIC for oxacillin and methicillin for this strain of bacteria. An additional 3.5 MSM and 6 µg/ml oxacillin or 6 µg/ml methicillin was added each day. At 24 hours, 5% MSM and antibiotic showed the lowest level of bacterial survival. At 48 hours, 5% MSM and methicillin or 8% MSM and oxacillin showed the lowest level of bacterial survival. At five days, 13-16% MSM and antibiotic showed the lowest level of bacterial survival. Overall, the results indicate that MSM increased the sensitivity of this MRSA strain to both oxacillin and methicillin.
Figure 3B:
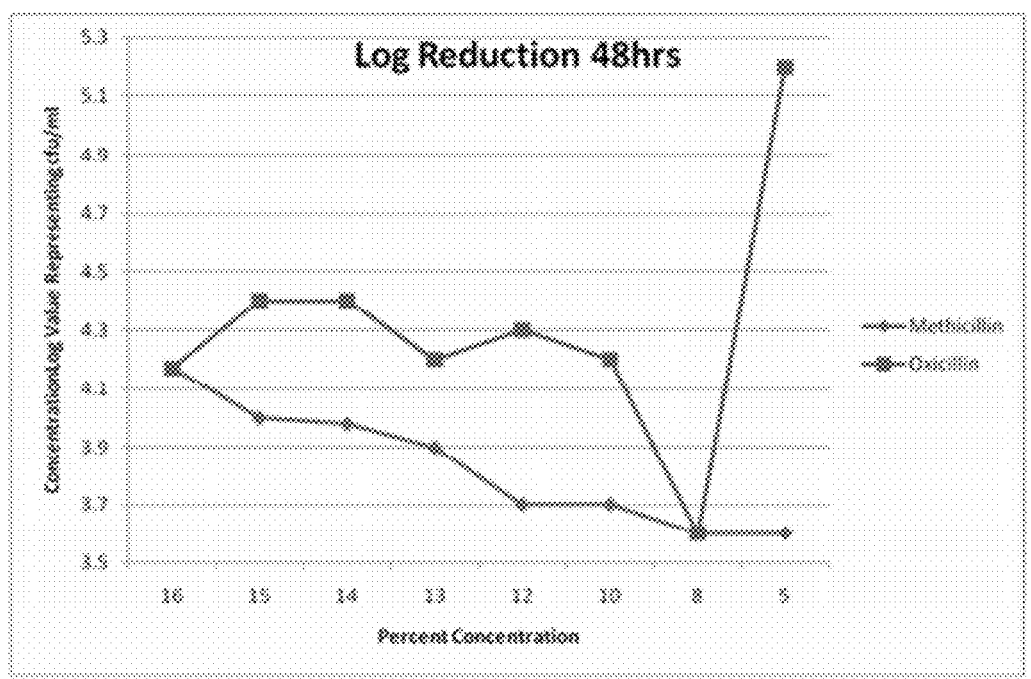
Figure 3C:
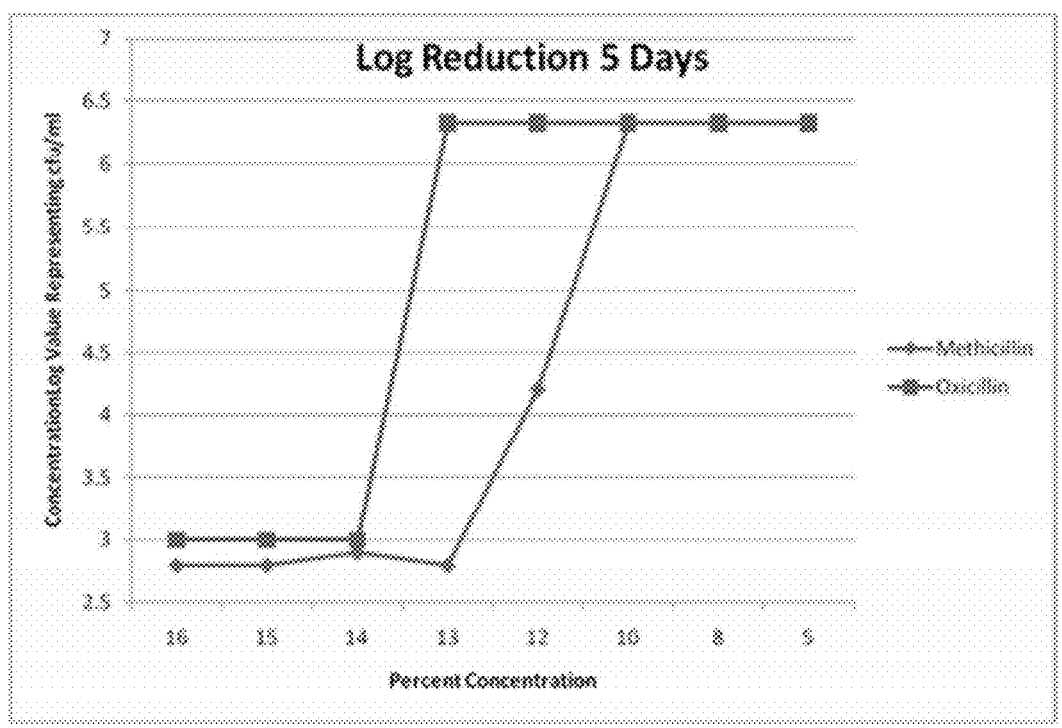

This example describes in vitro experiments testing the survival of ATCC strain 43300 *Staphylococcus aureus* (a methicillin and oxacillin resistant strain) in the presence of MSM and oxacillin or MSM and methicillin. The growth periods tested were 24 hours, 48 hours and 5 days. 5-16% MSM in combination with 6 µg/ml oxacillin or 6 µg/ml methicillin was tested. This is the MIC for oxacillin and methicillin for this strain of bacteria. An additional 3.5% MSM and 6 µg/ml oxacillin or 6 µg/ml methicillin was added each day. Results are shown in FIGS. 3A-3C. At 24 hours, 5% MSM and antibiotic showed the lowest level of bacterial survival. At 48 hours, 5% MSM and methicillin or 8% MSM and oxacillin showed the lowest level of bacterial survival. At 5 days, 13-16% MSM and antibiotic showed the lowest level of bacterial survival. Overall, the results indicate that MSM increased the sensitivity of this MRSA strain to both oxacillin and methicillin Methods:

USP<51> Antimicrobial Effectiveness protocol was used as the template experimental paradigm. Initial MSM concentrations tested were 5, 8, 10, 12, 13, 14, 15, and 16% MSM. All concentrations were plated out to the $10^{-7}$ dilutionsto ascertain cfu/ml. The initial concentration of oxacillin and methicillin used was 6 µg/ml, which is the MIC for oxacillin. This concentration is the industry standard for determining MRSA resistance in clinical applications. An additional 3.5% MSM and 6 µg/ml oxacillin or 6 µg/ml methicillin was added daily.

Materials used were Flake OptiMSM® MSM (lot number 0604751), ATCC strain 43300 *Staphylococcus aureus*, 30 ml Borosilicate glass cultures tubes, Lactose Broth (LB; Alpha Biosciences; Lot: L07-03), Modified Letheen Broth (MLB, Alpha Biosciences, lot I08-09), Trypto Soy Agar with Lecithin and Tween 80 (TSA; Alpha Biosciences, lot: F08-42), oxacillin sodium USP grade lot J and methicillin sodium (AS; Cat No. 1410002, lot KOH338).

Flake OptiMSM® MSM was weighed out on a certified Mettler Toledo AG245 SN: 1115210833 and aliquoted for each concentration. The MSM was placed into 30 ml borosilicate glass culture tubes. MSM was added to tubes as follows: 5% (0.5 g), 8% (0.8 g), 10% (1.0 g), 12% (1.2 g), 13% (1.3 g), 14% (1.4 g), 15% (1.5 g), 16% (1.6 g). Material was calculated on a 10 ml volume. Sterile oxacillin or methicillin was added to each experimental condition daily at 300 µl from a 30 mg/10 ml concentration giving it an initial final concentration of 6 µg/ml. An additional 3.5% MSM and 6 µg/ml was added each day.

All tubes were inoculated with a dilution of MRSA giving a final level of colony forming units of $2.13 \times 10^6$/ml (Log=6.3). The tubes were incubated at 25° C. and mixed periodically. Plating was done at 24 hours, 48 hours and 5 days. Each condition was plated by diluting 1 ml of growth material into 9 ml of MLB diluent broth. This mixture was serial diluted down to $10^{-7}$, and 1 ml placed in a sterile petri dish at each dilution point. 20 mls of TSA was added to each dilution, swirled and allowed to solidify. All dilutions were placed in a 35° C. incubator for 24 hours. Bacterial colonies on each plate were counted and colony counts changed into log format. A positive and negative control was ascertained.

Results:

The results of this study are shown in Table 3.

TABLE 3

ATCC strain 43300 Staphylococcus aureus survival in 5-16% MSM and oxacillin or methicillin for 24, 48 and 120 hours.

| % MSM | 6 µg/ml methicillin MSM (Log cfu/ml) | 6 µg/ml oxacillin MSM (Log cfu/ml) |
|---|---|---|
| 24 hours | | |
| 16 | 5.00 | 5.25 |
| 15 | 5.00 | 5.23 |
| 14 | 4.90 | 5.20 |
| 13 | 4.90 | 5.00 |
| 12 | 4.60 | 5.20 |
| 10 | 4.40 | 5.00 |
| 8 | 4.50 | 5.00 |
| 5 | 4.30 | 4.90 |
| 48 Hours | | |
| 16 | 4.17 | 4.17 |
| 15 | 4.00 | 4.40 |
| 14 | 3.98 | 4.40 |
| 13 | 3.90 | 4.20 |
| 12 | 3.70 | 4.30 |
| 10 | 3.70 | 4.20 |
| 8 | 3.60 | 3.60 |
| 5 | 3.60 | 5.20 |
| 120 hours | | |
| 16 | 2.80 | 3.00 |
| 15 | 2.80 | 3.00 |
| 14 | 2.90 | 3.00 |
| 13 | 2.80 | TNTC |
| 12 | 4.20 | TNTC |
| 10 | TNTC | TNTC |
| 8 | TNTC | TNTC |
| 5 | TNTC | TNTC |

The results of this study show that MSM increased the sensitivity of a MRSA strain to both oxacillin and methicillin. At 24 hours, fewer cfu/ml were observed with MSM and methicillin than MSM and oxacillin, across all MSM concentrations tested. Because the MIC for both methicillin and oxacillin is the same for this MRSA strain (6 µg/ml), this result suggests that MSM increases methicillin sensitivity more than oxacillin sensitivity. At 24 hours, 5% MSM and antibiotic showed the lowest level of bacterial survival.

Similar results were observed at 48 hours. At this time point, the average log reduction in cfu/ml observed for methicillin was 2.7 (initial 5% MSM) to 2.1 (initial 16% MSM) and for oxacillin 2.7 (initial 8% MSM) to 2.1 (initial 16% MSM). At 48 hours, 5% MSM and methicillin or 8% MSM and oxacillin showed the lowest level of bacterial survival. At 48 hours, bacterial survival was the same in the initial 8% MSM and either oxacillin or methicillin conditions.

At 120 hours, the initial 14-16% MSM and oxacillin conditions and the initial 13-16% MSM and methicillin conditions showed a Log reduction in cfu/ml of ~3.3-3.5 respectively. The initial 5-10% MSM and methicillin and the initial 13% MSM and oxacillin showed colony counts that were too numerous to count (TNTC). The 13-16% MSM and antibiotic showed the lowest level of bacterial survival.

Overall, these results show that MSM can increase the sensitivity of a MRSA strain of bacterial to methicillin and oxacillin. The results also suggest that a combination of methicillin and MSM is more effective at sensitizing the MRSA strain than a combination of MSM and oxacillin. One purely hypothetical explanation for these results is that the MSM molecule is somehow overcoming the antibiotic resistance, possibly by penetration, or by carrying the antibiotic into the cell. Another purely hypothetical conclusion is that methicillin may be binding to the MSM and being carried into the MRSA cell directly due to a higher number of MSM binding sites compared to oxacillin We observed that at the 24 and 48 hour time points, lower concentrations of MSM with antibiotic had a greater effect on bacterial survival than at the 5 day time point. One purely hypothetical and non-limiting explanation for this is that the concentration of MSM in the test tube is decreasing over time, possibly do to action by the bacteria.

Example 5

MSM Sensitizes MRSA to Multiple Antibiotics

This example describes preliminary in vitro experiments testing the survival of ATCC strain 43300 *Staphylococcus aureus* (a MRSA strain resistant to oxacillin and methicillin), in the presence of MSM and oxacillin or MSM and methicillin. Three different concentrations of these two antibiotics were tested: 12, 30 and 60 µg/ml, corresponding to 2×, 5× and 10×MIC for this strain of MRSA for each antibiotic. ATCC strain 43300 *staphylococcus aureus* was incubated with 5-16% MSM and the indicated amount of antibiotic for 24, 48 or 96 hours at 25° C.

Methods:

USP<51> Antimicrobial Effectiveness protocol was used as the template experimental paradigm. Initial MSM concentrations tested were 5-16% in increments of one. All concentrations were plated out to the $10^{-7}$ dilutions to ascertain cfu/ml. The initial concentration of oxacillin and methicillin used was 12, 30 or 60 µg/ml, which corresponds to 2×, 5× and 10×MIC for oxacillin. This concentration is the industry standard for determining MRSA resistance in clinical applications.

Materials used were Flake OptiMSM® MSM (lot number 0604751), ATCC strain 43300 *Staphylococcus aureus*, 30 ml Borosilicate glass cultures tubes, Lactose Broth (LB; Alpha Biosciences; Lot: L07-03), Modified Letheen Broth (MLB, Alpha Biosciences, lot I08-09), Trypto Soy Agar with Lecithin and Tween 80 (TSA; Alpha Biosciences, lot: F08-42), oxacillin sodium USP grade lot J and methicillin sodium (AS; Cat No. 1410002, lot KOH338).

ATCC strain 43300 *Staphylococcus aureus* was streaked out for isolations and 25 clones were picked and diluted to a McFarland standard of one. The estimated value was then taken to inoculate tubes containing growth media and 12, 30 or 60 µg/ml methicillin or oxacillin with around $10^{-7}$ cfu/ tube. A clone demonstrating turbid growth in 24 hours in all concentrations of antibiotic was selected for the rest of the experiment.

Flake OptiMSM® MSM was weighed out on a certified Mettler Toledo AG245 SN: 1115210833 and aliquoted for each concentration. The MSM was placed into 30 ml borosilicate glass culture tubes. MSM was added to tubes as follows: 5% (0.5 g), 6% (0.6 g), 7% (0.7 g), 8% (0.8 g), 9% (0.9 g), 10% (1.0 g), 11% (1.1 g), 12% (1.2 g), 13% (1.3 g), 14% (1.4 g), 15% (1.5 g), and 16% (1.6 g). Material was calculated on a 10 ml volume. Sterile oxacillin or methicillin was added to each experimental condition to a final concentration of 12, 30 or 60 µg/ml antibiotic. Control conditions of 5-16% MSM and no antibiotic were tested for MRSA survival. Control conditions with 12, 30 or 60 µg/ml antibiotic, but no MSM were tested for MRSA growth.

All tubes were then inoculated with a dilution of the selected ATCC strain 43300 *Staphylococcus aureus* clone giving a final level of colony forming units of $9.4 \times 10^7$/ml (log=7.97). The tubes were incubated at 25° C. and mixed periodically. An additional 3.5% MSM as well as the initial amount of antibiotic, was added to the tubes daily. Plating was done at 24 hours. Each condition was plated by diluting 1 ml of growth material into 9 ml of MLB diluent broth. This mixture was serial diluted down to $10^{-7}$, and 1 ml placed in a sterile petri dish at each dilution point. 20 mls of TSA was added to each dilution, swirled and allowed to solidify. All dilutions were placed in a 35° C. incubator for 24 hours. Bacterial colonies on each plate were counted and colony counts changed into log format. A positive and negative control was ascertained.

Results:

The results of this study are shown in Table 4 and FIGS. 3A-C.

TABLE 4

ATCC strain 43300 *Staphylococcus aureus* survival in 5-16% MSM and 12, 30 or 60 µg/ml oxacillin or methicillin for 24 hours.

| % MSM | 12 µg/ml methicillin MSM (Log cfu/ml) | 12 µg/ml oxacillin MSM (Log cfu/ml) |
|---|---|---|
| 16 | 4.56 | 4.77 |
| 15 | 4.7 | 4.93 |
| 14 | 4.7 | 4.88 |
| 13 | 4.77 | 4.9 |
| 12 | 4.89 | 4.8 |
| 11 | 4.87 | 4.8 |
| 10 | 4.8 | 4.96 |
| 9 | 4.99 | 5.16 |
| 8 | 5.0 | 5.18 |
| 7 | 5.46 | 5.18 |
| 6 | 5.2 | 5.26 |
| 5 | 5.43 | 5.28 |

| % MSM | 30 µg/ml methicillin MSM (Log cfu/ml) | 30 µg/ml oxacillin MSM (Log cfu/ml) |
|---|---|---|
| 16 | 4.47 | 4.59 |
| 15 | 4.54 | 4.74 |
| 14 | 4.6 | 4.82 |
| 13 | 4.7 | 4.9 |
| 12 | 4.7 | 4.87 |
| 11 | 4.8 | 4.94 |
| 10 | 4.8 | 4.99 |
| 9 | 5.07 | 5.02 |
| 8 | 5.09 | 5.2 |
| 7 | 5.13 | 5.12 |
| 6 | 5.18 | 5.15 |
| 5 | 5.3 | 5.17 |

TABLE 4-continued

ATCC strain 43300 *Staphylococcus aureus* survival in 5-16% MSM and 12, 30 or 60 μg/ml oxacillin or methicillin for 24 hours.

| % MSM | 60 μg/ml methicillin MSM (Log cfu/ml) | 60 μg/ml oxacillin MSM (Log cfu/ml) |
|---|---|---|
| 16 | 4.8 | 4.6 |
| 15 | 4.65 | 4.75 |
| 14 | 4.77 | 4.8 |
| 13 | 4.77 | 4.83 |
| 12 | 4.68 | 4.77 |
| 11 | 4.66 | 4.8 |
| 10 | 4.66 | 4.87 |
| 9 | 4.9 | 4.95 |
| 8 | 5.1 | 5.0 |
| 7 | 5.0 | 5.14 |
| 6 | 5.2 | 5.12 |
| 5 | 5.2 | 5.2 |

The observed log reduction in cfu/ml was similar for all antibiotic concentrations. The average log reduction in cfu/ml for 5% MSM with antibiotic was 2.2, whereas the average log reduction in cfu/ml for 16% MSM with antibiotic was 3.3 (baring the methicillin 60 μg/ml outlier). The overall effectiveness of methicillin was slightly better than the oxacillin Overall, greater sensitivity to the antibiotic was observed as higher MSM concentrations. The MSM without antibiotic control condition exhibited greater colony numbers than what was initially inoculated. Control conditions with antibiotic, but without MSM, showed TNTC, demonstrating no inhibition with antibiotic alone.

The results from the 48 and 96 hour time points showed that all cultures at these time points were too numerous to count. This can be explained by the use of a clone that had great growth in all three antibiotic concentrations, selecting for a more resistant strain of MRSA then is obtained in nature. Adding to this would be the higher inoculation value of 9.4× $10^7$/ml (log=7.97); normally, the inoculation should be between $10^4$ to $10^6$ cfu/ml. A purely hypothetical, non-limiting explanation for this is that under these experimental conditions, any the effect of MSM and antibiotic on bacterial survival is masked by other factors. Alternatively, the antibiotic could have been degraded as well since we used it for the last experiment over a long period of time.

These results show that MSM increased the sensitivity of ATCC strain 43300 *Staphylococcus aureus* to both oxacillin and methicillin at a 24 hour time point; however, the results are inconclusive at other time points. At the 24 hour time point, the increased sensitivity was observed at all concentrations of antibiotic tested, and at all concentrations of MSM tested. Higher concentrations of MSM increased antibiotic sensitivity to a greater extent than lower concentrations of MSM. A difference between this and previous experiments is that we selected for a clone to meet growth requirements of all three concentrations of antibiotic.

Example 6

Effect of MSM and 12, 30, or 60 μg/ml Oxacillin on MRSA

This example describes an in vitro experiment testing the survival of ATCC strain 43300 *Staphylococcus aureus* in the presence of 5-16% MSM and an initial concentration of 12, or 60 μg/ml oxacillin. These correspond to 2×, 5× and 10×MIC for oxacillin. Additional antibiotic was added every 24 hours. The growth periods tested were 24 (see FIG. 4), 48, 72, 96 and 120 hours. The results show that MSM sensitized a MRSA strain to oxacillin. At the earliest time points (24 and 48 hours), the results show decreased bacterial survival, indicating increased oxacillin sensitivity, at all concentrations of antibiotic tested, and at all concentrations of MSM tested. However, at later time points (96 and 120 hours), decreased bacterial survival was only observed at higher MSM concentrations (10-16% MSM), indicating that MSM-induced oxacillin sensitivity is time dependent. The results also show that, at later time points, a high concentration of oxacillin correlated with decreased bacterial survival.

Methods:

USP<51> Antimicrobial Effectiveness protocol was used as the template experimental paradigm. Initial MSM concentrations tested were 5-16% in increments of one. All concentrations were plated out to the $10^{-7}$ dilutionsto ascertain cfu/ml. The initial concentration of oxacillin used was 12, 30 or 60 μg/ml, which corresponds to 2×, 5× and 10×MIC for oxacillin. Additional antibiotic was added at the initial concentration every 24 hours.

Materials used were Flake OptiMSM® MSM (lot number 0604751), ATCC strain 43300 *Staphylococcus aureus*, 30 ml Borosilicate glass cultures tubes, Lactose Broth (LB; Alpha Biosciences; Lot: L07-03), Modified Letheen Broth (MLB, Alpha Biosciences, lot I08-09), Trypto Soy Agar with Lecithin and Tween 80 (TSA; Alpha Biosciences, lot: F08-42) and oxacillin sodium USP grade lot J.

ATCC strain 43300 *Staphylococcus aureus* was streaked out for isolations. An isolated colony was chosen, streaked again and incubated. Isolate was chosen and then diluted to a McFarland standard of one. The estimated value was then taken to inoculate tubes containing growth media and 12, 30 or 60 μg/ml oxacillin with approximately $10^5$ cfu/ml. These tubes were incubated and plated for counting cfu. A clone having no observed log reduction in cfu was selected for the rest of the experiment.

Flake OptiMSM® MSM was weighed out on a certified Mettler Toledo AG245 SN: 1115210833 and aliquoted for each concentration. The MSM was placed into 30 ml borosilicate glass culture tubes. MSM was added to tubes as follows: 5% (0.5 g), 6% (0.6 g), 7% (0.7 g), 8% (0.8 g), 9% (0.9 g), 10% (1.0 g), 11% (1.1 g), 12% (1.2 g), 13% (1.3 g), 14% (1.4 g), 15% (1.5 g), and 16% (1.6 g). Material was calculated on a 10 ml volume. Sterile oxacillin was added to each experimental condition to a final concentration of 12, 30 or 60 μg/ml antibiotic. Control conditions with 5, 10 and 16% MSM and no antibiotic, or no MSM and 12, 30 or 60 μg/ml antibiotic, were tested.

All tubes were then inoculated with a dilution of the selected ATCC strain 43300 *Staphylococcus aureus* clone giving a final level of colony forming units of 3.3×$10^5$/ml (log=5.52). The tubes were incubated at 25° C. and mixed periodically. Antibiotic was re-inoculated every 24 hours at the initial concentration to maintain pressure on the organism. Plating was done at 24, 48, 72, and 120 hours. Each condition was plated by diluting 1 ml of growth material into 9 ml of MLB diluent broth. Each time this was done, 1 ml of MSM-containing growth media was added back to the tube to maintain a constant volume and MSM concentration. This mixture was serial diluted down to $10^{-7}$ with 1 ml placed in triplicate in a sterile petri dish at each dilution point. 20 mls of TSA was added to each dilution, swirled and allowed to solidify. All dilutions were placed in a 35° C. incubator for 24 to 72 hours. Bacterial colonies on each plate were counted and the average taken then changed into log format. Any cfu/ml observed greater than 3.3×$10^5$ (log=5.5) were recorded as >3.3×$10^5$.

Results:

Positive controls (those inoculated with MRSA) for the three concentrations of oxacillin alone used in this experiment (12 µg/ml, 30 µg/ml and 60 µg/ml) showed no significant decrease in colony forming units from the initial inoculums value. The results of this study are shown in Tables 5-9.

TABLE 5

ATCC strain 43300 *Staphylococcus aureus* survival in 5-16% MSM and 12, 30 or 60 µg/ml oxacillin for 24 hours.

| % MSM | 12 µg/ml oxacillin MSM (cfu/ml) | 12 µg/ml oxacillin MSM (cfu/ml) | 12 µg/ml oxacillin MSM (cfu/ml) | 24 hours Average Log |
|---|---|---|---|---|
| 16 | $7.6 \times 10^3$ | $7.4 \times 10^3$ | $7.6 \times 10^3$ | 3.88 |
| 15 | $1.35 \times 10^4$ | $1.30 \times 10^4$ | $1.29 \times 10^4$ | 4.11 |
| 14 | $1.00 \times 10^4$ | $1.02 \times 10^4$ | $1.01 \times 10^4$ | 4.00 |
| 13 | $9.0 \times 10^3$ | $8.7 \times 10^3$ | $9.2 \times 10^3$ | 3.95 |
| 12 | $7.0 \times 10^3$ | $7.0 \times 10^3$ | $7.3 \times 10^3$ | 3.85 |
| 11 | $8.2 \times 10^3$ | $8.5 \times 10^3$ | $8.0 \times 10^3$ | 3.91 |
| 10 | $5.8 \times 10^3$ | $5.6 \times 10^3$ | $6.0 \times 10^3$ | 3.76 |
| 9 | $5.6 \times 10^3$ | $5.2 \times 10^3$ | $5.0 \times 10^3$ | 3.72 |
| 8 | $6.6 \times 10^3$ | $6.6 \times 10^3$ | $6.9 \times 10^3$ | 3.82 |
| 7 | $8.2 \times 10^3$ | $8.5 \times 10^3$ | $8.3 \times 10^3$ | 3.91 |
| 6 | $8.6 \times 10^3$ | $8.5 \times 10^3$ | $8.0 \times 10^3$ | 3.92 |
| 5 | $8.4 \times 10^3$ | $8.0 \times 10^3$ | $8.0 \times 10^3$ | 3.91 |
| 0 | $>3.3 \times 10^5$ | $>3.3 \times 10^5$ | $>3.3 \times 10^5$ | 5.5 |

| % MSM | 30 µg/ml oxacillin MSM (cfu/ml) | 30 µg/ml oxacillin MSM (cfu/ml) | 30 µg/ml oxacillin MSM (cfu/ml) | 24 hours Average Log |
|---|---|---|---|---|
| 16 | $8.3 \times 10^3$ | $8.3 \times 10^3$ | $8.0 \times 10^3$ | 3.91 |
| 15 | $8.7 \times 10^3$ | $8.9 \times 10^3$ | $8.8 \times 10^3$ | 3.94 |
| 14 | $6.1 \times 10^3$ | $6.0 \times 10^3$ | $6.0 \times 10^3$ | 3.78 |
| 13 | $4.4 \times 10^3$ | $4.1 \times 10^3$ | $4.2 \times 10^3$ | 3.62 |
| 12 | $3.9 \times 10^3$ | $3.9 \times 10^3$ | $3.9 \times 10^3$ | 3.59 |
| 11 | $3.9 \times 10^3$ | $3.7 \times 10^3$ | $3.7 \times 10^3$ | 3.57 |
| 10 | $2.2 \times 10^3$ | $2.2 \times 10^3$ | $2.0 \times 10^3$ | 3.32 |
| 9 | $1.06 \times 10^3$ | $1.05 \times 10^3$ | $1.02 \times 10^3$ | 3.01 |
| 8 | $1.18 \times 10^3$ | $1.18 \times 10^3$ | $1.16 \times 10^3$ | 3.07 |
| 7 | $9.7 \times 10^2$ | $9.6 \times 10^2$ | $9.2 \times 10^2$ | 2.98 |
| 6 | $2.9 \times 10^2$ | $2.9 \times 10^2$ | $2.9 \times 10^2$ | 2.46 |
| 5 | $3.1 \times 10^2$ | $3.3 \times 10^2$ | $3.3 \times 10^2$ | 2.51 |
| 0 | $>3.3 \times 10^5$ | $>3.3 \times 10^5$ | $>3.3 \times 10^5$ | 5.5 |

| % MSM | 60 µg/ml oxacillin MSM (cfu/ml) | 60 µg/ml oxacillin MSM (cfu/ml) | 60 µg/ml oxacillin MSM (cfu/ml) | 24 hours Average Log |
|---|---|---|---|---|
| 16 | $6.9 \times 10^3$ | $6.9 \times 10^3$ | $6.9 \times 10^3$ | 3.83 |
| 15 | $6.6 \times 10^3$ | $6.2 \times 10^3$ | $6.4 \times 10^3$ | 3.81 |
| 14 | $1.8 \times 10^2$ | $1.7 \times 10^2$ | $1.8 \times 10^2$ | 2.03 |
| 13 | $6.3 \times 10^2$ | $6.0 \times 10^2$ | $6.0 \times 10^2$ | 2.80 |
| 12 | $7.3 \times 10^2$ | $7.1 \times 10^2$ | $7.5 \times 10^2$ | 2.86 |
| 11 | $6.7 \times 10^2$ | $6.7 \times 10^2$ | $6.9 \times 10^2$ | 2.83 |
| 10 | $4.2 \times 10^2$ | $4.4 \times 10^2$ | $4.4 \times 10^2$ | 2.63 |
| 9 | $3.2 \times 10^2$ | $3.2 \times 10^2$ | $3.2 \times 10^2$ | 2.50 |
| 8 | $4.6 \times 10^2$ | $4.6 \times 10^2$ | $5.0 \times 10^2$ | 2.67 |
| 7 | $2.1 \times 10^2$ | $2.3 \times 10^2$ | $2.1 \times 10^2$ | 2.34 |
| 6 | $2.4 \times 10^2$ | $2.4 \times 10^2$ | $2.4 \times 10^2$ | 2.38 |
| 5 | $3.5 \times 10^2$ | $3.3 \times 10^2$ | $3.6 \times 10^2$ | 2.54 |
| 0 | $>3.3 \times 10^5$ | $>3.3 \times 10^5$ | $>3.3 \times 10^5$ | 5.5 |

Figure 4:
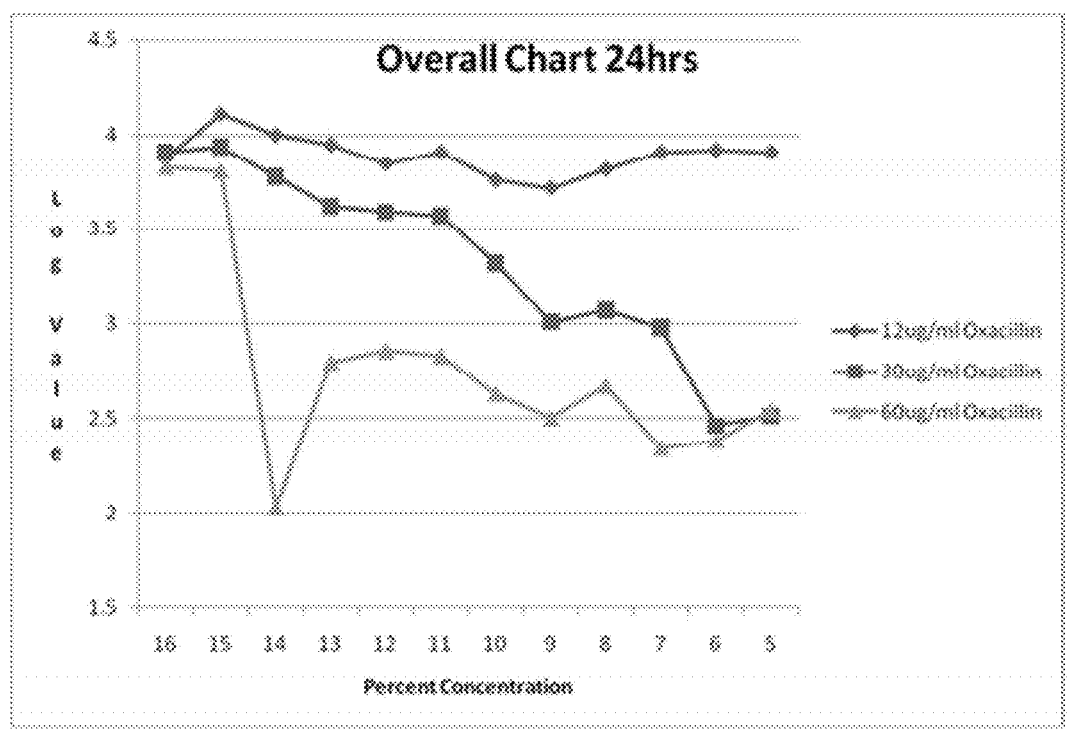
FIG. 4 is a graph illustrating that MSM sensitizes MRSA to multiple concentrations of oxacillin. In vitro survival of ATCC strain 43300 *staphylococcus aureus* (a MRSA strain resistant to oxacillin and methicillin), was tested in the presence of MSM and oxacillin. Three different concentrations of oxacillin were tested, corresponding to 2×, 5× and 10×MIC for this strain of MRSA for each antibiotic. ATCC strain 43300 *staphylococcus aureus* was incubated with 5-16% MSM and the indicated amount of antibiotic for 24 hours at 25° C. Thus, the bacteria were under 2×, 5×, or 10×MIC concentrations of oxacillin for 24 hours. The initial inoculation of bacteria was $3.3 \times 10^5$/ml (log=5.52). At this time point, lower concentrations of MSM with antibiotic had a greater effect on bacterial survival than higher concentrations of MSM. However, overall, these results confirm that MSM sensitizes MRSA to oxacillin.

As shown in Table 5 and FIG. 4, the number of cfu/ml observed at the 24 hour time point was similar between all oxacillin concentrations. The lower MSM concentrations had higher log reduction in colony count then the higher MSM concentrations. The average log reduction in the number of cfu/ml for 12 µg/ml oxacillin is 1.5 logs which carried throughout all the concentrations with little or no change. The 30 µg/ml and 60 µg/ml conditions had a Log reduction in the number of cfu/ml on the lower end of MSM concentrations, being an average of a 3 log difference. The 60 µg/ml condition demonstrated the greatest log reduction in the number of cfu/ml in the first 24 hour period of the three concentrations of oxacillin. The 60 µg/ml oxacillin condition at 14% MSM had a 3.5 log reduction in the number of cfu/ml. Negative LB controls showed no signs of contamination. LB positive controls showed turbid growth. The negative 5%, 10%, and 16% MSM controls had no signs of contamination. The positive 5%, 10%, and 16% MSM controls had signs of turbid growth. The oxacillin controls showed no signs of significant reduction from the initial inoculums, and the negative controls showed no signs of contamination.

TABLE 6

ATCC strain 43300 *Staphylococcus aureus* survival in 5-16% MSM and 12, 30 or 60 µg/ml oxacillin for 48 hours.

| % MSM | 12 µg/ml oxacillin MSM (cfu/ml) | 12 µg/ml oxacillin MSM (cfu/ml) | 12 µg/ml oxacillin MSM (cfu/ml) | 48 hours Average Log |
|---|---|---|---|---|
| 16 | $4.2 \times 10^3$ | $5.0 \times 10^3$ | $4.3 \times 10^3$ | 3.7 |
| 15 | $5.0 \times 10^3$ | $4.5 \times 10^3$ | $4.6 \times 10^3$ | 3.7 |
| 14 | $1.0 \times 10^1$ | $1.2 \times 10^1$ | $1.1 \times 10^1$ | 1.0 |
| 13 | $6.8 \times 10^2$ | $6.8 \times 10^2$ | $5.8 \times 10^2$ | 2.8 |
| 12 | $3.6 \times 10^2$ | $4.0 \times 10^2$ | $4.2 \times 10^2$ | 2.8 |
| 11 | $6.4 \times 10^2$ | $5.8 \times 10^2$ | $6.5 \times 10^2$ | 2.8 |
| 10 | $5.6 \times 10^2$ | $5.4 \times 10^2$ | $5.4 \times 10^2$ | 2.7 |
| 9 | $2.4 \times 10^3$ | $2.5 \times 10^3$ | $2.3 \times 10^3$ | 3.4 |
| 8 | $4.9 \times 10^3$ | $4.9 \times 10^3$ | $5.4 \times 10^3$ | 3.7 |
| 7 | $9.0 \times 10^3$ | $8.9 \times 10^3$ | $8.5 \times 10^3$ | 3.9 |
| 6 | $1.7 \times 10^3$ | $1.4 \times 10^3$ | $1.7 \times 10^3$ | 3.2 |
| 5 | $4.5 \times 10^3$ | $4.0 \times 10^3$ | $4.3 \times 10^3$ | 3.6 |
| 0 | $>3.3 \times 10^5$ | $>3.3 \times 10^5$ | $>3.3 \times 10^5$ | 5.5 |

| % MSM | 30 µg/ml oxacillin MSM (cfu/ml) | 30 µg/ml oxacillin MSM (cfu/ml) | 30 µg/ml oxacillin MSM (cfu/ml) | 48 hours Average Log |
|---|---|---|---|---|
| 16 | $4.6 \times 10^2$ | $4.0 \times 10^2$ | $4.1 \times 10^2$ | 2.6 |
| 15 | $6.2 \times 10^2$ | $6.4 \times 10^2$ | $6.4 \times 10^2$ | 2.8 |
| 14 | $3.6 \times 10^2$ | $3.2 \times 10^2$ | $3.5 \times 10^2$ | 2.5 |
| 13 | $3.0 \times 10^2$ | $3.1 \times 10^2$ | $3.1 \times 10^2$ | 2.5 |
| 12 | $3.9 \times 10^2$ | $3.6 \times 10^2$ | $4.0 \times 10^2$ | 2.6 |
| 11 | $2.5 \times 10^2$ | $2.7 \times 10^2$ | $2.8 \times 10^2$ | 2.4 |
| 10 | $4.3 \times 10^2$ | $4.3 \times 10^2$ | $4.0 \times 10^2$ | 2.6 |
| 9 | $2.8 \times 10^2$ | $2.6 \times 10^2$ | $2.2 \times 10^2$ | 2.4 |
| 8 | $1.23 \times 10^3$ | $1.24 \times 10^3$ | $1.20 \times 10^3$ | 3.1 |
| 7 | $2.0 \times 10^2$ | $2.1 \times 10^2$ | $2.2 \times 10^2$ | 2.3 |
| 6 | $5.5 \times 10^3$ | $5.5 \times 10^3$ | $5.9 \times 10^3$ | 3.7 |
| 5 | $5.8 \times 10^3$ | $6.0 \times 10^3$ | $5.9 \times 10^3$ | 3.8 |
| 0 | $>3.3 \times 10^5$ | $>3.3 \times 10^5$ | $>3.3 \times 10^5$ | 5.5 |

| % MSM | 60 µg/ml oxacillin MSM (cfu/ml) | 60 µg/ml oxacillin MSM (cfu/ml) | 60 µg/ml oxacillin MSM (cfu/ml) | 48 hours Average Log |
|---|---|---|---|---|
| 16 | $9.0 \times 10^1$ | $9.0 \times 10^1$ | $6.0 \times 10^1$ | 1.9 |
| 15 | $1.2 \times 10^2$ | $1.3 \times 10^2$ | $1.2 \times 10^2$ | 2.1 |
| 14 | $1.5 \times 10^2$ | $1.7 \times 10^2$ | $1.2 \times 10^2$ | 2.2 |
| 13 | $6.0 \times 10^1$ | $4.0 \times 10^1$ | $5.0 \times 10^1$ | 1.7 |
| 12 | $1.1 \times 10^2$ | $1.0 \times 10^2$ | $1.0 \times 10^2$ | 2.0 |
| 11 | $1.3 \times 10^2$ | $1.7 \times 10^2$ | $1.2 \times 10^2$ | 2.1 |
| 10 | $1.6 \times 10^2$ | $1.4 \times 10^2$ | $1.6 \times 10^2$ | 2.2 |
| 9 | $1.8 \times 10^2$ | $1.7 \times 10^2$ | $1.5 \times 10^2$ | 2.2 |
| 8 | $7.5 \times 10^2$ | $7.3 \times 10^2$ | $7.0 \times 10^2$ | 2.8 |
| 7 | $1.0 \times 10^4$ | $1.1 \times 10^4$ | $1.1 \times 10^4$ | 4.0 |
| 6 | $6.0 \times 10^1$ | $5.0 \times 10^1$ | $6.0 \times 10^1$ | 1.8 |
| 5 | $3.0 \times 10^3$ | $2.7 \times 10^3$ | $3.3 \times 10^3$ | 3.5 |
| 0 | $>3.3 \times 10^5$ | $>3.3 \times 10^5$ | $>3.3 \times 10^5$ | 5.5 |

As shown in Table 6, the number of cfu/ml observed at the 48 hour time point was similar between all oxacillin concentrations. A trend with most of the lower MSM concentrations having a lower log reduction in the number of cfu/ml then the higher MSM concentrations across all oxacillin concentrations, was observed. The 30 µg/ml and 60 µg/ml oxacillin conditions showed greater Log reduction in the number of cfu/ml at the 48 hour time point than the 24 hour time point at 8%-16% MSM concentrations. The 60 µg/ml oxacillin condition maintained a higher average log reduction in the number of cfu/ml compared to the corresponding 24 hour time points for all three concentrations of oxacillin Two points of interest are that the 14% MSM at 12 µg/ml oxacillin had a 4.5 log reduction in the number of cfu/ml and the 14% MSM at 60 µg/ml oxacillin showed only slightly greater Log reduction in the number of cfu/ml than the corresponding 24 hour time point. This could represent an optimal point for the oxacillin and MSM treatment. Negative LB controls showed no signs of contamination. LB positive controls showed turbid growth. The negative 5%, 10%, and 16% MSM controls had no signs of contamination. The oxacillin controls showed no signs of significant reduction from the initial inoculums, and the negative controls showed no signs of contamination.

TABLE 7

ATCC strain 43300 *Staphylococcus aureus* survival in 5-16% MSM and 12, 30 or 60 µg/ml oxacillin for 72 hours.

| % MSM | 12 µg/ml oxacillin MSM (cfu/ml) | 12 µg/ml oxacillin MSM (cfu/ml) | 12 µg/ml oxacillin MSM (cfu/ml) | 72 hours Average Log |
|---|---|---|---|---|
| 16 | $1.1 \times 10^2$ | $1.2 \times 10^2$ | $1.6 \times 10^2$ | 2.1 |
| 15 | $2.3 \times 10^2$ | $2.2 \times 10^2$ | $1.2 \times 10^2$ | 2.3 |
| 14 | $1.1 \times 10^2$ | $1.2 \times 10^2$ | $1.1 \times 10^2$ | 2.0 |
| 13 | $5.2 \times 10^2$ | $5.1 \times 10^2$ | $5.4 \times 10^2$ | 2.7 |
| 12 | $1.5 \times 10^3$ | $1.1 \times 10^3$ | $1.3 \times 10^3$ | 3.1 |
| 11 | $4.4 \times 10^3$ | $4.5 \times 10^3$ | $4.0 \times 10^3$ | 3.6 |
| 10 | $1.2 \times 10^4$ | $1.1 \times 10^4$ | $1.0 \times 10^4$ | 4.0 |
| 9 | $4.7 \times 10^4$ | $4.2 \times 10^4$ | $4.5 \times 10^4$ | 4.5 |
| 8 | $>3.3 \times 10^5$ | $>3.3 \times 10^5$ | $>3.3 \times 10^5$ | 5.5 |
| 7 | $>3.3 \times 10^5$ | $>3.3 \times 10^5$ | $>3.3 \times 10^5$ | 5.5 |
| 6 | $>3.3 \times 10^5$ | $>3.3 \times 10^5$ | $>3.3 \times 10^5$ | 5.5 |
| 5 | $>3.3 \times 10^5$ | $>3.3 \times 10^5$ | $>3.3 \times 10^5$ | 5.5 |
| 0 | $>3.3 \times 10^5$ | $>3.3 \times 10^5$ | $>3.3 \times 10^5$ | 5.5 |

| % MSM | 30 µg/ml oxacillin MSM (cfu/ml) | 30 µg/ml oxacillin MSM (cfu/ml) | 30 µg/ml oxacillin MSM (cfu/ml) | 72 hours Average Log |
|---|---|---|---|---|
| 16 | $9 \times 10^1$ | $8.0 \times 10^1$ | $8.0 \times 10^1$ | 1.9 |
| 15 | $2.3 \times 10^2$ | $2.2 \times 10^2$ | $2.8 \times 10^2$ | 2.4 |
| 14 | $1.4 \times 10^2$ | $1.7 \times 10^2$ | $1.8 \times 10^2$ | 2.2 |
| 13 | $9.0 \times 10^1$ | $8.0 \times 10^1$ | $4.0 \times 10^1$ | 1.8 |
| 12 | $4.8 \times 10^2$ | $3.9 \times 10^2$ | $4.9 \times 10^2$ | 2.6 |
| 11 | $1.2 \times 10^3$ | $1.7 \times 10^3$ | $1.5 \times 10^3$ | 3.2 |
| 10 | $8.9 \times 10^3$ | $9.0 \times 10^3$ | $8.5 \times 10^3$ | 3.9 |
| 9 | $8.8 \times 10^2$ | $8.1 \times 10^2$ | $8.5 \times 10^2$ | 2.9 |
| 8 | $>3.3 \times 10^5$ | $>3.3 \times 10^5$ | $>3.3 \times 10^5$ | 5.5 |
| 7 | $3.6 \times 10^4$ | $3.6 \times 10^4$ | $3.2 \times 10^4$ | 4.5 |
| 6 | $>3.3 \times 10^5$ | $>3.3 \times 10^5$ | $>3.3 \times 10^5$ | 5.5 |
| 5 | $>3.3 \times 10^5$ | $>3.3 \times 10^5$ | $>3.3 \times 10^5$ | 5.5 |
| 0 | $>3.3 \times 10^5$ | $>3.3 \times 10^5$ | $>3.3 \times 10^5$ | 5.5 |

| % MSM | 60 µg/ml oxacillin MSM (cfu/ml) | 60 µg/ml oxacillin MSM (cfu/ml) | 60 µg/ml oxacillin MSM (cfu/ml) | 72 hours Average Log |
|---|---|---|---|---|
| 16 | $6.0 \times 10^1$ | $6.0 \times 10^1$ | $5.0 \times 10^1$ | 1.8 |
| 15 | 0 | 0 | 0 | |
| 14 | $2.0 \times 10^1$ | $2.0 \times 10^1$ | $4.0 \times 10^1$ | 1.5 |
| 13 | $1.0 \times 10^1$ | $1.0 \times 10^1$ | $1.0 \times 10^1$ | 1 |
| 12 | $2.8 \times 10^2$ | $2.1 \times 10^2$ | $2.5 \times 10^2$ | 2.4 |
| 11 | $1.0 \times 10^1$ | $1.0 \times 10^1$ | $2.0 \times 10^1$ | 1 |
| 10 | $3.9 \times 10^2$ | $4.0 \times 10^2$ | $3.4 \times 10^2$ | 2.6 |
| 9 | $3.3 \times 10^3$ | $3.3 \times 10^3$ | $3.2 \times 10^3$ | 2.5 |

TABLE 7-continued

ATCC strain 43300 *Staphylococcus aureus* survival in 5-16% MSM and 12, 30 or 60 µg/ml oxacillin for 72 hours.

| 8 | $>3.3 \times 10^5$ | $>3.3 \times 10^5$ | $>3.3 \times 10^5$ | 5.5 |
|---|---|---|---|---|
| 7 | $>3.3 \times 10^5$ | $>3.3 \times 10^5$ | $>3.3 \times 10^5$ | 5.5 |
| 6 | $6.5 \times 10^2$ | $6.4 \times 10^2$ | $6.1 \times 10^2$ | 2.8 |
| 5 | $>3.3 \times 10^5$ | $>3.3 \times 10^5$ | $>3.3 \times 10^5$ | 5.5 |
| 0 | $>3.3 \times 10^5$ | $>3.3 \times 10^5$ | $>3.3 \times 10^5$ | 5.5 |

As shown in Table 7, the 15% MSM with 60 µg/ml oxacillin condition at 72 hours showed no sign of colonies. The tube was then taken out of the experiment and tested for ATCC strain 43300 *Staphylococcus* growth. The tube was spun down at 5000 rpm for 10 minutes. The supernatant was then decanted into 90 mls of Mueller-Hinton broth with 6 µg/ml oxacillin. This is for enrichment and the recovery of any MRSA cells that may be present whether healthy or stressed. The pellet had 10 mls Mueller-Hinton broth with 6 µg/ml oxacillin added to it to recover any cells that may be present. Both vessels were incubated at 35° C. for 48 hours followed by plating every 24 hours. Each vessel was plated at 10 dilutions to obtain a 1 cfu detection limit. No colonies were observed, indicating total kill. This time point for graphing purposes will be reported as 0 logs.

As shown in Table 7, the number of cfu/ml observed at the 72 hour time point was similar between all oxacillin concentrations. The 5-12% MSM conditions showed less average Log reduction in the number of cfu/ml at this time point than at earlier time points. This may demonstrate a reduction of MRSA sensitivity to oxacillin. If so, it the reduction correlates with MSM concentration (i.e. lower MSM conc.=higher oxacillin resistance). The 12 µg/ml oxacillin condition has a 1 log reduction in the number of cfu/ml for the MSM concentrations of 12%-16%. The 60 µg/ml oxacillin condition maintains a higher average log reduction in the number of cfu/ml among the three oxacillin concentrations which differs compared to the first 24 hr period. Two points of interest are that the 14% MSM at 12 µg/ml oxacillin condition showed a 4.5 log reduction in the number of cfu/ml and the 12% MSM at 60 µg/ml oxacillin condition showed a slightly higher Log reduction in the number of cfu/ml than the previous time point. This could represent an optimal point for the oxacillin treatment. Negative LB controls showed no signs of contamination. The negative 5% 10%, and 16% MSM controls had no signs of contamination. The oxacillin controls showed no signs of significant reduction from the initial inoculums, and the negative controls showed no signs of contamination.

TABLE 8

ATCC strain 43300 *Staphylococcus aureus* survival in 5-16% MSM and 12, 30 or 60 µg/ml oxacillin for 96 hours.

| % MSM | 12 µg/ml oxacillin MSM (cfu/ml) | 12 µg/ml oxacillin MSM (cfu/ml) | 12 µg/ml oxacillin MSM (cfu/ml) | 96 hours Average Log |
|---|---|---|---|---|
| 16 | $1.4 \times 10^2$ | $1.4 \times 10^2$ | $1.6 \times 10^2$ | 2.2 |
| 15 | $1.2 \times 10^2$ | $1.3 \times 10^2$ | $1.2 \times 10^2$ | 2.1 |
| 14 | $6.0 \times 10^1$ | $6.0 \times 10^1$ | $5.0 \times 10^1$ | 1.8 |
| 13 | $1.6 \times 10^3$ | $1.7 \times 10^3$ | $1.2 \times 10^3$ | 3.2 |
| 12 | $6.8 \times 10^3$ | $7.0 \times 10^3$ | $6.8 \times 10^3$ | 3.8 |
| 11 | $>3.3 \times 10^5$ | $>3.3 \times 10^5$ | $>3.3 \times 10^5$ | 5.5 |
| 10 | $>3.3 \times 10^5$ | $>3.3 \times 10^5$ | $>3.3 \times 10^5$ | 5.5 |
| 9 | $>3.3 \times 10^5$ | $>3.3 \times 10^5$ | $>3.3 \times 10^5$ | 5.5 |
| 8 | $>3.3 \times 10^5$ | $>3.3 \times 10^5$ | $>3.3 \times 10^5$ | 5.5 |
| 7 | $>3.3 \times 10^5$ | $>3.3 \times 10^5$ | $>3.3 \times 10^5$ | 5.5 |
| 6 | $>3.3 \times 10^5$ | $>3.3 \times 10^5$ | $>3.3 \times 10^5$ | 5.5 |

TABLE 8-continued

ATCC strain 43300 *Staphylococcus aureus* survival in 5-16% MSM and 12, 30 or 60 µg/ml oxacillin for 96 hours.

| 5 | >3.3 × 10$^5$ | >3.3 × 10$^5$ | >3.3 × 10$^5$ | 5.5 |
| 0 | >3.3 × 10$^5$ | >3.3 × 10$^5$ | >3.3 × 10$^5$ | 5.5 |

| % MSM | 30 µg/ml oxacillin MSM (cfu/ml) | 30 µg/ml oxacillin MSM (cfu/ml) | 30 µg/ml oxacillin MSM (cfu/ml) | 96 hours Average Log |
| --- | --- | --- | --- | --- |
| 16 | 3.0 × 10$^1$ | 3.0 × 10$^1$ | 1.0 × 10$^1$ | 1.3 |
| 15 | 8.0 × 10$^1$ | 8.0 × 10$^1$ | 8.0 × 10$^1$ | 1.9 |
| 14 | 5.0 × 10$^1$ | 5.0 × 10$^1$ | 6.0 × 10$^1$ | 1.7 |
| 13 | 3.3 × 10$^2$ | 3.1 × 10$^2$ | 3.2 × 10$^2$ | 2.5 |
| 12 | 6.9 × 10$^3$ | 3.9 × 10$^3$ | 3.9 × 10$^3$ | 3.7 |
| 11 | >3.3 × 10$^5$ | >3.3 × 10$^5$ | >3.3 × 10$^5$ | 5.5 |
| 10 | >3.3 × 10$^5$ | >3.3 × 10$^5$ | >3.3 × 10$^5$ | 5.5 |
| 9 | 1.0 × 10$^4$ | 1.02 × 10$^4$ | 1.01 × 10$^4$ | 4.0 |
| 8 | >3.3 × 10$^5$ | >3.3 × 10$^5$ | >3.3 × 10$^5$ | 5.5 |
| 7 | >3.3 × 10$^5$ | >3.3 × 10$^5$ | >3.3 × 10$^5$ | 5.5 |
| 6 | >3.3 × 10$^5$ | >3.3 × 10$^5$ | >3.3 × 10$^5$ | 5.5 |
| 5 | >3.3 × 10$^5$ | >3.3 × 10$^5$ | >3.3 × 10$^5$ | 5.5 |
| 0 | >3.3 × 10$^5$ | >3.3 × 10$^5$ | >3.3 × 10$^5$ | 5.5 |

| % MSM | 60 µg/ml oxacillin MSM (cfu/ml) | 60 µg/ml oxacillin MSM (cfu/ml) | 60 µg/ml oxacillin MSM (cfu/ml) | 96 hours Average Log |
| --- | --- | --- | --- | --- |
| 16 | 2.0 × 10$^1$ | 3.0 × 10$^1$ | 2.0 × 10$^1$ | 1.3 |
| 15 | 0 | 0 | 0 | |
| 14 | 0 | 0 | 0 | |
| 13 | 4.0 × 10$^1$ | 4.0 × 10$^1$ | 5.0 × 10$^1$ | 1.6 |
| 12 | 3.0 × 10$^3$ | 3.5 × 10$^3$ | 3.1 × 10$^3$ | 3.5 |
| 11 | 0 | 0 | 0 | |
| 10 | 3.9 × 10$^3$ | 4.0 × 10$^3$ | 3.5 × 10$^3$ | 3.6 |
| 9 | >3.3 × 10$^5$ | >3.3 × 10$^5$ | >3.3 × 10$^5$ | 5.5 |
| 8 | >3.3 × 10$^5$ | >3.3 × 10$^5$ | >3.3 × 10$^5$ | 5.5 |
| 7 | >3.3 × 10$^5$ | >3.3 × 10$^5$ | >3.3 × 10$^5$ | 5.5 |
| 6 | 4.4 × 10$^3$ | 4.5 × 10$^3$ | 4.4 × 10$^3$ | 3.6 |
| 5 | >3.3 × 10$^5$ | >3.3 × 10$^5$ | >3.3 × 10$^5$ | 5.5 |
| 0 | >3.3 × 10$^5$ | >3.3 × 10$^5$ | >3.3 × 10$^5$ | 5.5 |

As shown in Table 8, the 11% and 14% MSM with 60 µg/ml oxacillin conditions at 96 hours showed no sign of colonies. The tube was then taken out of the experiment and tested for ATCC strain 43300 *Staphylococcus* growth. The tube was spun down at 5000 rpm for 10 minutes. The supernatant was then decanted into 90 mls of Mueller-Hinton broth with 6 µg/ml oxacillin. This is for enrichment and the recovery of any MRSA cells that may be present whether healthy or stressed. The pellet had 10 mls Mueller-Hinton broth with 6 µg/ml oxacillin added to it to recover any cells that may be present. Both vessels were incubated at 35° C. for 48 hours followed by plating every 24 hours. Each vessel was plated at 10 dilutions to obtain a 1 cfu detection limit. No colonies were observed, indicating total kill. This time point for graphing purposes will be reported as 0 logs.

As shown in Table 8, the 12 µg/ml oxacillin with 12 and 13% MSM conditions exhibited increased colony counts compared to the earlier time points. The 12 µg/ml oxacillin with 14-16% conditions exhibited the same colony counts as the previous time point of 72 hours. The 30 µg/ml oxacillin condition showed an increased reversion to oxacillin resistance thru the lower MSM percentages of 5-13%. The log reduction in cfu/ml observed was slight for the 14-16% compared to the previous time point and appears to stay constant. The 60 µg/ml oxacillin showed no colonies at MSM concentrations of 11 and 14%. At 60 µg/ml oxacillin with MSM concentrations of 5-10% and 12% observed cfu/ml was greater than the detection limit. The data at 11-12% may possibly be showing that the amount of MSM addition is crucial for full reduction of the organism since the higher amounts (14 & 15%) show signs of reduction to total kill.

TABLE 9

ATCC strain 43300 *Staphylococcus aureus* survival in 5-16% MSM and 12, 30 or 60 µg/ml oxacillin for 120 hours.

| % MSM | 12 µg/ml oxacillin MSM (cfu/ml) | 12 µg/ml oxacillin MSM (cfu/ml) | 12 µg/ml oxacillin MSM (cfu/ml) | 120 hours Average Log |
| --- | --- | --- | --- | --- |
| 16 | 3.0 × 10$^1$ | 3.0 × 10$^1$ | 2.0 × 10$^1$ | 1.5 |
| 15 | 1.1 × 10$^2$ | 1.3 × 10$^2$ | 1.2 × 10$^2$ | 2.0 |
| 14 | 1.1 × 10$^2$ | 1.2 × 10$^2$ | 1.1 × 10$^2$ | 2.0 |
| 13 | 6.2 × 10$^3$ | 6.7 × 10$^3$ | 6.2 × 10$^3$ | 3.8 |
| 12 | >3.3 × 10$^5$ | >3.3 × 10$^5$ | >3.3 × 10$^5$ | 5.5 |
| 11 | >3.3 × 10$^5$ | >3.3 × 10$^5$ | >3.3 × 10$^5$ | 5.5 |
| 10 | >3.3 × 10$^5$ | >3.3 × 10$^5$ | >3.3 × 10$^5$ | 5.5 |
| 9 | >3.3 × 10$^5$ | >3.3 × 10$^5$ | >3.3 × 10$^5$ | 5.5 |
| 8 | >3.3 × 10$^5$ | >3.3 × 10$^5$ | >3.3 × 10$^5$ | 5.5 |
| 7 | >3.3 × 10$^5$ | >3.3 × 10$^5$ | >3.3 × 10$^5$ | 5.5 |
| 6 | >3.3 × 10$^5$ | >3.3 × 10$^5$ | >3.3 × 10$^5$ | 5.5 |
| 5 | >3.3 × 10$^5$ | >3.3 × 10$^5$ | >3.3 × 10$^5$ | 5.5 |
| 0 | >3.3 × 10$^5$ | >3.3 × 10$^5$ | >3.3 × 10$^5$ | 5.5 |

| % MSM | 30 µg/ml oxacillin MSM (cfu/ml) | 30 µg/ml oxacillin MSM (cfu/ml) | 30 µg/ml oxacillin MSM (cfu/ml) | 120 hours Average Log |
| --- | --- | --- | --- | --- |
| 16 | 2.0 × 10$^1$ | 3.0 × 10$^1$ | 2.0 × 10$^1$ | 1.3 |
| 15 | 0 | 0 | 0 | 0 |
| 14 | 3.0 × 10$^1$ | 2.0 × 10$^1$ | 2.0 × 10$^1$ | 1.3 |
| 13 | 1.02 × 10$^3$ | 1.01 × 10$^3$ | 1.02 × 10$^3$ | 3.0 |
| 12 | 6.8 × 10$^4$ | 3.9 × 10$^4$ | 6.9 × 10$^4$ | 4.7 |
| 11 | >3.3 × 10$^5$ | >3.3 × 10$^5$ | >3.3 × 10$^5$ | 5.5 |
| 10 | >3.3 × 10$^5$ | >3.3 × 10$^5$ | >3.3 × 10$^5$ | 5.5 |
| 9 | >3.3 × 10$^5$ | >3.3 × 10$^5$ | >3.3 × 10$^5$ | 5.5 |
| 8 | >3.3 × 10$^5$ | >3.3 × 10$^5$ | >3.3 × 10$^5$ | 5.5 |
| 7 | >3.3 × 10$^5$ | >3.3 × 10$^5$ | >3.3 × 10$^5$ | 5.5 |
| 6 | >3.3 × 10$^5$ | >3.3 × 10$^5$ | >3.3 × 10$^5$ | 5.5 |
| 5 | >3.3 × 10$^5$ | >3.3 × 10$^5$ | >3.3 × 10$^5$ | 5.5 |
| 0 | >3.3 × 10$^5$ | >3.3 × 10$^5$ | >3.3 × 10$^5$ | 5.5 |

| % MSM | 60 µg/ml oxacillin MSM (cfu/ml) | 60 µg/ml oxacillin MSM (cfu/ml) | 60 µg/ml oxacillin MSM (cfu/ml) | 120 hours Average Log |
| --- | --- | --- | --- | --- |
| 16 | 0 | 0 | 0 | 0 |
| 15 | 0 | 0 | 0 | 0 |
| 14 | 0 | 0 | 0 | 0 |
| 13 | 0 | 0 | 0 | 0 |
| 12 | 1.72 × 10$^4$ | 1.6 × 10$^4$ | 1.5 × 10$^4$ | 4.2 |
| 11 | 0 | 0 | 0 | 0 |
| 10 | 1.6 × 10$^4$ | 1.5 × 10$^4$ | 1.7 × 10$^4$ | 4.2 |
| 9 | >3.3 × 10$^5$ | >3.3 × 10$^5$ | >3.3 × 10$^5$ | 5.5 |
| 8 | >3.3 × 10$^5$ | >3.3 × 10$^5$ | >3.3 × 10$^5$ | 5.5 |
| 7 | >3.3 × 10$^5$ | >3.3 × 10$^5$ | >3.3 × 10$^5$ | 5.5 |
| 6 | 3.7 × 10$^4$ | 3.4 × 10$^4$ | 2.4 × 10$^4$ | 4.5 |
| 5 | >3.3 × 10$^5$ | >3.3 × 10$^5$ | >3.3 × 10$^5$ | 5.5 |
| 0 | >3.3 × 10$^5$ | >3.3 × 10$^5$ | >3.3 × 10$^5$ | 5.5 |

As shown in Table 9, the 15% MSM with 30 µg/ml oxacillin condition, and the 13 and 16% MSM with 60 µg/ml oxacillin condition, at 120 hours showed no sign of colonies. The tube was then taken out of the experiment and tested for ATCC strain 43300 *Staphylococcus aureus* growth. The tube was spun down at 5000 rpm for 10 minutes. The supernatant was then decanted into 90 mls of Mueller-Hinton broth with 6 µg/ml oxacillin. This is for enrichment and the recovery of any ATCC strain 43300 *Staphylococcus aureus* cells that may be present whether healthy or stressed. The pellet had 10 mls Mueller-Hinton broth (Mueller & Hinton, *Proc. Soc. Exp. Diol. and Med.;* 48:330-333, 1941); with 6 µg/ml oxacillin added to it to recover any cells that may be present. Both vessels were incubated at 35° C. for 48 hours followed by plating every 24 hours. Each vessel was plated at 10 dilutions to obtain a 1 cfu detection limit. No colonies were observed, indicating total kill. This time point for graphing purposes will be reported as 0 logs.

The 12 µg/ml concentrations show that there is slight reduction or increase at 14-16% MSM. At 30 µg/ml the 15% MSM concentration point has a true kill with no recovery noticed. The 14% and 16% concentration points had no change of significant value from the previous time point. The 13% and 16% MSM concentration points of 60 µg/ml had true kill with no recovery of organism. The 12% concentration point shows a continued increase in log from the previous time point.

Overall, the data presented in Tables 5-9 shows that at the first 24 hours there was a significant reduction in log for the lower (5-10%) concentrations at each of the three oxacillin levels (trend lines of 16-5% MSM concentration have a negative slope). The next time point of 48 hours shows that the reduction rates are beginning to shift from the lower end 5-10% to the higher end 11-16% (trend lines of 16-5% MSM concentration have a positive slope). The 72 hour mark shows a log reduction in cfu/ml at the higher MSM concentrations with the lower MSM concentrations showing little to no reduction in cfu/ml. The 96 and 120 hour time points show reduced bacteria survival at the highest MSM concentrations, but no effect on bacterial survival at lower MSM concentrations.

The results of this experiment raise some intriguing questions. The data at 24 hours show higher reduction at the lower percentages of MSM for all three concentrations of oxacillin evaluated. This trend is slightly changing at 48 hours with maximum reduction being observed in the mid to upper MSM concentrations. By 72 hours the trend has definitely switched to higher log reduction at the higher MSM concentrations. MSM was only added when additional growth media (LB containing the same original MSM concentration as the growth vial) was added to maintain original volume in the vial. For instance if a 1 ml aliquot of the 12 µg/ml oxacillin 5% MSM was removed for plating then 1 ml of LB containing 5% MSM would be added back.

The following are offered as hypothetical explanations for some of the effects seen above; however, these explanations are not intended to be limiting. One hypothetical and non-limiting possibility for the observed results is that MSM is being consumed by the organisms. Another hypothetical and non-limiting possibility for the observed results is that the ability of MSM to cause the reversion to sensitivity could be due to an ability of MSM to carry the oxacillin into the MRSA cells. Another hypothetical and non-limiting possibility for the observed results is that too high of a level of MSM is less effective at certain time points. For instance, this may be due to competition of an overabundance of free MSM molecules competing with MSM that has bind with the oxacillin at the higher concentrations. This would have more free MSM entering the cells than the oxacillin bound MSM. The lower concentrations have a higher overall percentage of the total MSM molecules in solution are bound to the oxacillin, allowing more of the bound oxacillin to enter the cell since there was less free MSM to compete. Under this hypothesis, for a given number of MSM molecules that will enter the MRSA cell the ratio of MSM to oxacillin is important to obtain the maximum effect. If an overabundance of MSM is present then the chance of MSM molecules not bound to the oxacillin penetrating the cell increases.

Example 8

Treatment of a Drug Resistant Bacterial Pathogen in a Subject

This example describes a representative method of treating a subject with a drug resistant bacterial infection (e.g., MRSA infection) by selecting a subject with a drug resistant bacterial infection and administering to the subject a therapeutically effective amount of MSM and an agent that inhibits the drug-sensitive form of the bacterial pathogen causing the drug resistant bacterial infection. In this example, the subject has a MRSA infection on its skin, and the treatment comprises topical administration of a composition comprising 12% MSM and 30 µg/ml oxacillin.

First, a subject having a MRSA infection is selected. The subject is selected by obtaining a biological sample from the subject and testing the biological sample for the presence of *Staphylococcus aureus* bacteria followed by detecting the MIC of the bacteria for oxacillin. If the MIC of oxacillin for the *staphylococcus aureus* bacteria in the biological sample from the subject is greater than 2 µg/ml, then the bacteria is a MRSA strain of bacteria. The sample contains *Staphylococcus aureus* bacteria and the detected MIC of oxacillin for the bacterial is more than 2 µg/ml for oxacillin using the Etest® system (AB bioMérieux, SA France). Therefore, the subject is selected.

Following selection of the subject with MRSA, a composition comprising 12% MSM and 30 µg/ml oxacillin is topically administered to the subject's skin in the area around the MRSA infection. The composition is water-based, formulated for topical administration and comprises 1% NaCl. The composition is administered twice a day, for 10 days. Following this course of treatment, the subject's symptoms of MRSA infection are observed to have decreased by at least 50% from the symptoms of MRSA infection present prior to treatment with MSM and oxacillin, indicating that the subject has been treated.

Example 9

Absorption of MSM in Topical Formulation is within Recognized Safe Levels

This example shows absorption of MSM in topical formulations is within recognized safe levels.

New Zealand White rabbits, which are an accepted animal model for dermal absorption studies, were used to assess the absorption and resultant blood levels of MSM. Rabbits were obtained from Charles River Canada (Saint-Constant, Quebec). Five male rabbits, ages 12-13 weeks and ranging in weight from 2.6 kg to 2.7 kg were used for the dermal absorption studies. Rabbits were used because of their greater skin permeability as compared to rats, pigs or humans. Thus, testing on rabbits is a more conservative approach for the safety of topical products for human use. The size of rabbit was based on the ethical restriction of collecting greater than 6 ml/kg body weight of blood within a two week period. The total volume of blood to be removed during this study was 10 ml on a single day. One animal per group was used to minimize the number of animals required. Animals were housed individually in stainless steel cages with 12 hours light/dark cycles. The animal room environment was monitored daily (targeted ranges: 18-26° C. and relative humidity 25-50%). Fresh air was supplied to the room at a sufficient rate to provide approximately 15 to 17 changes of room air per hour. Clinical observations were conducted for all animals to ensure animals were in good health prior to dosing. Morbidity and mortality observations were also conducted during the study period.

Treatment groups were as shown in Table 10:

TABLE 10

Study Design

| Group | Test Article | Surface Area Exposed | Volume Applied | Number of Animals | Blood Collection Times (min) |
|---|---|---|---|---|---|
| A | 10% MSM + 90% Water | 6 cm² | 0.5 ml | 1 | 0 (pre-dose), 10, 30, 120, 480 minutes |
| B | 50% DMSO + 50% Water | 6 cm² | 0.5 ml | 1 | 0 (pre-dose), 10, 30, 120, 480 minutes |
| C | 70% DMSO + 30% Water | 6 cm² | 0.5 ml | 1 | 0 (pre-dose), 10, 30, 120, 480 minute |
| D | 10% MSM + 50% DMSO + 40% Water | 6 cm² | 0.5 ml | 1 | 0 (pre-dose), 10, 30, 120, 480 minutes |
| E | 10% MSM + 70% DMSO + 20% Water | 6 cm² | 0.5 ml | 1 | 0 (pre-dose), 10, 30, 120, 480 minutes |

One day prior to the study, the rump of each rabbit was closely clipped using hair clippers. An area of 6 cm² was measured and marked to ensure equivalence in the application of the various compositions. Each product was applied by pipetting 0.5 ml of each composition into the center of the test area and spread to cover the entire test area. After the 5 minute exposure period, the compositions were removed by wiping, rinsing and drying the test area.

Prior to blood collection, animals were tranquilized with Acepromazine (1 mg/kg) by intramuscular injection in the right hind leg muscle, after which EMLA cream (lidocaine/prilocalne) was applied to both ears along the ear artery. Blood was collected by insertion of a 21 G needle (hub removed) into the ear artery. Approximately 2 ml of whole blood was collected into 4 ml vacuutainer tubes (Becton Dickinson, Mississauga, ON) containing $K_2EDTA$. Tubes were inverted to mix with the anticoagulant and stored refrigerated until plasma was separated by centrifugation. Plasma was separated from whole blood by centrifugation at 3000×g for 10 minutes. Plasma was collected, transferred and stored in a cryovial at −70° C. until further processing for MSM analysis.

Following the 5 minute exposure period to the various test products (see Table 1), blood was collected after 10 minutes, 30 minutes, 2 hours and 8 hours. Prior to the 2 and 8 hour blood collections, EMLA cream was applied to the ears (approximately 30 minutes prior to each of these blood draws) as the anesthetic effects of the EMLA cream lasts approximately 1 to 2 hours. Both EMLA cream and Acepromazine were used due to ethical considerations and to provide for the wellbeing of the animals used in this study.

The concentrations of MSM in plasma were quantified by gas chromatography-mass spectrometry (GC/MS) based on established methods. Briefly, 450 µl of plasma sample was mixed with 50 µl of physiological saline and vortexed for 30 seconds. Following this 1 ml of Acetonitrile (Fisher, HPLC grade) was added to the mixture. The solution was vortexed vigorously for 60 seconds and centrifuged at 2000 rpm for 5 minutes. One microliter of the clear supernatant was introduced to the GC/MS system (GC/MS QP20108 EI, Shimadzu, Kyoto, Japan). The analysis was performed on a 8himadzu SHR5XLB column (0.25 mm ID×length 30 m, film 0.25 um, Kyoto, Japan). The retention time of MSM was 6.1-6.3 minutes. MSM was detected with MS and m/z 79 (M+−15) was used for monitoring MSM ion SIM profiles. Helium gas was used as the carrier gas, head pressure was 0.25 kg/cm2, make-up gas was 30 ml/min, column temperature was 80° C., injector temperature 120° C., separator temperature 200° C. and ion source temperature 250° C. The ionization energy was 70 eV. An external standard graph was prepared with MSM dissolved in acetonitrile at the following concentrations: 62.5 µg/ml, 31.3 µg/ml, 15.6 µg/ml, 7.8 µg/ml, 3.9 µg/ml, 1.9 µg/ml, 0.98 µg/ml and 0.49 µg/ml. The MSM concentration in plasma samples was calculated from the slope of the standard curve. The best fitted graph was linear with a R2 value of 0.998.

All animals were observed prior to the start of the study and all demonstrated good health. During the course of the study and subsequent to the study, all animals demonstrated good health. Morbidity, mortality and injury were assessed twice daily. No animals demonstrated any morbidity, mortality or injury.

TABLE 11

Concentration of MSM in Plasma After Exposure to MSM and DMSO

| Treatment | Time point (minute) | MSM Concentration (µg/ml) |
|---|---|---|
| 10% MSM + 90% water | 0 | 25.6 |
| | 10 | 17.6 |
| | 30 | 16.3 |
| | 120 | 14.0 |
| | 480 | 15.4 |
| 50% DMSO + 50% water | 0 | 4.2 |
| | 10 | 6.9 |
| | 30 | 6.9 |
| | 120 | 7.4 |
| | 480 | 12.6 |
| 70% DMSO + 30% water | 0 | 56.7 |
| | 10 | 89.0 |
| | 30 | 98.9 |
| | 120 | 128.7 |
| | 480 | 120.2 |
| 10% MSM + 50% DMSO + 40% water | 0 | 104.2 |
| | 10 | 116.5 |
| | 30 | 127.9 |
| | 120 | 128.4 |
| | 480 | 140.4 |
| 10% MSM + 70% DMSO + 20% water | 0 | 26.8 |
| | 10 | 37.3 |
| | 30 | 30.9 |
| | 120 | 33.9 |
| | 480 | 44.4 |

The results of the absorption study are summarized in Table 11. Baseline plasma concentrations of MSM (prior to exposure to test articles) ranged between 4.2 µg/ml and 104.2 µg/ml. The variation in baseline is within the normal range of variation of natural MSM concentrations that have been established in prior studies. Following exposure to the various test articles, the highest plasma concentrations of MSM measured were less than or equal to approximately 140 µg/ml. This peak concentration results from exposure to 10% MSM+ 70% DMSO+20% water. When corrected for natural variation in baseline MSM concentrations, the largest change in plasma MSM was detected in the 70% DMSO+30% water group. These data suggest that variations in MSM, either due to absorption or due to metabolism of DMSO, are within the natural range of MSM concentrations.

Example 10

Effect of MSM on Sensitivity of MRSA to 12, 30, or 60 µg/ml Methicillin

This example describes in vitro experiments testing the survival of ATCC strain 43300 *Staphylococcus aureus* in the presence of 5-16% MSM and an initial concentration of 12, 30 or 60 µg/ml methicillin. These correspond to 2×, 5× and 10×MIC for methicillin. Additional antibiotic was added every 24 hours. The growth periods tested were 24 (FIG. 5), 48, 72, 96 and 120 hours. The results show that MSM sensitized a MRSA strain to methicillin Methods:

USP<51> Antimicrobial Effectiveness protocol was used as the template experimental paradigm. Initial MSM concentrations tested were 5-16% in increments of one. All concentrations were plated out to the $10^{-7}$ dilutions to ascertain cfu/ml. The initial concentration of methicillin used was 12, 30 or 60 µg/ml, which corresponds to 2×, 5× and 10×MIC for methicillin. Additional antibiotic was added at the initial concentration every 24 hours.

Materials used were Flake OptiMSM® MSM (lot number 0604751), ATCC strain 43300 *Staphylococcus aureus*, 30 ml Borosilicate glass cultures tubes, Lactose Broth (LB; Alpha Biosciences; Lot: L07-03), Modified Letheen Broth (MLB, Alpha Biosciences, lot I08-09), Trypto Soy Agar with Lecithin and Tween 80 (TSA; Alpha Biosciences, lot: F08-42) and methicillin sodium USP grade lot KOH338.

ATCC strain 43300 *Staphylococcus aureus* was streaked out for isolations. An isolated colony was chosen, streaked again and incubated. Isolate was chosen and then diluted to a McFarland standard of one. The estimated value was then taken to inoculate tubes containing growth media and 12, 30 or 60 µg/ml methicillin with approximately $10^5$ cfu/ml. These tubes were incubated and plated for counting cfu. A clone having no observed log reduction in cfu was selected for the rest of the experiment.

Flake OptiMSM® MSM was weighed out on a certified Mettler Toledo AG245 SN: 1115210833 and aliquoted for each concentration. The MSM was placed into 30 ml borosilicate glass culture tubes. MSM was added to tubes as follows: 5% (0.5 g), 6% (0.6 g), 7% (0.7 g), 8% (0.8 g), 9% (0.9 g), 10% (1.0 g), 11% (1.1 g), 12% (1.2 g), 13% (1.3 g), 14% (1.4 g), 15% (1.5 g), and 16% (1.6 g). Material was calculated on a 10 ml volume. Sterile methicillin was added to each experimental condition to a final concentration of 12, 30 or 60 µg/ml antibiotic. Lactose Broth positive controls both with and without the 12 µg/ml, 30 µg/ml, 60 µg/ml antibiotic were inoculated with MRSA. The Lactose Broth also had a set of negative controls. MSM controls (no antibiotic) at 5%, 10%, and 16% concentrations were also run both with and without MRSA. Tubes were set up in singlet, but plated in triplicate, as described below.

All tubes were then inoculated with a dilution of the selected ATCC strain 43300 *Staphylococcus aureus* clone giving a final level of colony forming units of $1.49 \times 10^5$/ml (log=5.17). The tubes were incubated at 25° C. and mixed periodically. Antibiotic was re-inoculated every 24 hours at the initial concentration to maintain pressure on the organism. Plating was done at 24, 48, 72, and 120 hours. Each condition was plated by diluting 1 ml of growth material into 9 ml of MLB diluent broth. Each time this was done, 1 ml of MSM-containing growth media was added back to the tube to maintain a constant volume and MSM concentration. This mixture was serial diluted down to $10^{-7}$ with 1 ml placed in triplicate in a sterile petri dish at each dilution point. 20 mls of TSA was added to each dilution, swirled and allowed to solidify. All dilutions were placed in a 35° C. incubator for 24 to 72 hours. Bacterial colonies on each plate were counted and the average taken then changed into log format. Any cfu/ml observed greater than $1.49 \times 10^5$/ml (log=5.17) were recorded TNTC. Graphs were recorded as log of 5.2 for TNTC to show comparison among the other data points.

Results:

Positive controls (those inoculated with MRSA) for the three concentrations of methicillin alone used in this experiment (12 µg/ml, 30 µg/ml and 60 µg/ml) showed no significant decrease in colony forming units from the initial inoculums value. The results of this study are shown in Tables 12-16.

TABLE 12

ATCC strain 43300*Staphylococcus aureus* survival in 5-16% MSM and 12, 30 or 60 µg/ml methicillin for 24 hours.

| % MSM Concentration | 12 µg/ml methicillin/ MSM (cfu/ml) | 12 µg/ml methicillin/ MSM (cfu/ml) | 12 µg/ml methicillin/ MSM (cfu/ml) | 24 hours Average Log |
|---|---|---|---|---|
| 16 | $1.01 \times 10^3$ | $1.03 \times 10^3$ | $1.04 \times 10^3$ | 3.0 |
| 15 | $6.4 \times 10^3$ | $6.6 \times 10^3$ | $6.5 \times 10^3$ | 3.8 |
| 14 | $8.8 \times 10^3$ | $8.5 \times 10^3$ | $8.2 \times 10^3$ | 3.9 |
| 13 | $3.3 \times 10^3$ | $3.5 \times 10^3$ | $3.4 \times 10^3$ | 3.5 |
| 12 | $2.9 \times 10^3$ | $3.0 \times 10^3$ | $2.8 \times 10^3$ | 3.5 |
| 11 | $2.2 \times 10^3$ | $2.3 \times 10^3$ | $2.3 \times 10^3$ | 3.3 |
| 10 | $1.4 \times 10^3$ | $1.4 \times 10^3$ | $1.4 \times 10^3$ | 3.1 |
| 9 | $9.0 \times 10^2$ | $9.4 \times 10^2$ | $9.2 \times 10^2$ | 3.0 |
| 8 | $9.6 \times 10^2$ | $9.5 \times 10^2$ | $9.3 \times 10^2$ | 3.0 |
| 7 | $4.4 \times 10^2$ | $4.4 \times 10^2$ | $5.0 \times 10^2$ | 2.7 |
| 6 | $4.0 \times 10^2$ | $4.4 \times 10^2$ | $4.5 \times 10^2$ | 2.6 |
| 5 | $7.8 \times 10^2$ | $8.0 \times 10^2$ | $8.2 \times 10^2$ | 2.9 |
| 0 | TNTC | TNTC | TNTC | |

| % MSM Concentration | 30 µg/ml methicillin/ MSM (cfu/ml) | 30 µg/ml methicillin/ MSM (cfu/ml) | 30 µg/ml methicillin/ MSM (cfu/ml) | 24 hours Average Log |
|---|---|---|---|---|
| 16 | $9.6 \times 10^3$ | $9.8 \times 10^3$ | $9.7 \times 10^3$ | 4.0 |
| 15 | $7.8 \times 10^3$ | $7.6 \times 10^3$ | $8.0 \times 10^3$ | 3.9 |
| 14 | $6.3 \times 10^3$ | $6.7 \times 10^3$ | $6.9 \times 10^3$ | 3.8 |
| 13 | $6.5 \times 10^3$ | $6.5 \times 10^3$ | $6.4 \times 10^3$ | 3.8 |
| 12 | $3.3 \times 10^3$ | $3.3 \times 10^3$ | $3.3 \times 10^3$ | 3.5 |
| 11 | $3.3 \times 10^3$ | $2.8 \times 10^3$ | $3.1 \times 10^3$ | 3.5 |
| 10 | $1.2 \times 10^3$ | $1.3 \times 10^3$ | $1.1 \times 10^3$ | 3.1 |
| 9 | $1.1 \times 10^3$ | $1.3 \times 10^3$ | $1.2 \times 10^3$ | 3.1 |
| 8 | $9.4 \times 10^2$ | $9.6 \times 10^2$ | $9.6 \times 10^2$ | 3.0 |
| 7 | $3.4 \times 10^2$ | $3.5 \times 10^2$ | $3.3 \times 10^2$ | 2.5 |
| 6 | $2.2 \times 10^2$ | $2.2 \times 10^2$ | $2.5 \times 10^2$ | 2.4 |
| 5 | $3.8 \times 10^2$ | $4.1 \times 10^2$ | $4.0 \times 10^2$ | 2.6 |
| 0 | TNTC | TNTC | TNTC | |

| % MSM Concentration | 60 µg/ml methicillin/ MSM (cfu/ml) | 60 µg/ml methicillin/ MSM (cfu/ml) | 60 µg/ml methicillin/ MSM (cfu/ml) | 24 hours Average Log |
|---|---|---|---|---|
| 16 | $8.4 \times 10^3$ | $8.4 \times 10^3$ | $8.5 \times 10^3$ | 3.9 |
| 15 | $8.3 \times 10^3$ | $8.5 \times 10^3$ | $8.4 \times 10^3$ | 3.9 |
| 14 | $8.3 \times 10^3$ | $8.8 \times 10^3$ | $8.5 \times 10^3$ | 3.9 |
| 13 | $7.0 \times 10^3$ | $6.8 \times 10^3$ | $6.5 \times 10^3$ | 3.8 |
| 12 | $4.5 \times 10^3$ | $4.1 \times 10^3$ | $4.7 \times 10^3$ | 3.6 |
| 11 | $3.5 \times 10^3$ | $3.8 \times 10^3$ | $3.9 \times 10^3$ | 3.6 |
| 10 | $2.2 \times 10^3$ | $2.1 \times 10^3$ | $2.0 \times 10^3$ | 3.3 |
| 9 | $2.0 \times 10^3$ | $1.6 \times 10^3$ | $1.8 \times 10^3$ | 3.2 |
| 8 | $9.4 \times 10^2$ | $9.8 \times 10^2$ | $9.7 \times 10^2$ | 3.0 |
| 7 | $6.1 \times 10^2$ | $6.3 \times 10^2$ | $6.2 \times 10^2$ | 2.8 |
| 6 | $4.2 \times 10^2$ | $4.2 \times 10^2$ | $4.8 \times 10^2$ | 2.6 |
| 5 | $8.3 \times 10^2$ | $8.1 \times 10^2$ | $8.1 \times 10^2$ | 2.9 |
| 0 | TNTC | TNTC | TNTC | |

Figure 5:
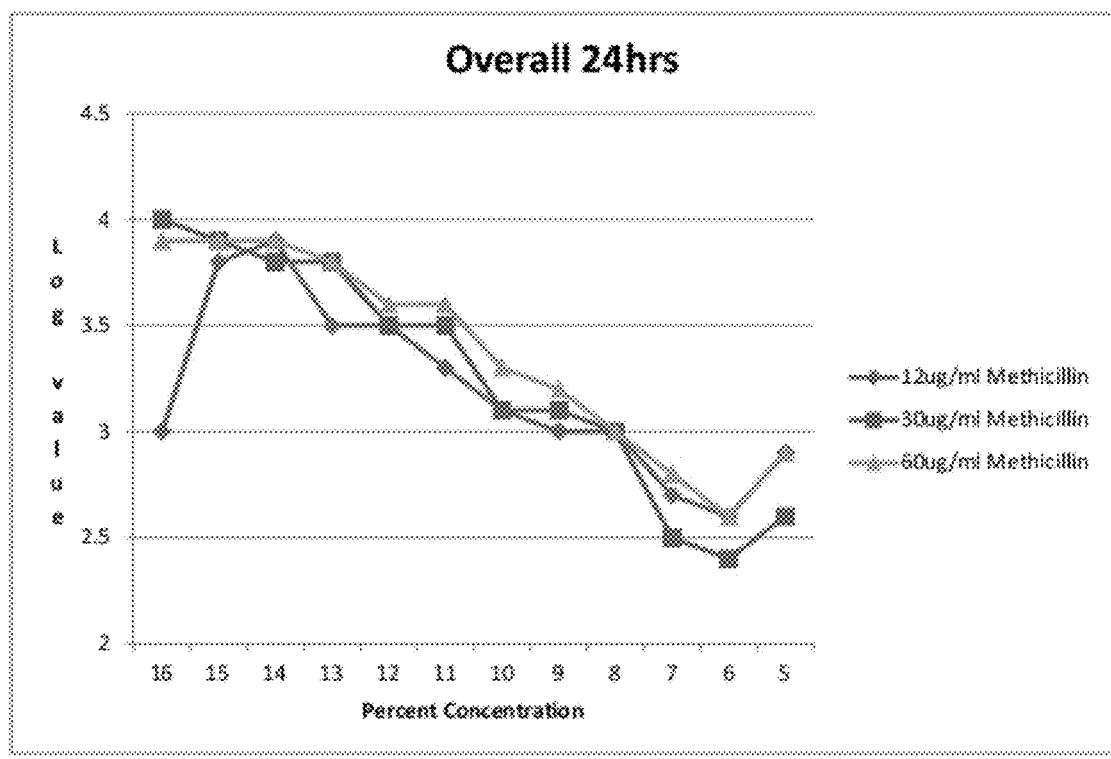
FIG. 5 is a graph illustrating that MSM sensitizes MRSA to multiple concentrations of methicillin. In vitro survival of ATCC strain 43300 *staphylococcus aureus* (a MRSA strain resistant to oxacillin and methicillin), was tested in the presence of MSM and methicillin. Three different concentrations of methicillin were tested, corresponding to 2×, 5× and 10×MIC for this strain of MRSA for each antibiotic. ATCC strain 43300 *staphylococcus aureus* was incubated with 5-16% MSM and the indicated amount of antibiotic for 24 hours at 25° C. Thus, the bacteria were under 2×, 5×, or 10×MIC concentrations of methicillin for 24 hours. The initial inoculation of bacteria was $1.49 \times 10^5$/ml (log=5.17). At this time point, lower concentrations of MSM with antibiotic had a greater effect on bacterial survival than higher concentrations of MSM. Overall, these results confirm that MSM sensitizes MRSA to methicillin.

As shown in Table 12 and FIG. 5, the number of cfu/ml observed at the 24 hour time point is similar between all concentrations. The lower end of the MSM concentrations tends to have a higher log reduction in colony count then the higher MSM concentrations. The average log reduction in colony count for 12 μg/ml methicillin is 1.5 logs which carried throughout all the MSM concentrations with little or no change. The 30 μg/ml methicillin conditions had a significant reduction on the lower end of MSM concentrations being an average of a 3 log difference. The 60 μg/ml methicillin condition showed a slightly lower log reduction in colony count during the first 24 hour period of the three concentrations of antibiotic. One point of interest is the 12 μg/ml at 16% MSM had a 2.2 log reduction, which is the most observed at the higher concentrations. One hypothetical possibility is that this is an outlier or an optimal point for the antibiotic uptake for this concentration. The 30 μg/ml had the highest overall log reduction of 2.8 in colony count at the 6% concentration. Negative LB controls showed no signs of contamination. LB positive controls showed turbid growth and were terminated at this point for safety reasons. The negative 5%, 10%, and 16% MSM controls had no signs of contamination. The positive 5%, 10%, and 16% MSM controls had signs of turbid growth, was TNTC for all dilutions plated and were terminated at this time point for safety reasons. The antibiotic controls showed no signs of significant reduction from the initial inoculums, and the negative controls showed no signs of contamination.

TABLE 13

ATCC strain 43300 *Staphylococcus aureus* survival in 5-16% MSM and 12, 30 or 60 μg/ml methicillin for 48 hours.

| % MSM Concentration | 12 pg/ml methicillin/ MSM (cfu/ml) | 12 pg/ml methicillin/ MSM (cfu/ml) | 12 μg/ml methicillin/ MSM (cfu/ml) | 48 hours Average Log |
|---|---|---|---|---|
| 16 | $8.1 \times 10^2$ | $8.3 \times 10^2$ | $8.4 \times 10^2$ | 2.9 |
| 15 | $5.1 \times 10^2$ | $5.3 \times 10^2$ | $5.6 \times 10^2$ | 2.7 |
| 14 | $5.1 \times 10^2$ | $5.4 \times 10^2$ | $5.2 \times 10^2$ | 2.7 |
| 13 | $3.6 \times 10^2$ | $3.3 \times 10^2$ | $3.4 \times 10^2$ | 2.5 |
| 12 | $6.3 \times 10^2$ | $6.4 \times 10^2$ | $6.2 \times 10^2$ | 2.8 |
| 11 | $5.9 \times 10^2$ | $5.7 \times 10^2$ | $6.0 \times 10^2$ | 2.8 |
| 10 | $4.1 \times 10^2$ | $4.6 \times 10^2$ | $4.7 \times 10^2$ | 2.6 |
| 9 | $2.5 \times 10^2$ | $2.8 \times 10^2$ | $3.2 \times 10^2$ | 2.4 |
| 8 | $1.0 \times 10^2$ | $1.0 \times 10^2$ | $1.1 \times 10^2$ | 2.0 |
| 7 | $4.0 \times 10^1$ | $3.0 \times 10^1$ | $4.0 \times 10^1$ | 1.6 |
| 6 | $1.0 \times 10^1$ | $1.0 \times 10^1$ | $2.0 \times 10^1$ | 1.1 |
| 5 | $2.0 \times 10^2$ | $1.8 \times 10^2$ | $2.1 \times 10^2$ | 2.3 |
| 0 | TNTC | TNTC | TNTC | |

| % MSM Concentration | 30 pg/ml methicillin/ MSM (cfu/ml) | 30 pg/ml methicillin/ MSM (cfu/ml) | 30 μg/ml methicillin/ MSM (cfu/ml) | 48 hours Average Log |
|---|---|---|---|---|
| 16 | $4.5 \times 10^2$ | $4.7 \times 10^2$ | $4.6 \times 10^2$ | 2.7 |
| 15 | $5.3 \times 10^2$ | $5.2 \times 10^2$ | $5.6 \times 10^2$ | 2.7 |
| 14 | $7.0 \times 10^2$ | $6.8 \times 10^2$ | $7.4 \times 10^2$ | 2.8 |
| 13 | $4.0 \times 10^2$ | $4.0 \times 10^2$ | $4.0 \times 10^2$ | 2.6 |
| 12 | $4.8 \times 10^2$ | $5.0 \times 10^2$ | $5.1 \times 10^2$ | 2.7 |
| 11 | $1.9 \times 10^2$ | $1.8 \times 10^2$ | $2.1 \times 10^2$ | 2.3 |
| 10 | $1.2 \times 10^2$ | $1.8 \times 10^2$ | $1.6 \times 10^2$ | 2.2 |
| 9 | $2.1 \times 10^2$ | $2.3 \times 10^2$ | $2.4 \times 10^2$ | 2.3 |
| 8 | $4.1 \times 10^2$ | $4.0 \times 10^2$ | $3.4 \times 10^2$ | 2.6 |
| 7 | $1.8 \times 10^2$ | $1.5 \times 10^2$ | $1.6 \times 10^2$ | 2.2 |
| 6 | $2.9 \times 10^2$ | $2.2 \times 10^2$ | $2.5 \times 10^2$ | 2.4 |
| 5 | $4.6 \times 10^2$ | $4.8 \times 10^2$ | $4.4 \times 10^2$ | 2.7 |
| 0 | TNTC | TNTC | TNTC | |

TABLE 13-continued

ATCC strain 43300 *Staphylococcus aureus* survival in 5-16% MSM and 12, 30 or 60 μg/ml methicillin for 48 hours.

| % MSM Concentration | 60 pg/ml methicillin/ MSM (cfu/ml) | 60 pg/ml methicillin/ MSM (cfu/ml) | 60 μg/ml methicillin/ MSM (cfu/ml) | 48 hours Average Log |
|---|---|---|---|---|
| 16 | $2.1 \times 10^2$ | $2.2 \times 10^2$ | $1.8 \times 10^2$ | 2.3 |
| 15 | $3.5 \times 10^2$ | $3.8 \times 10^2$ | $3.8 \times 10^2$ | 2.6 |
| 14 | $2.9 \times 10^2$ | $2.9 \times 10^2$ | $3.1 \times 10^2$ | 2.5 |
| 13 | $4.0 \times 10^2$ | $3.7 \times 10^2$ | $3.6 \times 10^2$ | 2.6 |
| 12 | $3.3 \times 10^2$ | $3.8 \times 10^2$ | $3.7 \times 10^2$ | 2.6 |
| 11 | $5.0 \times 10^1$ | $5.0 \times 10^1$ | $4.0 \times 10^1$ | 1.7 |
| 10 | $2.1 \times 10^2$ | $2.4 \times 10^2$ | $2.5 \times 10^2$ | 2.4 |
| 9 | $1.3 \times 10^2$ | $1.2 \times 10^2$ | $1.3 \times 10^2$ | 2.1 |
| 8 | $8.0 \times 10^1$ | $6.0 \times 10^1$ | $7.0 \times 10^1$ | 1.8 |
| 7 | $2.4 \times 10^2$ | $2.1 \times 10^2$ | $2.3 \times 10^2$ | 2.4 |
| 6 | $2.0 \times 10^2$ | $2.0 \times 10^2$ | $3.0 \times 10^2$ | 2.4 |
| 5 | $1.0 \times 10^1$ | $2.0 \times 10^1$ | $1.0 \times 10^1$ | 1.1 |
| 0 | TNTC | TNTC | TNTC | |

As shown in Table 13, the log reduction in colony count is starting to become more similar between all concentrations. The trend is starting to show the higher end of the MSM percentage conditions becoming similar in log reduction then the lower end of the MSM percentage conditions. The 12 μg/ml methicillin conditions at 6%-7% MSM are showing a higher log reduction in colony count overall except for the 5% MSM and 60 μg/ml condition and 6% MSM and 12 μg/ml methicillin condition, which have the highest log reduction in colony count. One hypothetical explanation for this result is that this could possibly be showing an optimum concentration for this time period.

The 30 and 60 μg/ml methicillin had an overall better reduction than the 24 hour results on the 8%-12% MSM conditions. The 60 μg/ml maintains a higher average log reduction in colony count compared to the first 24 hour period among the three concentrations of antibiotic. Two points of interest are (1) the 6% MSM at 12 μg/ml methicillin condition having a 4.1 log reduction in colony count and (2) the 5% MSM and 60 μg/ml methicillin condition having a 4.1 log reduction in colony count. One purely hypothetical explanation for this is that the methicillin has additional polar binding sites for MSM thus providing optimum concentration for possible intake into the cells. The overall graph is showing a more even reduction on the concentrations from 8% through 16% MSM. Negative LB controls showed no signs of contamination. LB positive controls showed turbid growth having a TNTC at the $10^5$ plating. The negative 5%, 10%, and 16% MSM controls had no signs of contamination. The antibiotic controls showed no signs of significant reduction from the initial inoculums, and the negative controls showed no signs of contamination.

TABLE 14

ATCC strain 43300 *Staphylococcus aureus* survival in 5-16% MSM and 12, 30 or 60 μg/ml methicillin for 72 hours.

| % MSM Concentration | 12 μg/ml methicillin/ MSM (cfu/ml) | 12 μg/ml methicillin/ MSM (cfu/ml) | 12 μg/ml methicillin/ MSM (cfu/ml) | 72 hours Average Log |
|---|---|---|---|---|
| 16 | $3.3 \times 10^2$ | $3.1 \times 10^2$ | $3.4 \times 10^2$ | 2.5 |
| 15 | $1.6 \times 10^2$ | $2.1 \times 10^2$ | $2.2 \times 10^2$ | 2.3 |
| 14 | $2.2 \times 10^2$ | $2.5 \times 10^2$ | $2.0 \times 10^2$ | 2.3 |
| 13 | $1.4 \times 10^2$ | $1.7 \times 10^2$ | $1.6 \times 10^2$ | 2.2 |
| 12 | $2.3 \times 10^2$ | $2.5 \times 10^2$ | $2.6 \times 10^2$ | 2.4 |

TABLE 14-continued

ATCC strain 43300 *Staphylococcus aureus* survival in 5-16% MSM and 12, 30 or 60 µg/ml methicillin for 72 hours.

| | | | | |
|---|---|---|---|---|
| 11 | $5.1 \times 10^2$ | $4.9 \times 10^2$ | $5.0 \times 10^2$ | 2.7 |
| 10 | $2.1 \times 10^2$ | $1.9 \times 10^2$ | $1.8 \times 10^2$ | 2.3 |
| 9 | $1.1 \times 10^2$ | $1.3 \times 10^2$ | $1.4 \times 10^2$ | 2.1 |
| 8 | $4 \times 10^1$ | $5 \times 10^1$ | $5 \times 10^1$ | 1.7 |
| 7 | 0 | 0 | 0 | 0 |
| 6 | 0 | 0 | 0 | 0 |
| 5 | $2.4 \times 10^2$ | $2.7 \times 10^2$ | $2.6 \times 10^2$ | 2.4 |
| 0 | TNTC | TNTC | TNTC | |

| % MSM Concentration | 30 µg/ml methicillin/MSM (cfu/ml) | 30 µg/ml methicillin/MSM (cfu/ml) | 30 µg/ml methicillin/MSM (cfu/ml) | 72 hours Average Log |
|---|---|---|---|---|
| 16 | $1.0 \times 10^2$ | $1.2 \times 10^2$ | $1.1 \times 10^2$ | 2.0 |
| 15 | $2.7 \times 10^2$ | $2.7 \times 10^2$ | $2.9 \times 10^2$ | 2.4 |
| 14 | $1.9 \times 10^2$ | $2.0 \times 10^2$ | $2.2 \times 10^2$ | 2.3 |
| 13 | $1.7 \times 10^2$ | $1.8 \times 10^2$ | $1.7 \times 10^2$ | 2.2 |
| 12 | $1.6 \times 10^2$ | $1.9 \times 10^2$ | $1.9 \times 10^2$ | 2.3 |
| 11 | $1.1 \times 10^2$ | $1.3 \times 10^2$ | $1.1 \times 10^2$ | 2.1 |
| 10 | $1.0 \times 10^2$ | $1.0 \times 10^2$ | $1.0 \times 10^2$ | 2.0 |
| 9 | $1.2 \times 10^2$ | $1.1 \times 10^2$ | $1.0 \times 10^2$ | 2.0 |
| 8 | $2.2 \times 10^2$ | $2.5 \times 10^2$ | $2.4 \times 10^2$ | 2.4 |
| 7 | $2.0 \times 10^1$ | $2.0 \times 10^1$ | $2.0 \times 10^1$ | 1.3 |
| 6 | TNTC | TNTC | TNTC | 5.2 |
| 5 | $6 \times 10^1$ | $8 \times 10^1$ | $7 \times 10^1$ | 1.8 |
| 0 | TNTC | TNTC | TNTC | |

| % MSM Concentration | 60 µg/ml methicillin/MSM (cfu/ml) | 60 µg/ml methicillin/MSM (cfu/ml) | 60 µg/ml methicillin/MSM (cfu/ml) | 72 hours Average Log |
|---|---|---|---|---|
| 16 | $2.0 \times 10^1$ | $4.0 \times 10^1$ | $2.0 \times 10^1$ | 1.4 |
| 15 | $1.3 \times 10^2$ | $1.3 \times 10^2$ | $1.3 \times 10^2$ | 2.1 |
| 14 | $1.1 \times 10^2$ | $1.4 \times 10^2$ | $1.4 \times 10^2$ | 2.1 |
| 13 | $1.7 \times 10^2$ | $1.5 \times 10^2$ | $1.8 \times 10^2$ | 2.2 |
| 12 | $1.2 \times 10^2$ | $1.3 \times 10^2$ | $1.2 \times 10^2$ | 2.1 |
| 11 | $1.0 \times 10^2$ | $1.0 \times 10^2$ | $1.1 \times 10^2$ | 2.0 |
| 10 | $8.0 \times 10^1$ | $9.0 \times 10^1$ | $8.0 \times 10^1$ | 1.9 |
| 9 | $8.0 \times 10^1$ | $8.0 \times 10^1$ | $8.0 \times 10^1$ | 1.9 |
| 8 | $1.0 \times 10^2$ | $1.1 \times 10^2$ | $1.1 \times 10^2$ | 2.0 |
| 7 | $5.0 \times 10^1$ | $4.0 \times 10^1$ | $6.0 \times 10^1$ | 1.7 |
| 6 | 0 | 0 | 0 | 0 |
| 5 | 0 | 0 | 0 | 0 |
| 0 | TNTC | TNTC | TNTC | |

As shown in Table 14, the 6% and 7% MSM and 12 µg/ml methicillin conditions at 72 hours showed no sign of colonies on all platings. The 6% and 7% MSM tubes were then taken out of the experiment and tested for MRSA. The tubes were spun down at 5000 rpm for 10 minutes. The supernatant was then decanted into 90 mls of Mueller-Hinton broth with 6 µg/ml methicillin. This is for enrichment and the recovery of any MRSA cells that may be present wether healthy or stressed. The pellet had 10 mls Mueller-Hinton broth with 6 µg/ml methicillin added to it to recover any cells that may be present. Both vessels were incubated at 35° C. for 48 hours and plated each 24 hours. Each vessel was plated at 10 dilutions to obtain a 1 cfu detection limit. Since all vessels were at a 1/10 dilution in the enrichment solution plating each vessel in this manner gave us a detection limit of 1 cfu/ml. This was considered to be a true total kill since no recovery of the organism could be made. This time point for graphing purposes will be reported as 0 logs.

As shown in Table 14, the 5% and 6% MSM and 60 µg/ml methicillin conditions at 72 hours showed no sign of colonies on all platings. The 5% and 6% MSM tubes were then taken out of the experiment and tested for MRSA. The tubes were spun down at 5000 rpm for 10 minutes. The supernatant was then decanted into 90 mls of Mueller-Hinton broth with 6 µg/ml methicillin. This is for enrichment and the recovery of any MRSA cells that may be present wether healthy or stressed. The pellet had 10 mls Mueller-Hinton broth with 6 µg/ml methicillin added to it to recover any cells that may be present. Both vessels were incubated at 35° C. for 48 hours and plated each 24 hours. Each vessel was plated at 10 dilutions to obtain a 1 cfu detection limit. Since all vessels were at a 1/10 dilution in the enrichment solution plating each vessel in this manner gave us a detection limit of 1 cfu/ml. This was considered to be a true total kill since no recovery of the organism could be made. This time point for graphing purposes will be reported as 0 logs.

When compared to the oxacillin experiment shown in Example 6, the results at the 72 hour time point show a higher log reduction in colony count except for 6% MSM at 30 µg/ml methicillin condition. One purely hypothetical explanation for this is that methicillin has more binding sites for MSM and is trending to be more uniform in reduction between all concentrations. The 72 hour mark trend is starting to show the lower and higher concentration have a more uniform reduction with the lower end having a larger impact on non-recovery of viable organisms at the concentrations of 5-7% MSM. The methicillin assay is showing a lower rate of reverting back to antibiotic resistance than the oxacillin assay in the prior experiment. One purely hypothetical explanation for this is that MSM is getting into the cells more efficiently due to the increase of possible binding sites of methicillin. The 72 hour time point of methicillin is showing more true kills of MRSA then seen before. One thing to note is that MSM was replaced with the same concentration and not replaced at a fixed concentration as done in prior experiments.

TABLE 15

ATCC strain 43300 *Staphylococcus aureus* survival in 5-16% MSM and 12, 30 or 60 µg/ml methicillin for 96 hours.

| % MSM Concentration | 12 µg/ml methicillin/MSM (cfu/ml) | 12 µg/ml methicillin/MSM (cfu/ml) | 12 µg/ml methicillin/MSM (cfu/ml) | 96 hours Average Log |
|---|---|---|---|---|
| 16 | $1.1 \times 10^2$ | $1.3 \times 10^2$ | $1.2 \times 10^2$ | 2.1 |
| 15 | $1.4 \times 10^2$ | $1.3 \times 10^2$ | $1.6 \times 10^2$ | 2.2 |
| 14 | $1.2 \times 10^2$ | $1.2 \times 10^2$ | $1.3 \times 10^2$ | 2.1 |
| 13 | $1.1 \times 10^2$ | $1.0 \times 10^2$ | $1.0 \times 10^2$ | 2.0 |
| 12 | $1.6 \times 10^2$ | $1.8 \times 10^2$ | $1.8 \times 10^2$ | 2.2 |
| 11 | $1.0 \times 10^2$ | $1.1 \times 10^2$ | $1.2 \times 10^2$ | 2.0 |
| 10 | $1.1 \times 10^2$ | $1.2 \times 10^2$ | $1.2 \times 10^2$ | 2.1 |
| 9 | TNTC | TNTC | TNTC | 5.2 |
| 8 | 0 | 0 | 0 | 0 |
| 7 | 0 | 0 | 0 | 0 |
| 6 | 0 | 0 | 0 | 0 |
| 5 | $1.33 \times 10^3$ | $1.40 \times 10^3$ | $1.47 \times 10^3$ | 3.1 |
| 0 | TNTC | TNTC | TNTC | |

| % MSM Concentration | 30 µg/ml methicillin/MSM (cfu/ml) | 30 µg/ml methicillin/MSM (cfu/ml) | 30 µg/ml methicillin/MSM (cfu/ml) | 96 hours Average Log |
|---|---|---|---|---|
| 16 | $2.0 \times 10^1$ | $1.8 \times 10^1$ | $1.6 \times 10^1$ | 2.3 |
| 15 | $1.1 \times 10^2$ | $1.1 \times 10^2$ | $1.3 \times 10^2$ | 2.1 |
| 14 | $1.2 \times 10^2$ | $1.3 \times 10^2$ | $1.1 \times 10^2$ | 2.1 |
| 13 | $1.0 \times 10^2$ | $1.5 \times 10^2$ | $1.0 \times 10^2$ | 2.1 |
| 12 | $4.0 \times 10^1$ | $4.0 \times 10^1$ | $4.0 \times 10^1$ | 1.6 |
| 11 | $3.0 \times 10^1$ | $4.0 \times 10^1$ | $3.0 \times 10^1$ | 1.5 |
| 10 | $2.0 \times 10^1$ | $2.0 \times 10^1$ | $1.0 \times 10^1$ | 1.2 |
| 9 | $2.5 \times 10^2$ | $2.7 \times 10^2$ | $2.8 \times 10^2$ | 2.4 |
| 8 | $4.5 \times 10^2$ | $4.5 \times 10^2$ | $4.0 \times 10^2$ | 2.6 |
| 7 | $1.1 \times 10^2$ | $1.3 \times 10^2$ | $1.5 \times 10^2$ | 2.1 |

TABLE 15-continued

ATCC strain 43300 *Staphylococcus aureus* survival in 5-16% MSM and 12, 30 or 60 μg/ml methicillin for 96 hours.

| | | | | |
|---|---|---|---|---|
| 6 | TNTC | TNTC | TNTC | 5.2 |
| 5 | $4.2 \times 10^2$ | $4.1 \times 10^2$ | $4.5 \times 10^2$ | 2.6 |
| 0 | TNTC | TNTC | TNTC | 5.2 |

| % MSM Concentration | 60 μg/ml methicillin/ MSM (cfu/ml) | 60 μg/ml methicillin/ MSM (cfu/ml) | 60 μg/ml methicillin/ MSM (cfu/ml) | 96 hours Average Log |
|---|---|---|---|---|
| 16 | $4.0 \times 10^1$ | $7.0 \times 10^1$ | $6.0 \times 10^1$ | 1.75 |
| 15 | $1.0 \times 10^1$ | $1.0 \times 10^1$ | $1.0 \times 10^1$ | 1 |
| 14 | $1.0 \times 10^1$ | $1.0 \times 10^1$ | $1.0 \times 10^1$ | 1 |
| 13 | $6.0 \times 10^1$ | $3.0 \times 10^1$ | $3.0 \times 10^1$ | 1.6 |
| 12 | $3.0 \times 10^1$ | $2.0 \times 10^1$ | $2.0 \times 10^1$ | 1.4 |
| 11 | $1.0 \times 10^1$ | $2.0 \times 10^1$ | $1.0 \times 10^1$ | 1.1 |
| 10 | $6.0 \times 10^1$ | $6.0 \times 10^1$ | $6.0 \times 10^1$ | 1.8 |
| 9 | $2.0 \times 10^1$ | $3.0 \times 10^1$ | $1.0 \times 10^1$ | 1.3 |
| 8 | $1.39 \times 10^4$ | $1.41 \times 10^4$ | $1.36 \times 10^4$ | 4.1 |
| 7 | $1.2 \times 10^4$ | $1.2 \times 10^4$ | $1.5 \times 10^4$ | 4.1 |
| 6 | 0 | 0 | 0 | 0 |
| 5 | 0 | 0 | 0 | 0 |
| 0 | TNTC | TNTC | TNTC | 5.2 |

As shown in Table 15, at 96 hours and 12 μg/ml methicillin, the 9% MSM concentration showed greater survival of bacteria. One purely hypothetical explanation for this is that the bacteria have reverted to antibiotic resistance. The 5% MSM condition is also showing greater survival of bacteria. The 8% MSM concentration showed no sign of colonies on all platings. The 8% tube was then taken out of the experiment and tested for MRSA. The tube were spun down at 5000 rpm for 10 minutes. The supernatant was then decanted into 90 mls of Mueller-Hinton broth with 6 μg/ml methicillin. This is for enrichment and the recovery of any MRSA cells that may be present wether healthy or stressed. The remaining test tube had 10 mls Mueller-Hinton broth with 6 μg/ml methicillin added to it to recover any cells that may be present. Both vessels were incubated at 35° C. for 48 hours and plated each 24 hours. Each vessel was plated at 10 dilutions to obtain a 1 cfu detection limit. Since all vessels were at a 1/10 dilution in the enrichment solution plating each vessel in this manner gave us a detection limit of 1 cfu/ml. This was considered to be a true total kill since no recovery of the organism could be made. This time point for graphing purposes will be reported as 0 logs.

As shown in Table 15, at 96 hours and 30 μg/ml methicillin, the higher MSM concentrations are showing a greater log reduction in cfu/ml. The 5% to 9% MSM concentrations (except for 6% MSM), are showing less reduction in cfu/ml. At 96 hours and 60 μg/ml methicillin, the 9% to 16% MSM concentrations showed greater log reduction in colony count than at the 72 hour timepoint. The 7% and 8% MSM conditions are showing less reduction in cfu/ml.

The 8% MSM and 12 μg/ml condition shows no survival of viable organisms. TNTC was observed at the 7% and 8% MSM and 60 μg/ml methicillin and the 5% MSM and 12 μg/ml methicillin conditions. Overall, at 96 hours, the 10-16% MSM conditions showed slightly lower or similar colony counts compared to the previous time point of 72 hours.

The 30 μg/ml showed increased colony counts thru the 5 to 9% MSM conditions. The log reduction in colony counts is slightly lower or staying the same for the 10-16% compared to the previous time point and appears to stay constant.

TABLE 16

ATCC strain 43300 *Staphylococcus aureus* survival in 5-16% MSM and 12, 30 or 60 μg/ml methicillin for 120 hours.

| % MSM Concentration | 12 μg/ml methicillin/ MSM (cfu/ml) | 12 μg/ml methicillin/ MSM (cfu/ml) | 12 μg/ml methicillin/ MSM (cfu/ml) | 120 hours Average Log |
|---|---|---|---|---|
| 16 | $2.0 \times 10^2$ | $2.3 \times 10^2$ | $2.4 \times 10^2$ | 2.3 |
| 15 | $2.9 \times 10^2$ | $3.4 \times 10^2$ | $3.1 \times 10^2$ | 2.5 |
| 14 | $3.5 \times 10^2$ | $4.0 \times 10^2$ | $3.8 \times 10^2$ | 2.6 |
| 13 | $2.0 \times 10^2$ | $1.8 \times 10^2$ | $2.1 \times 10^2$ | 2.3 |
| 12 | $1.21 \times 10^3$ | $1.21 \times 10^3$ | $1.21 \times 10^3$ | 4.1 |
| 11 | $1.24 \times 10^4$ | $1.22 \times 10^4$ | $1.23 \times 10^4$ | 4.1 |
| 10 | $1.10 \times 10^4$ | $1.10 \times 10^4$ | $1.13 \times 10^4$ | 4.0 |
| 9 | TNTC | TNTC | TNTC | 5.2 |
| 8 | 0 | 0 | 0 | 0 |
| 7 | 0 | 0 | 0 | 0 |
| 6 | 0 | 0 | 0 | 0 |
| 5 | TNTC | TNTC | TNTC | 5.2 |
| 0 | TNTC | TNTC | TNTC | 5.2 |

| % MSM Concentration | 300 μg/ml methicillin/ MSM (cfu/ml) | 30 μg/ml methicillin/ MSM (cfu/ml) | 30 μg/ml methicillin/ MSM (cfu/ml) | 120 hours Average Log |
|---|---|---|---|---|
| 16 | 0 | 0 | 0 | 0 |
| 15 | $3.0 \times 10^1$ | $4.0 \times 10^1$ | $3.0 \times 10^1$ | 1.5 |
| 14 | $5.0 \times 10^1$ | $7.0 \times 10^1$ | $6.0 \times 10^1$ | 1.8 |
| 13 | $5.0 \times 10^1$ | $4.0 \times 10^1$ | $4.0 \times 10^1$ | 1.6 |
| 12 | 0 | 0 | 0 | 0 |
| 11 | 0 | 0 | 0 | 0 |
| 10 | 0 | 0 | 0 | 0 |
| 9 | $1.3 \times 10^3$ | $1.1 \times 10^3$ | $1.2 \times 10^3$ | 3.1 |
| 8 | $9.0 \times 10^2$ | $9.1 \times 10^2$ | $9.5 \times 10^2$ | 3.0 |
| 7 | TNTC | TNTC | TNTC | 5.2 |
| 6 | TNTC | TNTC | TNTC | 5.2 |
| 5 | $1.21 \times 10^3$ | $1.21 \times 10^3$ | $1.21 \times 10^3$ | 3.0 |
| 0 | TNTC | TNTC | TNTC | 5.2 |

| % MSM Concentration | 60 μg/ml methicillin/ MSM (cfu/ml) | 60 μg/ml methicillin/ MSM (cfu/ml) | 60 μg/ml methicillin/ MSM (cfu/ml) | 120 hours Average Log |
|---|---|---|---|---|
| 16 | $1.0 \times 10^1$ | $2.0 \times 10^1$ | $2.0 \times 10^1$ | 1.2 |
| 15 | 0 | 0 | 0 | 0 |
| 14 | 0 | 0 | 0 | 0 |
| 13 | $3.0 \times 10^1$ | $3.0 \times 10^1$ | $3.0 \times 10^1$ | 1.5 |
| 12 | 0 | 0 | 0 | 0 |
| 11 | 0 | 0 | 0 | 0 |
| 10 | $1.0 \times 10^1$ | $1.0 \times 10^1$ | $1.0 \times 10^1$ | 1 |
| 9 | $1.0 \times 10^1$ | $1.0 \times 10^1$ | $1.0 \times 10^1$ | 1 |
| 8 | TNTC | TNTC | TNTC | 5.2 |
| 7 | TNTC | TNTC | TNTC | 5.2 |
| 6 | 0 | 0 | 0 | 0 |
| 5 | 0 | 0 | 0 | 0 |
| 0 | TNTC | TNTC | TNTC | 5.2 |

As shown in Table 16, at 120 hours and 30 μg/ml methicillin, the 10%, 11%, 12% and 16% MSM concentrations showed no sign of colonies; and at 120 hours and 60 μg/ml methicillin, the 11%, 12%, 14% and 15% MSM concentrations showed no sign of colonies. Tubes corresponding to these conditions were then taken out of the experiment and tested for MRSA. The tubes was spun down at 5000 rpm for 10 minutes. The supernatant was then decanted into 90 mls of Mueller-Hinton broth with 6 μg/ml methicillin. This is for enrichment and the recovery of any MRSA cells that may be present wether healthy or stressed. The remaining test tubes had 10 mls Mueller-Hinton broth with 6 μg/ml methicillin added to them to recover any cells that may be present. Both vessels were incubated at 35° C. for 48 hours and plated every 24 hours. Each vessel was plated at 10 times each to obtain a 1 cfu detection limit. Since both vessels were at a 1/10 dilution in the enrichment solution plating each vessel in this manner gave us a detection limit of 1 cfu. This was considered to be a true total kill since no recovery of the organism could be made. This time point for graphing purposes will be reported as 0 logs.

Overall, at 120 hours and 12 µg/ml methicillin, there is slight increase in cfu/ml at 13-16% MSM and a greater increase at the 10%-12% MSM concentrations compared to the previous time point. The 5% MSM and 12 µg/ml methicillin condition showed TNTC cfu/ml. The higher concentrations of 13-16% MSM only showed a slight increase in cfu/ml. One purely hypothetical explanation for this is that the bacteria are reverting to antibiotic resistance, but that the higher concentrations of MSM had a significant impact on slowing down the reversion process since we see a slight increase in cfu/ml at higher MSM concentrations while the lower concentrations have a significant rise in cfu/ml.

At 30 µg/ml methicillin, the 16%, 12%, 11%, and 10% MSM conditions showed true kill with no recovery noticed. The 15%, 14%, and 13% MSM conditions showed slight reduction in cfu/ml from the previous time point. The 5%, 8% and 9% MSM conditions showed a slightly higher cfu/ml than the previous time point.

At 60 µg/ml methicillin, the 15%, 14%, 12% and 11% MSM conditions showed true kill with no recovery of organism. The 10% and 9% concentration points show a continued decrease in cfu/ml from the previous time point. One possibility is that these concentrations of MSM and antibiotic have a greater impact on MRSA Overall, the combination of MSM and methicillin demonstrated ability to significantly decrease the MRSA colony forming units at all time points evaluated. Based on the results of this experiment MSM appears to have the ability to restore sensitivity of MRSA to methicillin in vitro. When compared to oxacillin in the previous experiment the rate of reduction in log value was more even across the concentrations. One hypothetical explanation for this is that methicillin has more binding sites when compared in structure with oxacillin show up in the overall experiment. There are more significant true kills and the reduction over all the concentrations is greater with methicillin than oxacillin.

Overall, the data presented in Tables 12-16 shows that at the first 24 hours there was a higher reduction at the lower percentages of MSM for all three concentrations of methicillin evaluated. This trend is slightly changing at 48 hours with maximum reduction being observed in the mid to upper MSM concentrations. By 72 hours the trend has definitely switched to higher log reduction at the higher MSM concentrations. MSM was only added when additional growth media (LB containing the same original MSM concentration as the growth vial) was added to maintain original volume in the vial. For instance if a 1 ml aliquot of the 12 µg/ml methicillin and 5% MSM was removed for plating then 1 ml of LB containing 5% MSM would be added back. The antibiotics were added at the appropriate concentrations every 24 hours as previously described.

The following are offered as hypothetical explanations for some of the effects seen above; however, these explanations are not intended to be limiting. One hypothetical and non-limiting possibility for the observed results is that MSM is being consumed by the organisms. Another hypothetical and non-limiting possibility for the observed results is that the ability of MSM to cause the reversion to sensitivity could be due to an ability of MSM to carry the methicillin into the MRSA cells. Another hypothetical and non-limiting possibility for the observed results is that too high of a level of MSM is less effective at certain time points. For instance, this may be due to competition of an overabundance of free MSM molecules competing with MSM that has bind with the methicillin at the higher concentrations. This would have more free MSM entering the cells than the methicillin bound MSM. The lower concentrations have a higher overall percentage of the total MSM molecules in solution are bound to the methicillin, allowing more of the bound methicillin to enter the cell since there was less free MSM to compete. Under this hypothesis, for a given number of MSM molecules that will enter the MRSA cell the ratio of MSM to methicillin is important to obtain the maximum effect. If an overabundance of MSM is present then the chance of MSM molecules not bound to the methicillin penetrating the cell increases.

It will be understood by those of skill in the art that numerous and various modifications can be made without departing from the spirit of the present disclosure. Therefore, it should be clearly understood that the embodiments disclosed herein are illustrative only.

We claim:

1. A method of sensitizing methicillin resistant *Staphylococcus aureus* (MRSA) to a Beta-lactam antibiotic to which the MRSA is resistant, the method comprising:
   selecting MRSA resistant to the Beta-lactam antibiotic; and
   contacting the MRSA with a composition comprising a therapeutically effective amount of methylsulfonylmethane (MSM), thereby sensitizing the MRSA to the Beta-lactam antibiotic.

2. The method of claim 1, wherein the Beta-lactam antibiotic is selected from the group consisting of a penicillin derivative, a cephalosporin, a penem, a monobactam, a carbapenem, a Beta-lactamase inhibitor or a combination of two or more thereof.

3. The method of claim 2, wherein the Beta-lactam antibiotic is a penicillin derivative.

4. The method of claim 3, wherein the penicillin derivative is methicillin or oxacillin.

5. The method of claim 1, wherein the therapeutically effective amount of MSM is about 5-16% MSM, about 5-10% MSM, about 5-8% MSM, about 9-16% MSM or about 10-15% MSM.

6. The method of claim 1, wherein the therapeutically effective amount of MSM is about 12-13% MSM.

7. The method of claim 1, wherein the therapeutically effective amount of MSM is about 5, 6, 7, 8, 9, 10, 11, 12, 13, 14, 15 or 16% MSM.

8. The method of claim 1, wherein the composition further comprises 0-5% sodium chloride.

9. The method of claim 1, further comprising inhibiting the MRSA, comprising:
   contacting the sensitized MRSA with a composition comprising a therapeutically effective amount of the Beta-lactam antibiotic, thereby inhibiting the MRSA.

10. The method of claim 9, wherein the Beta-lactam antibiotic is selected from the group consisting of a penicillin derivative, a cephalosporin, a penem, a monobactam, a carbapenem, a Beta-lactamase inhibitor or a combination of two or more thereof.

11. The method of claim 10, wherein the Beta-lactam antibiotic is a penicillin derivative.

12. The method of claim 11, wherein the penicillin derivative is methicillin or oxacillin.

13. The method of claim 9, wherein the therapeutically effective amount of MSM is about 5-16% MSM, about 5-10% MSM, about 5-8% MSM, about 9-16% MSM or about 10-15% MSM.

14. The method of claim 9, wherein the therapeutically effective amount of MSM is about 12-13% MSM.

15. The method of claim 9, wherein the therapeutically effective amount of MSM is about 5, 6, 7, 8, 9, 10, 11, 12, 13, 14, 15 or 16% MSM.

16. A method of sensitizing methicillin resistant *Staphylococcus aureus* (MRSA) to a penicillin derivative to which the MRSA is resistant, the method comprising:

selecting MRSA resistant to the penicillin derivative; and contacting the MRSA with a composition comprising about 12-13% methylsulfonylmethane (MSM), thereby sensitizing the MRSA to the penicillin derivative.

17. The method of claim 16, wherein the penicillin derivative is methicillin or oxacillin.

18. A method of inhibiting methicillin resistant *Staphylococcus aureus* (MRSA) that is resistant to a penicillin derivative, comprising:

selecting MRSA resistant to the penicillin derivative; and contacting the MRSA with a composition comprising about 12-13% methylsulfonylmethane (MSM) and a therapeutically effective amount of a penicillin derivative, thereby inhibiting the MRSA.

19. The method of claim 18, wherein the penicillin derivative is methicillin or oxacillin.

\* \* \* \* \*

UNITED STATES PATENT AND TRADEMARK OFFICE
CERTIFICATE OF CORRECTION

PATENT NO.      : 8,217,085 B2
APPLICATION NO. : 13/399921
DATED           : July 10, 2012
INVENTOR(S)     : Benjamin et al.

Page 1 of 1

It is certified that error appears in the above-identified patent and that said Letters Patent is hereby corrected as shown below:

In the Specification:

At column 15, line 46, "of method" should read --of a method--.
At column 18, line 39, "strains It" should read --strains. It--.
At column 22, line 17, "VIII." should read --IX.--.
At column 23, line 51, "general" should read --generally--.
At column 31, line 56, "f ruse" should read --for use--.
At column 37, line 35, "dilutionsto" should read --dilutions to--.
At column 38, line 15, "oxacillin Results" should read --oxacillin. Results--.
At column 40, line 15, "dilutionsto" should read --dilutions to--.
At column 41, line 45, "dilutionsto" should read --dilutions to--.
At column 43, line 22, "oxacillin We" should read --oxacillin. We--.
At column 45, line 24, "oxacillin" should read --oxacillin.--.
At column 45, line 40, "any the" should read --any of the--.
At column 46, line 15, "dilutionsto" should read --dilutions to--.
At column 49, line 9, "oxacillin Two" should read --oxacillin. Two--.
At column 55, line 65, "8himadzu" should read --Shimadzu--.
At column 63, line 36, "wether" should read --whether--.

Signed and Sealed this
Sixth Day of November, 2012

David J. Kappos
*Director of the United States Patent and Trademark Office*